US007579447B2

(12) United States Patent
Jaye et al.

(10) Patent No.: US 7,579,447 B2
(45) Date of Patent: Aug. 25, 2009

(54) ANTIBODIES AGAINST LLG POLYPEPTIDES OF THE TRIACYLGLYCEROL LIPASE FAMILY

(75) Inventors: Michael C. Jaye, Glenside, PA (US); Kim-Anh Thi Doan, Audubon, PA (US); John A. Krawiec, Gulph Mills, PA (US); Kevin J. Lynch, Gurnee, IL (US); Dilip V. Amin, Lansdale, PA (US); Victoria J. South, Collegeville, PA (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 11/369,410

(22) Filed: Mar. 7, 2006

(65) Prior Publication Data

US 2007/0101451 A1    May 3, 2007

Related U.S. Application Data

(62) Division of application No. 10/128,449, filed on Apr. 23, 2002, now Pat. No. 7,056,720, which is a division of application No. 08/985,492, filed on Dec. 5, 1997, now Pat. No. 6,395,530.

(60) Provisional application No. 60/032,254, filed on Dec. 6, 1996, provisional application No. 60/032,783, filed on Dec. 6, 1996.

(51) Int. Cl.
  *C07K 16/00* (2006.01)
  *C07K 16/40* (2006.01)
  *C12N 5/06* (2006.01)
  *C12N 5/12* (2006.01)
  *A61K 39/395* (2006.01)
  *A61K 39/00* (2006.01)

(52) U.S. Cl. .............................. 530/388.25; 530/387.1; 530/387.9; 530/388.1; 530/388.26; 530/389.1; 530/389.3; 424/130.1; 424/139.1; 424/141.1; 424/146.1; 424/158.1; 435/326; 435/338; 435/346

(58) Field of Classification Search ....................... None
See application file for complete search history.

(56) References Cited

U.S. PATENT DOCUMENTS

| 4,944,944 | A | 7/1990 | Tang et al. ................. 424/94.6 |
| 5,364,777 | A | 11/1994 | Spencer |
| 5,616,483 | A | 4/1997 | Bjursell et al. .............. 435/198 |
| 5,691,181 | A | 11/1997 | Lowe ......................... 435/325 |
| 5,858,755 | A | 1/1999 | Lowe ......................... 435/198 |
| 5,976,855 | A | 11/1999 | Svendsen et al. |
| 5,998,189 | A | 12/1999 | Blanchard et al. ........... 435/198 |
| 6,074,863 | A | 6/2000 | Svendsen et al. |
| 6,159,947 | A | 12/2000 | Schweighoffer et al. ...... 514/44 |
| 6,337,187 | B1 | 1/2002 | Kapeller-Libermann ....... 435/6 |
| 6,395,530 | B1 | 5/2002 | Jaye et al. .................... 435/198 |
| 6,558,936 | B1 | 5/2003 | Khodadoust et al. ......... 435/198 |
| 6,797,502 | B2 | 9/2004 | Kapeller-Libermann .... 435/198 |
| 6,864,064 | B2 | 3/2005 | Kapeller-Libermann ..... 435/15 |
| 7,008,776 | B1 | 3/2006 | Jaye et al. |
| 7,056,720 | B2 | 6/2006 | Jaye et al. |
| 2003/0108538 | A1 | 6/2003 | Jaye et al. ................... 424/94.6 |
| 2006/0088504 | A1 | 4/2006 | Jaye et al. |

FOREIGN PATENT DOCUMENTS

| WO | WO 94/02610 | 2/1994 |
| WO | WO 94/20619 | 9/1994 |
| WO | WO 94/29446 | 12/1994 |
| WO | 96/38170 A1 | 12/1996 |

OTHER PUBLICATIONS

Attwood Science 2000; 290:471-473.*
Lederman et al. Molecular Immunology 28: 1171-1181, 1991.*
Li et al. PNAS 77: 3211-3214, 1980.*
Östlund-Lindquist Biochem. J. 1979, 179:555-559.*
Falkenberge et al. (J. Clin. Chem. Clin. Biochem. 1984, 22:867-882.*
Skolnick et al. Trends in Biotech. 2000; 18(1):34-39.*
Cooper, D. et al., Genbank Database, Accession No. P11602 (1989).
Eisenberg, S. et al., Lipoprotein Lipase Enhances Binding of Lipoproteins to Heparan Sulfate on Cell Surfaces and Extracellular Matrix, *J. Clin. Invest.* (Nov. 1992), 90: 2013-2021.
Goldberg, I.J. et al., Lipoprotein Metabolism During Acute Inhibition of Lipoprotein Lipase in the Cynomolgus Monkey, *J. Clin. Invest.* (Feb. 1988), 81: 561-568.
Goldberg, I.J. et al., Lipoprotein Metabolism During Acute Inhibition of Hepatic Triglyceride Lipase in the Cynomolgus Monkey, *J. Clin. Invest.* (Dec. 1982), 70: 1184-1192.
Cheng, C. et al., Binding of Lipoprotein Lipase to Endothelial Cells in Culture, *J. Biol. Chem.* (Dec. 25, 1981), 256: 12893-12898.
Shimada, K. et al., Involvement of Cell Surface Heparin Sulfate in the Binding of Lipoprotein Lipase to Cultured Bovine Endothelial Cells, *J. Clin. Invest.* (Oct. 1981), 68: 995-1002.
Saxena, U. et al., Identification and Characterization of the Endothelial Cell Surface Lipoprotein Lipase Receptor, *J. Biol. Chem.* (Sep. 15, 1991), 266: 17516-17521.
Mulder, M. et al., Heparan Sulfate Proteoglycans are Involved in the Lipoprotein Lipase-Mediated Enhancement of the Cellular Binding of Very Low Density and Low Density Lipoproteins, *Biochem. Biophys. Res. Commun.* (Jun. 15, 1992), 185: 582-587.

(Continued)

*Primary Examiner*—Phillip Gambel
*Assistant Examiner*—Sharon Wen
(74) *Attorney, Agent, or Firm*—Fox Rothschild LLP

(57) ABSTRACT

Lipoprotein Lipase like polypeptides, nucleic acids encoding said polypeptides, antisense sequences, and antibodies to said polypeptides are disclosed. Also disclosed are methods for the preparation of said polypeptides in a recombinant system and for the use of said polypeptides to screen for agonists and or antagonists of said polypeptides. Also disclosed are methods and compositions for the treatment of disorders of lipid metabolism.

7 Claims, 16 Drawing Sheets

OTHER PUBLICATIONS

Tsuchiya, S. et al., Establishment and Characterization of a Human Acute Monocytic Leukemia Cell Line (THP-1), *Int. J. Cancer* (1980), 26: 171-176.

Goldberg, I.J., Lipoprotein Lipase and Lipolysis: Central Roles in Lipoprotein Metabolism and Atherogenesis, *J. Lipid Res.* (1996), 37: 693-707.

Gordon, D.J. and B.M. Rifkind, High Density Lipoprotein—The Clinical Implications of Recent Studies, *N. Engl. J. Med.* (Nov. 9, 1989), 321: 1311-1316.

Breslow, J.L., The Metabolic Basis of Inherited Disease, New York: McGraw Hill, 1995: 2031-2052.

Heller, D.A. et al., Genetic and Environmental Influences on Serum Lipid Levels in Twins, *N. Engl. J. Med.* (Apr. 22, 1993), 328: 1150-1156.

Murthy, V. et al., Molecular Pathobiology of the Human Lipoprotein Lipase Gene, *Pharmacol. Ther.* (1996), 70: 101-135.

Bensadoun, A. and D.E. Berryman, Genetics and Molecular Biology of Hepatic Lipase, *Curr. Opin. Lipidol.* (1996), 7: 77-81.

Guerra, R. et al., A Hepatic Lipase (LIPC) Allele Associated with High Plasma Concentrations of High Density Lipoprotein Cholesterol, *Proc. Natl. Acad. Sci. USA* (Apr. 1997), 94: 4532-4537.

LIPID Study Group, Prevention of Cardiovascular Events and Death with Pravastatin in Patients with Coronary Heart Disease and a Broad Range of Initial Cholesterol Levels, *N. Engl. J. Med.* (Nov. 5, 1998), 339: 1349-1357.

Kannel, W.B., Range of Serum Cholesterol Values in the Population Developing Coronary Artery Disease, *Am. J. Cardiol.* (Sep. 28, 1995), 76: 69C-77C.

4S Group, Randomised Trial of Cholesterol Lowering in 4444 Patients with Coronary Heart Disease, *Lancet* (Nov. 19, 1994), 344: 1383-1389.

Sacks, F.M. et al., The Effect of Pravastatin on Coronary Events After Myocardial Infarction in Patients with Average Cholesterol Levels, *N. Engl. J. Med.* (Oct. 3, 1996), 335: 1001-1009.

Shepherd, J. et al., Prevention of Coronary Heart Disease with Pravastatin in Man with Hypercholesterolemia, *N. Engl. J. Med.* (Nov. 16, 1995), 333: 1301-1307.

Downs, J.R. et al., Primary Prevention of Acute Coronary Events with Lovastatin in Men and Women with Average Cholesterol Levels, *JAMA* (May 27, 1998), 279: 1615-1622.

Grundy, S.M., Statin Trials and Goals of Cholelsterol-Lowering Therapy, *Circulation* (1998), 97: 1436-1439.

Hegele, R.A. et al., Hepatic Lipase Deficiency: Clinical, Biochemical, and Molecular Genetics Characteristics, *Arterioscler. Thromb.* (May 1993), 13: 720-728.

Homanics, G.E. et al., Mild Dyslipidemia in Mice Following Targeted Inactivation of the Hepatic Lipase Gene, *J. Biol. Chem.* (1995), 270: 2974-2980.

Mezdour, H. et al., Hepatic Lipase Deficiency Increases Plasma Cholesterol but Reduces Susceptibility to Atherosclerosis in Apolipoprotein E-deficient Mice, *J. Biol. Chem.* (May 23, 1997), 272: 13570-13575.

Busch, S.J. et al., Human Hepatic Triglyceride Lipase Expression Reduces High Density Lipoprotein and Aortic Cholesterol in Cholesterol-fed Transgenic Mice, *J. Biol. Chem.* (Jun. 10, 1994), 269: 16376-16382.

Fan, J. et al., Overexpression of Hepatic Lipase in Transgenic Rabbits Leads to a Marked Reduction of Plasma High Density Lipoproteins and Intermediate Density Lipoproteins, *Proc. Natl. Acad. Sci. USA* (Aug. 1994), 91: 8724-28.

Tabas, I. et al., Lipoprotein Lipase and Sphingomyelinase Synergistically Enhance the Association of Atherogenic Lipoproteins with Smooth Muscle Cells and Extracellular Matrix, *J. Biol. Chem.* (Sep. 25, 1993), 268: 20419-32.

Kozarsky, K.F. et al., Overexpression of the HDL Receptor SR-BI Alters Plasma HDL and Bile Cholesterol Levels, *Nature* (May 22, 1997), 387: 414-417.

Mahley, R.W. and Z. Ji, Remnant Lipoprotein Metabolism: Key Pathways Involving Cell-Surface Heparan Sulfate Proteoglycans and Apolipoprotein E, *J. Lipid Res.* (1990), 40: 1-16.

Farese, R.V. and J. Herz, Cholesterol Metabolism and Embryogenesis, *Trends Genet.* (Mar. 1998), 14: 115-120.

Grosschedl, R. et al., Introduction of a µ Immunoglobulin Gene into the Mouse Germ Line: Specific Expression in Lymphoid Cells and Synthesis of Functional Antibody, *Cell* (Oct. 1984), 38: 647-658.

Mark, G.E. and E.A. Padlan, *Humanization of Monoclonal Antibodies*, in *The Handbook of Experimental Pharmacology*, vol. 113, New York: Springer-Verlag, 1994: 105-134.

Camps, L. et al., Lipoprotein Lipase: cellular Origin and Functional Distribution, *Am. J. Physiol.* (1990), 258: C673-C681.

Semenkovich, C.F. et al., Lipoprotein Lipase and Hepatic Lipase mRNA Tissue Specific Expression, Developmental Regulation, and Evolution, *J. Lipid Res.* (1989), 30: 423-431.

Verhoeven, A.J.M. and H. Jansen, Hepatic Lipase mRNA is Expressed in Rat and Human Steroidogenic Organs, *Biochim. Biophys. Acta* (1994), 1211: 121-124.

Maciag, T. et al., An Endothelial Cell Growth Factor From Bovine Hypothalamus: Identification and Partial Characterization, *Proc. Natl. Acad. Sci. USA* (Nov. 1979), 76: 5674-5678.

Rothwell, J.E. and M.C. Elphick, Lipoprotein Lipase Activity in Human and Guinea-pig Placenta, *J. Dev. Physiol.* (1982), 4: 153-159.

Jameson, B.A. and H. Wolf, The Antigenic Index: A Novel Algorithm for Predicting Antigenic Determinants, *Comput. Applic. in the Biosciences* (Mar. 1988), 4: 181-186.

Amman, E. et al., Tightly Regulated tac Promoter Vectors Useful for the Expression of Unfused and Fused Proteins in *Escherichia coli*, *Gene* (1988), 69: 301-315.

Auffray, C. et al., GenBank Database, Accession No. Z44958 (1994).

Berkner, K., Development of Adenovirus Vectors for the Expression of Heterologous Genes, *Biotechniques* (1988), 6:616-29.

Brady, L. et al., A Serine Protease Triad Forms the Catalytic Centre of a Triacylglycerol Lipase, *Nature* (Feb. 22, 1990), 343: 767-769.

Carlton, V.E.H. et al., Mapping of a Locus for Progressive Familial Intrahepatic Cholestasis (Byler Disease) to 18q21-q22, the Benign Recurrent Intrahepatic Cholestasis Region, *Hum. Mol. Genet.* (1995), 4: 1049-1053.

Chappell, D.A. et al., Cellular Catabolism of Normal Very Low Density Lipoproteins via the Low Density Lipoprotein Receptor-related Protein/$\alpha_2$-Macroglobulin Receptor is Induced by the C-terminal Domain of Lipoprotein Lipase, *J. Biol. Chem.* (Jul. 8, 1994), 269: 18001-18006.

Chowers, Y. et al., The Vδ1 T Cell Receptor Repertoire in Human Small Intestine and Colon, *J. Exp. Med.* (1994), 180:183-190.

Chowers, Y. et al., GenBank Database, Accession No. L32416 (1995).

Dugi, K. et al., Human Hepatic and Lipoprotein Lipase: The Loop Covering the Catalytic Site Mediates Lipase Substrate Specificity, *J. of Biol. Chem.* (Oct. 27, 1995), 270: 25396-25401.

Faustinella, F. et al., Functional Topology of a Surface Loop Shielding the Catalytic Center in Lipoprotein Lipase, *Biochemistry* (1992), 31: 7219-7223.

Ghosh, S. et al., Molecular Cloning and Expression of Rat Hepatic Neutral Cholesteryl Ester Hydrolase, *Biochem. Biophys. Acta* (1995), 1259: 305-312.

Giller, T. et al., Two Novel Human Pancreatic Lipase Related Proteins, hPLRP1 and hPLRP2, *J. Biol. Chem.* (Aug. 15, 1992), 267: 16509-16516.

Hide, W.A. et al., Structure and Evolution of the Lipase Superfamily, *J. Lipid. Res.* (1992), 33: 167-178.

Houwen, R.H.J. et al., Genome Screening by Searching for Shared Segments: Mapping a Gene for Benign Recurrent Intrahepatic Cholestasis, *Nature Genet.* (Dec. 1994), 8: 380-386.

Ishizaki, K. et al., The Biochemical Studies on Phalloidin-Induced Cholestatsis in Rats, *Toxicol. Lett.* (1997), 90: 29-34.

Liu, M. et al., Alteration of Lipid Profiles in Plasma of Transgenic Mice Expressing Human Lipoprotein Lipase, *J. Biol. Chem.* (Apr. 15, 1994), 269: 11417-11424.

Lo, J. et al., Lipoprotein Lipase: Role of Intramolecular Disulfide Bonds in Enzyme Catalysis, *Biochemical and Biophysical Res. Commun.* (Jan. 5, 1995), 206: 266-271.

Ma, Y. et al., Mutagenesis in Four Candidate Heparin Binding Regions (Residues 279-282, 291-304, 390-393, and 439-448) and Identification of Residues Affecting Heparin Binding of Human Lipoprotein Lipase, *J. Lipid Res.* (1994), 35: 2049-2059.

Marra, M. et al., GenBank Database, Accession No. AA137809 (1996).

Martin, G. et al., Isolation and cDNA Sequence of Human Postheparin Plasma Hepatic Triglyceride Lipase, *J. of Biol. Chem.* (1988), 263: 10907-10914.

Nordestgaard, B.G. et al., Atherosclerosis and Arterial Influx of Lipoproteins, *Curr. Opin. Lipidol.* (1994), 5: 252-257.

Olivecrona, G. and T. Olivecrona, Triglyceride Lipases and Atherosclerosis, *Curr. Opin. Lipidol.* (1995), 6: 291-305.

Ranganathan, G. et al., Tissue Specific Expression of Human Lipoprotein Lipase, *J. Biol. Chem.* (Mar. 31, 1995), 270: 7149-7155.

Rutledge, J.C. and I.J. Goldberg, Lipoprotein Lipase (LpL) Affects Low Density Lipoprotein (LDL) Flux Through Vascular Tissue: Evidence that LpL Increases LDL Accumulation in Vascular Tissue, *J. Lipid Res.* (1994), 35: 1152-60.

Semenkovich, C.F. et al., In Vitro Expression and Site-specific Mutagenesis of the Cloned Human Lipoprotein Lipase Gene, *J. Biol. Chem.* (Apr. 5, 1990), 265: 5429-5433.

Shimada, M. et al., Overexpression of Human Lipoprotein Lipase in Transgenic Mice, *J. Biol. Chem.* (Aug. 25, 1993), 268: 17924-17929.

Strautnieks, S.S. et al., Locus Heterogeneity in Progressive Familial Intrahepatic Cholestasis, *J. Med. Genet.* (1996), 33: 833-836.

van Tilbeurgh, H. et al., Lipoprotein Lipase, *J. of Biol. Chem.* (Feb. 11, 1994), 269: 4626-4633.

Verhoeven, A.J.M. et al., Hepatic Lipase Gene is Transcribed in Rat Adrenals into a Truncated mRNA, *J. Lipid Res.* (1994), 35: 966-975.

Warren, R. et al., Rabbit Hepatic Lipase cDNA Sequence: Low Activity is Associated with Low Messenger RNA Levels, *J. of Lipid Res.* (1991), 32: 1333-1339.

Williams, K.J., The Response-to-Retention Hypothesis of Early Artherogenesis, *Art. Thromb. and Vasc. Biol.* (1995), 15: 551-561.

Winkler, F.K. et al., Structure of Human Pancreatic Lipase, *Nature* (Feb. 22, 1990), 343: 771-774.

Wong, H. et al., Lipoprotein Lipase Domain Function, *J. of Biol. Chem.* (Apr. 8, 1994), 269: 10319-10323.

Wong, H. et al., Domain Exchange: Characterization of a Chimeric Lipase of Hepatic Lipase and Lipoprotein Lipase, *Proc. Natl. Acad. Sci. USA* (Dec. 1991), 88:11290-11294.

Zambon, A. et al., Prevention of Raised Low-Density Lipoprotein Cholesterol in a Patient with Familial Hypercholesterolaemia and Lipoprotein Lipase Deficiency, *Lancet* (May 1, 1993), 341: 1119-1121.

Zilversmit, D.B., A Proposal Linking Atherogenesis to the Interaction of Endothelial Lipoprotein Lipase with Triglyceride-Rich Lipoproteins, *Circ. Res.* (Dec. 1973), 33: 633-638.

Zilversmit, D.B., Atherogenic Nature of Triglycerides, Postprandial Lipidemia, and Triglyceride-Rich Remnant Lipoproteins, *Clin. Chem.* (1995), 41: 153-158.

Mahaney et al., A Major Locus Influencing Plasma High-Density Liproprotein Cholesterol Levels in the San Antonio Family Heart Study, *Arterioscler. Thromb.* (Oct. 1995), 15:1730-39.

Gershenwald, J.E., et al., Monoclonal Antibodies to Avian Lipoprotein Lipase. Purification of the Enzyme by Immunoaffinity Chromatography, *Biochimica et Biophysica Acta* (1985), 836: 286-95 (Abstract Only).

Cooper, D.A., et al., Avian Lipoprotein Lipase: cDNA Sequence and Reciprocal Regulation of mRNA Levels in Adipose and Heart, *Biochimica et Biophysica Acta* (1989), 1008: 92-101.

Stahnke, G. et al., Human Hepatic Triglyceride Lipase: cDNA Cloning, Amino Acid Sequence and Expression in a Cultured Cell Line, *Differentiation* (1987), 35: 45-52.

Datta, S. et al., Human Hepatic Lipase, *J. Biol. Chem.*(1988), 263: 1107-1110.

Ikeda et al., A Sandwich-enzyme Immunoassay for the Quantification of Lipoprotein Lipase and Hepatic Triglyceride Lipase in Human Postheparing Plasma . . . , *J. Lipid Res.* (1990), 31: 1911-1924.

Jaye, M. et al., A Novel Endothelial-derived Lipase That Modulates HDL Metabolism, *Nature Genetics* (1999), 21: 424-28.

Hirata, K. et al., Cloning of a Unique Lipase From Endothelial Cells Extends the Lipase Gene Family, *J. Biol. Chem.* (1999), 274: 14170-14175.

McCoy, M.G. et al., Characterization of the Lipolytic Activity of Endothelial Lipase, *J. Lipid Res.* (2002), 43: 921-929.

Martin, G. et al., "Isolation and cDNA Sequence of Human Postheparin Plasma Hepatic Triglyceride Lipase," Journal of Biological Chemistry, vol. 263, No. 22, pp. 10907-10914, Aug. 5, 1988.

Goldberg, I. et al., "Localization of Lipoprotein lipase mRNA in selected rat tissues." Journal of Lipid Research, vol. 30, pp. 1569-1577 (1989).

Fretland, D. et al., "An In-Vitro Method for Assay of Hormone or Agonist-Stimulated Lipase Activity," Prostaglandins Leukotrienes and Medicine, 28, pp. 45-52 (1987).

Cooper, Dale A., et al. The structure and complete nucleotide sequence of the avian lipoprotein lipase gene. Biochimica et Biophysica Acta, 1129 (1992) p. 166-17. Elsevier Science Publishers B.V.

Ehnholm, C., et al., Purification from Human Plasma of a Heparin-released Lipase with Activity against Triglyceride and Phospholipids, the Journal of Biological Chemistry, vol. 250, No. 17, Sep. 10, pp. 6756-6761 (1975).

Ameis, D., et al., Isolation and Characterization of the Human Hepatic Lipase Gene, the Journal of Biological Chemistry, vol. 265, No. 12, Apr. 25, pp. 6552-6555 (1990).

\* cited by examiner

A. Differential Display Downstream Primer 7: (SEQ ID NO: 17)
   5'TTTTTTTTTGA3'
B. Differential Display Upstream Primer 15: (SEQ ID NO: 18)
   5'GATCAATCGC3'
C. 5'RACE Primer 2a: (SEQ ID NO: 19)
   5'TAGGACATGCACAGTGTAATCTG3'
D. 5'RACE Primer 3a: (SEQ ID NO: 20)
   5'GATTGTGCTGGCCACTTCTC3'
E. 5'RACE Primer 4a: (SEQ ID NO: 21)
   5'GACACTCCAGGGACTGAAG3'
F. 5'RACE Anchor Primer: (SEQ ID NO: 22)
   5'CUACUACUACUAGGCCACGCGTCGACTAGTACGGGIIGGGIIGGGIIG3'
G. 5'RACE Universal Amplification Primer: (SEQ ID NO: 23)
   5'CUACUACUACUAGGCCACGCGTCGACTAGTAC3'
H. 5'LPL Primer: (SEQ ID NO: 24)
   5' ACCACCATG̲GAGAGCAAAGCCCTG3'
   -start codon of human LPL coding sequence is underlined
I. 3'LPL Primer: (SEQ ID NO: 25)
   5' CCAGTTT̲C̲A̲G̲CCTGACTTCTTATTC3'
   -complement to the termination codon of the LPL coding sequence is underlined
J. Primer DLIP774: (SEQ ID NO: 26)
   5'GGCTGTGGACTCAACGATGTC3'
K. Primer LLGgen2a: (SEQ ID NO: 27)
   5'CCGGGTGGGTAGGTACATTTG3'
L. Hlg-gsp1 primer: 5' GGG GGT GAC TTC CAG CCA GGC TGT G 3'
   (nucleotides 772-796 in Fig. 4, SEQ ID NO: 28)
   Hlg-gsp2a primer:    5' AAC TCT GAA AGG CAT GCC TGC CCG G 3'
   (reverse complement of nucleotides 1053-1077 in Fig. 4, SEQ ID NO:29)
   G3PDH 5' primer:    5' TGA AGG TCG GAG TCA ACG GAT TTG GT 3'
                              (SEQ ID NO: 30)
   G3PDH 3' primer:    5' CAT GTG GGC CAT GAG GTC CAC CAC 3'
                              (SEQ ID NO: 31)

FIG. 1

GAATTCGGCTTGATCAATCGCTTCAAAAAGGGGATCTGTCTGAGCTGCCGCAAGAACCGTTGT
AATAGCATTGGCTACAATGCCAAGAAAATGAGGAACAAGAGGAACAGCAAAATGTACCTAAA
AACCCGGGCAGGCATGCCTTTCAGAGGTAACCTTCAGTCCCTGGAGTGTCCCTGAGGAAGGCC
CTTAATACCTCCTTCTTAATACCATGCTGCAGAGCAGGGCACATCCTAGCCCAGGAGAAGTGG
CCAGCACAATCCAATCAAATCGTTGCAAATCAGATTACACTGTGCATGTCCTAGGAAAGGGAA
TCTTTACAAAATAAACAGTGTGGACCCCTCAAAAAAAAAAAAAAAGCCGAATTC

FIG. 2

GAATTCGGCTTCTACTACTACTAGGCCACGCGTCGCCTAGTACGGGGGGGGGGGGGGGGGTCA
GCGAGTCCTTGCCTCCCGGCGGCTCAGGACGAGGGCAGATCTCGTTCTGGGGCAAGCCGTTGA
CACTCGCTCCCTGCCACCGCCCGGGCTCCGTGCCGCCAAGTTTTCATTTTCCACCTTCTCTGC
CTCCAGTCCCCCAGCCCCTGGCCGAGAGAAGGGTCTTACCGGCCGGGATTGCTGGAAACACC
AAGAGGTGGTTTTTGTTTTTTAAAACTTCTGTTTCTTGGGAGGGGGTGTGGCGGGGCAGGATGA
GCAACTCCGTTCCTCTGCTCTGTTTCTGGAGCCTCTGCTATTGCTTTGCTGCGGGGAGCCCCGT
ACCTTTTGGTCCAGAGGGACGGCTGGAAGATAAGCTCCACAAACCCAAAGCTACACAGACTG
AGGTCAAACCATCTGTGAGGTTTAACCTCCGCACCTCCAAGGACCCAGAGCATGAAGGATGCT
ACCTCTCCGTCGGCCACAGCCAGCCCTTAGAAGACTGCAGTTTCAACATGACAGCTAAAACCT
TTTTCATCATTCACGGATGGACGATGAGCGGTATCTTTGAAAACTGGCTGCACAAACTCGTGTC
AGCCCTGCACACAAGAGAGAAAGACGCCAATGTAGTTGTGGTTGACTGGCTCCCCCTGGCCC
ACCAGCTTTACACGGATGCGGTCAATAATACCAGGGTGGTGGGACACAGCATTGCCAGGATGC
TCGACTGGCTGCAGGAGAAGGACGATTTTTCTCTCGGGAATGTCCACTTGATCGGCTACAGCC
TCGGAGCGCACGTGGCCGGGTATGCAGGCAACTTCGTGAAAGGAACGGTGGGCCGAATCACA
GGTTTGGATCCTGCCGGGCCCATGTTTGAAGGGGCCGACATCCACAAGAGGCTCTCTCCGGAC
GATGCAGATTTTGTGGATGTCCTCCACACCTACACGCGTTCCTTCGGCTTGAGCATTGGTATTC
AGATGCCTGTGGGCCACATTGACATCTACCCCAATGGGGGTGACTTCCAGCCAGGCTGTGGAC
TCAACGATGTCTTGGGATCAATTGCATATGGAACAATCACAGAGGTGGTAAAATGTGAGCATG
AGCGAGCCGTCCACCTCTTTGTTGACTCTCTGGTGAATCAGGACAAGCCGAGTTTTGCCTTCC
AGTGCACTGACTCCAATCGCTTCAAAAAGGGGATCTGTCTGAGCTGCCGCAAGAACCGTTGTA
ATAGCATTGGCTACAATGCCAAGAAAATGAGGAACAAGAGGAACAGCAAAATGTACCTAAAA
ACCCGGGCAGGCATGCCTTTCAGAGGTAACCTTCAGTCCCTGGAGTGTCAAGCCGAATTC

FIG. 3

```
GAATTCGCGGCCGCGTCGACGGCGGCTCAGGACGAGGGCAGATCTCGTTCTGGGGCAAGCCG
TTGACACTCGCTCCCTGCCACCGCCCGGGCTCCGTGCCGCCAAGTTTTCATTTTCCACCTTCT
CTGCCTCCAGTCCCCCAGCCCTGGCCGAGAGAAGGGTCTTACCGGCCGGGATTGCTGGAAA
CACCAAGAGGTGGTTTTTGTTTTTTAAAACTTCTGTTTCTTGGGAGGGGGTGTGGCGGGCAGG
ATGAGCAACTCCGTTCCTCTGCTCTGTTTCTGGAGCCTCTGCTATTGCTTTGCTGCGGGGAGCC
CCGTACCTTTTGGTCCAGAGGGACGGCTGGAAGATAAGCTCCACAAACCCAAAGCTACACAG
ACTGAGGTCAAACCATCTGTGAGGTTTAACCTCCGCACCTCCAAGGACCCAGAGCATGAAGG
ATGCTACCTCTCCGTCGGCCACAGCCAGCCCTTAGAAGACTGCAGTTTCAACATGACAGCTAA
AACCTTTTTCATCATTCACGGATGGACGATGAGCGGTATCTTTGAAAACTGGCTGCACAAACT
CGTGTCAGCCCTGCACACAAGAGAGAAAGACGCCAATGTAGTTGTGGTTGACTGGCTCCCCCT
GGCCCACCAGCTTTACACGGATGCGGTCAATAATACCAGGGTGGTGGGACACAGCATTGCCA
GGATGCTCGACTGGCTGCAGGAGAAGGACGATTTTCTCTCGGGAATGTCCACTTGATCGGCT
ACAGCCTCGGAGCGCACGTGGCCGGGTATGCAGGCAACTTCGTGAAGGAACGGTGGGCCGA
ATCACAGGTTTGGATCCTGCCGGGCCCATGTTTGAAGGGGCCGACATCCACAAGAGGCTCTCT
CCGGACGATGCAGATTTTGTGGATGTCCTCCACACCTACACGCGTTCCTTCGGCTTGAGCATT
GGTATTCAGATGCCTGTGGGCCACATTGACATCTACCCCAATGGGGGTGACTTCCAGCCAGGC
TGTGGACTCAACGATGTCTTGGGATCAATTGCATATGGAACAATCACAGAGGTGGTAAAATGT
GAGCATGAGCGAGCCGTCCACCTCTTTGTTGACTCTCTGGTGAATCAGGACAAGCCGAGTTTT
GCCTTCCAGTGCACTGACTCCAATCGCTTCAAAAAGGGGATCTGTCTGAGCTGCCGCAAGAAC
CGTTGTAATAGCATTGGCTACAATGCCAAGAAAATGAGGAACAAGAGGAACAGCAAAATGTA
CCTAAAAACCCGGGCAGGCATGCCTTTCAGAGTTTACCATTATCAGATGAAAATCCATGTCTT
CAGTTACAAGAACATGGGAGAAATTGAGCCCACCTTTTACGTCACCCTTTATGGCACTAATGC
AGATTCCCAGACTCTGCCACTGGAAATAGTGGAGCGGATCGAGCAGAATGCCACCAACA
CCTTCCTGGTCTACACCGAGGAGGACTTGGGAGACCTCTTGAAGATCCAGCTCACCTGGGAGG
GGGCCTCTCAGTCTTGGTACAACCTGTGGAAGGAGTTTCGCAGCTACCTGTCTCAACCCCGCA
ACCCCGGACGGGAGCTGAATATCAGGCGCATCCGGGTGAAGTCTGGGGAAACCCAGCGGAAA
CTGACATTTTGTACAGAAGACCCTGAGAACACCAGCATATCCCCAGGCCGGGAGCTCTGGTTT
CGCAAGTGTCGGGATGGCTGGAGGATGAAAAACGAAACCAGTCCCACTGTGGAGCTTCCC
TGAGGGTGCCCGGGCAAGTCTTGCCAGCAAGGCAGCAAGACTTCCTGCTATCCAAGCCCATG
GAGGAAAGTTACTGCTGAGGACCCACCCAATGGAAGGATTCTTCTCAGCCTTGACCCTGGAGC
ACTGGGAACAACTGGTCTCCTGTGATGGCTGGGACTCCTCGCGGGAGGGGACTGCGCTGCTAT
AGCTCTTGCTGCCTCTCTTGAATAGCTCTAACTCCAAACCTCTGTCCACACCTCCAGAGCA
CCAAGTCCAGATTTGTGTGTAAGCAGCTGGGTGCCTGGGGCCTCTCGTGCACACTGGATTGGT
TTCTCAGTTGCTGGGCGAGCCTGTACTCTGCCTGACGAGGAACGCTGGCTCCGAAGAGGCCCT
GTGTAGAAGGCTGTCAGCTGCTCAGCCTGCTTTGAGCCTCAGTGAGAAGTCCTTCCGACAGGA
GCTGACTCATGTCAGGATGGCAGGCTGGTATCTTGCTCGGGCCCTGGCTGTTGGGGTTCTCAT
GGGTTGCACTGACCATACTGCTTACGTCTTAGCCATTCCGTCCTGCTCCCCAGCTCACTCTCTG
AAGCACACATCATTGGCTTTCCTATTTTCTGTTCATTTTTAATTGAGCAAATGTCTATTGAAC
ACTTAAAATTAATTAGAATGTGGTAATGGACATATTACTGAGCCTCTCCATTTGGAACCCAGTG
GAGTTGGGATTTCTAGACCCTCTTTCTGTTTGGATGGTGTATGTGTATATGCATGGGGAAAGGC
ACCTGGGGCCTGGGGAGGCTATAGGATATAAGCAGTCGACGCGGCCGCGAATTC
```

FIG. 4

MSNSVPLLCFWSLCYCFAAGSPVPFGPEGRLEDKLHKPKATQTEVKPSVRFNLRTSKDPEHEGCY
LSVGHSQPLEDCSFNMTAKTFFIIHGWTMSGIFENWLHKLVSALHTREKDANVVVVDWLPLAHQL
YTDAVNNTRVVGHSIARMLDWLQEKDDFSLGNVHLIGYSLGAHVAGYAGNFVKGTVGRITGLDP
AGPMFEGADIHKRLSPDDADFVDVLHTYTRSFGLSIGIQMPVGHIDIYPNGGDFQPGCGLNDVLGSI
AYGTITEVVKCEHERAVHLFVDSLVNQDKPSFAFQCTDSNRFKKGICLSCRKNRCNSIGYNAKKM
RNKRNSKMYLKTRAGMPFRVYHYQMKIHVFSYKNMGEIEPTFYVTLYGTNADSQTLPLEIVERIE
QNATNTFLVYTEEDLGDLLKIQLTWEGASQSWYNLWKEFRSYLSQPRNPGRELNIRRIRVKSGETQ
RKLTFCTEDPENTSISPGRELWFRKCRDGWRMKNETSPTVELP

FIG. 5

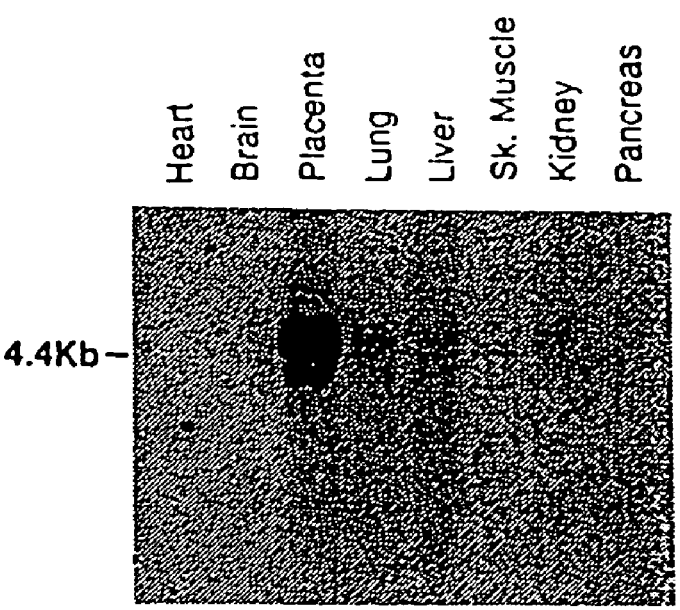
LLG
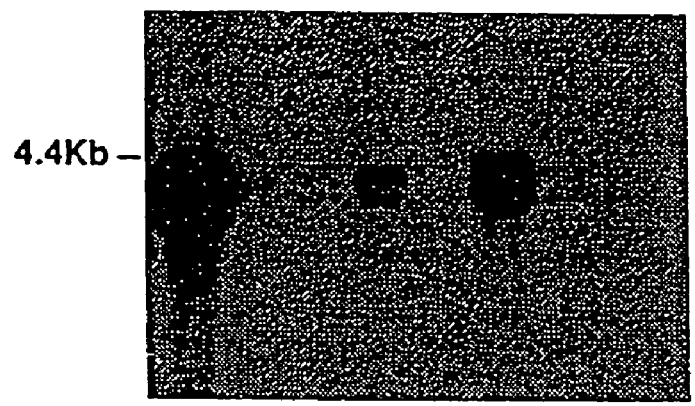
LPL
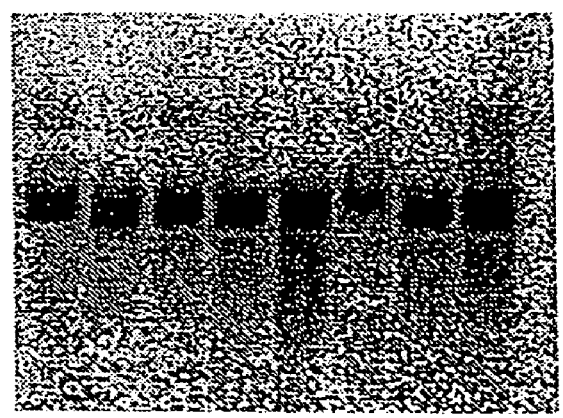
Actin
FIG. 8

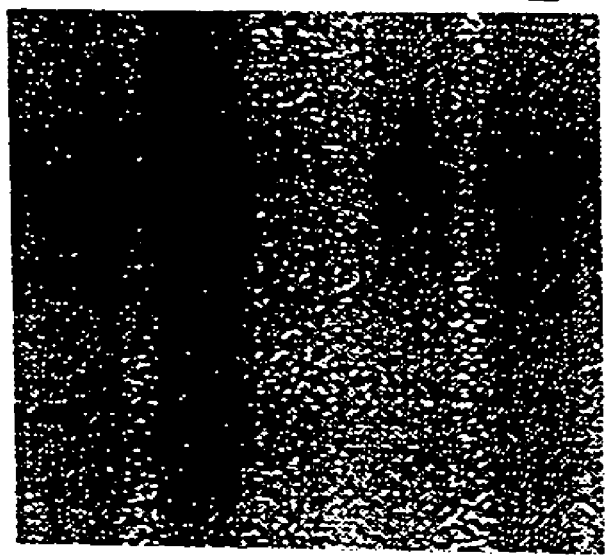
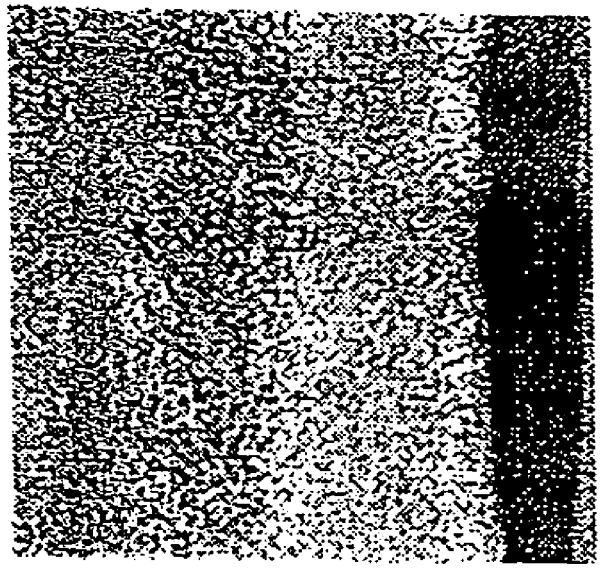
FIG. 9

`GPEGRLEDKLHKPKATC`
MSNSVPLLCFWSLCYCFAAGSPVPFGPEGRLEDKLHKPKATQTEVKPSVRFNLRTSKDPEHEGCYL
SVGHSQPLEDCSFNMTAKTFFIIHGWTMSGIFENWLHKLVSALHTREKDANVVVDWLPLAHQLY
TDAVNNTRVVGHSIARMLDWLQEKDDFSLGNVHLIGYSLGAHVAGYAGNFVKGTVGRITGLDPA
GPMFEGADIHKRLSPDDADFVDVLHTYTRSFGLSIGIQMPVGHIDIYPNGGDFQPGCGLNDVLGSIA
YGTITEVVKCEHERAVHLFVDSLVNQDKPSFAFQCTDSNRFKKGICLSCRKNRCNSIGYNAKKMR
NKRNSKMYLKTRAGMPFRVYHYQMKIHVFSYKNMGEIEPTFYVTLYGTNADSQTLPLEIVERIEQ
NATNTFLVYTEEDLGDLLKIQLTWEGASQSWYNLWKEFRSYLSQPRNPGRELNIRRIRVKSGETQR
KLTFCTEDPENTSISPGRELWFRKCRDGWRMKNETSPTVELP

LLG
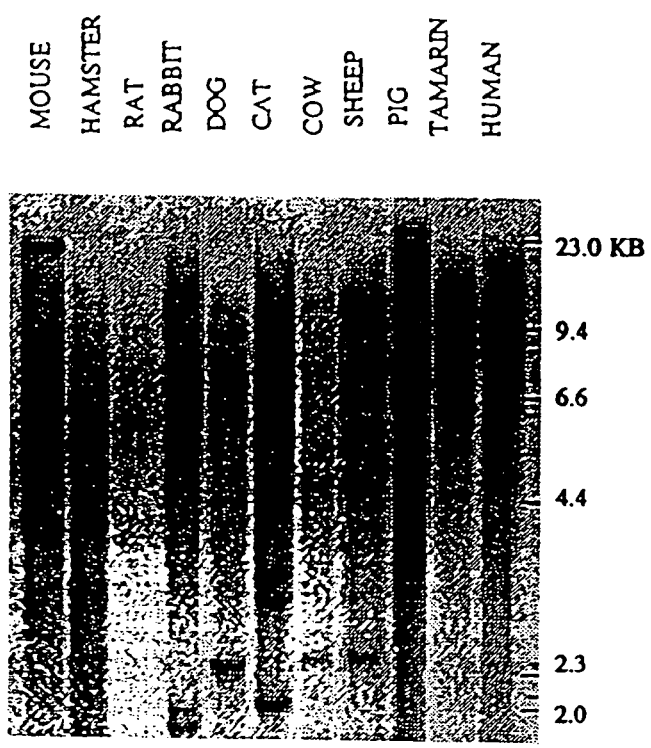
LPL
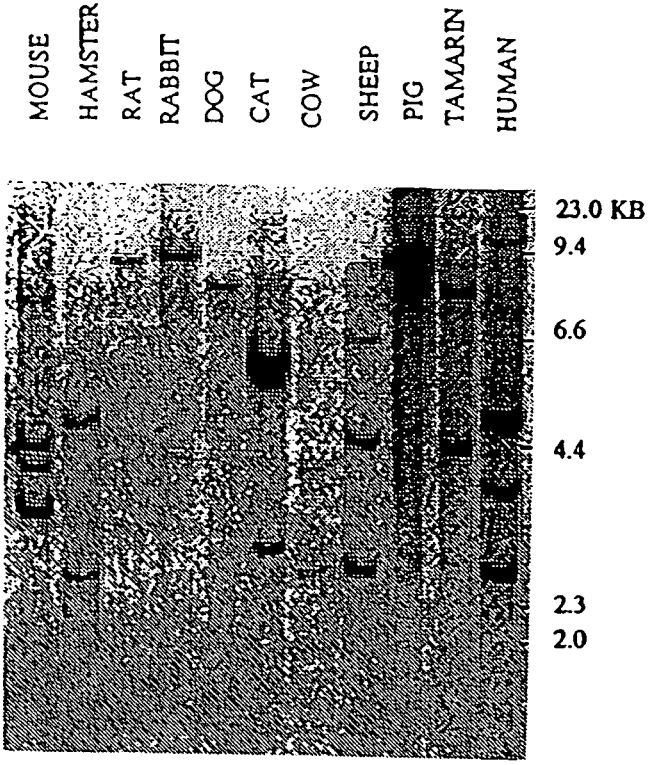
FIG. 16

```
                          SEQUENCE LISTING (1) GENERAL INFORMATION:

(iii) NUMBER OF SEQUENCES: 31

(2) INFORMATION FOR SEQ ID NO: 1:

(i) SEQUENCE CHARACTERISTICS:
          (A) LENGTH: 367 base pairs
          (B) TYPE: nucleic acid
          (C) STRANDEDNESS: double
          (D) TOPOLOGY: linear (ii) MOLECULE TYPE: cDNA (ix) FEATURE:
          (A) NAME/KEY: CDS
          (B) LOCATION: 22..180

(xi) SEQUENCE DESCRIPTION: SEQ ID NO: 1:

GAATTCGGCT TGATCAATCG C TTC AAA AAG GGG ATC TGT CTG AGC TGC CGC          51
                        Phe Lys Lys Gly Ile Cys Leu Ser Cys Arg
                         1               5                  10

AAG AAC CGT TGT AAT AGC ATT GGC TAC AAT GCC AAG AAA ATG AGG AAC          99
Lys Asn Arg Cys Asn Ser Ile Gly Tyr Asn Ala Lys Lys Met Arg Asn
             15                  20                  25

AAG AGG AAC AGC AAA ATG TAC CTA AAA ACC CGG GCA GGC ATG CCT TTC         147
Lys Arg Asn Ser Lys Met Tyr Leu Lys Thr Arg Ala Gly Met Pro Phe
         30                  35                  40

AGA GGT AAC CTT CAG TCC CTG GAG TGT CCC TGA GGAAGGCCCT TAATACCTCC       200
Arg Gly Asn Leu Gln Ser Leu Glu Cys Pro
     45                  50

TTCTTAATAC CATGCTGCAG AGCAGGGCAC ATCCTAGCCC AGGAGAAGTG GCCAGCACAA       260

TCCAATCAAA TCGTTGCAAA TCAGATTACA CTGTGCATGT CCTAGGAAAG GGAATCTTTA       320
```

```
CAAAATAAAC AGTGTGGACC CCTCAAAAAA AAAAAAAGC CGAATTC                    367
```

(2) INFORMATION FOR SEQ ID NO: 2:

(i) SEQUENCE CHARACTERISTICS:
        (A) LENGTH: 52 amino acids
        (B) TYPE: amino acid
        (D) TOPOLOGY: linear (ii) MOLECULE TYPE: protein (xi) SEQUENCE DESCRIPTION: SEQ ID NO: 2:

```
Phe Lys Lys Gly Ile Cys Leu Ser Cys Arg Lys Asn Arg Cys Asn Ser
 1               5                  10                  15

Ile Gly Tyr Asn Ala Lys Lys Met Arg Asn Lys Arg Asn Ser Lys Met
            20                  25                  30

Tyr Leu Lys Thr Arg Ala Gly Met Pro Phe Arg Gly Asn Leu Gln Ser
        35                  40                  45

Leu Glu Cys Pro
        50
```

(2) INFORMATION FOR SEQ ID NO: 3:

(i) SEQUENCE CHARACTERISTICS:
        (A) LENGTH: 1382 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 312..1370

(xi) SEQUENCE DESCRIPTION: SEQ ID NO: 3:

```
GAATTCGGCT TCTACTACTA CTAGGCCACG CGTCGCCTAG TACGGGGGGG GGGGGGGGGG    60

TCAGCGAGTC CTTGCCTCCC GGCGGCTCAG GACGAGGGCA GATCTCGTTC TGGGGCAAGC   120

CGTTGACACT CGCTCCCTGC CACCGCCCGG GCTCCGTGCC GCCAAGTTTT CATTTTCCAC   180

CTTCTCTGCC TCCAGTCCCC CAGCCCCTGG CCGAGAGAAG GGTCTTACCG GCCGGGATTG   240

CTGGAAACAC CAAGAGGTGG TTTTTGTTTT TTAAAACTTC TGTTTCTTGG GAGGGGGTGT   300

GGCGGGGCAG G ATG AGC AAC TCC GTT CCT CTG CTC TGT TTC TGG AGC CTC   350
            Met Ser Asn Ser Val Pro Leu Leu Cys Phe Trp Ser Leu
             1               5                  10

TGC TAT TGC TTT GCT GCG GGG AGC CCC GTA CCT TTT GGT CCA GAG GGA   398
Cys Tyr Cys Phe Ala Ala Gly Ser Pro Val Pro Phe Gly Pro Glu Gly
         15                  20                  25

CGG CTG GAA GAT AAG CTC CAC AAA CCC AAA GCT ACA CAG ACT GAG GTC   446
Arg Leu Glu Asp Lys Leu His Lys Pro Lys Ala Thr Gln Thr Glu Val
 30                  35                  40                  45

AAA CCA TCT GTG AGG TTT AAC CTC CGC ACC TCC AAG GAC CCA GAG CAT   494
Lys Pro Ser Val Arg Phe Asn Leu Arg Thr Ser Lys Asp Pro Glu His
                 50                  55                  60

GAA GGA TGC TAC CTC TCC GTC GGC CAC AGC CAG CCC TTA GAA GAC TGC   542
Glu Gly Cys Tyr Leu Ser Val Gly His Ser Gln Pro Leu Glu Asp Cys
             65                  70                  75

AGT TTC AAC ATG ACA GCT AAA ACC TTT TTC ATC ATT CAC GGA TGG ACG   590
Ser Phe Asn Met Thr Ala Lys Thr Phe Phe Ile Ile His Gly Trp Thr
         80                  85                  90

ATG AGC GGT ATC TTT GAA AAC TGG CTG CAC AAA CTC GTG TCA GCC CTG   638
Met Ser Gly Ile Phe Glu Asn Trp Leu His Lys Leu Val Ser Ala Leu
```

```
CAC ACA AGA GAG AAA GAC GCC AAT GTA GTT GTG GTT GAC TGG CTC CCC        686
His Thr Arg Glu Lys Asp Ala Asn Val Val Val Val Asp Trp Leu Pro
110             115                 120                 125

CTG GCC CAC CAG CTT TAC ACG GAT GCG GTC AAT AAT ACC AGG GTG GTG        734
Leu Ala His Gln Leu Tyr Thr Asp Ala Val Asn Asn Thr Arg Val Val
                130                 135                 140

GGA CAC AGC ATT GCC AGG ATG CTC GAC TGG CTG CAG GAG AAG GAC GAT        782
Gly His Ser Ile Ala Arg Met Leu Asp Trp Leu Gln Glu Lys Asp Asp
            145                 150                 155

TTT TCT CTC GGG AAT GTC CAC TTG ATC GGC TAC AGC CTC GGA GCG CAC        830
Phe Ser Leu Gly Asn Val His Leu Ile Gly Tyr Ser Leu Gly Ala His
        160                 165                 170

GTG GCC GGG TAT GCA GGC AAC TTC GTG AAA GGA ACG GTG GGC CGA ATC        878
Val Ala Gly Tyr Ala Gly Asn Phe Val Lys Gly Thr Val Gly Arg Ile
    175                 180                 185

ACA GGT TTG GAT CCT GCC GGG CCC ATG TTT GAA GGG GCC GAC ATC CAC        926
Thr Gly Leu Asp Pro Ala Gly Pro Met Phe Glu Gly Ala Asp Ile His
190             195                 200                 205

AAG AGG CTC TCT CCG GAC GAT GCA GAT TTT GTG GAT GTC CTC CAC ACC        974
Lys Arg Leu Ser Pro Asp Asp Ala Asp Phe Val Asp Val Leu His Thr
                210                 215                 220

TAC ACG CGT TCC TTC GGC TTG AGC ATT GGT ATT CAG ATG CCT GTG GGC       1022
Tyr Thr Arg Ser Phe Gly Leu Ser Ile Gly Ile Gln Met Pro Val Gly
            225                 230                 235

CAC ATT GAC ATC TAC CCC AAT GGG GGT GAC TTC CAG CCA GGC TGT GGA       1070
His Ile Asp Ile Tyr Pro Asn Gly Gly Asp Phe Gln Pro Gly Cys Gly
        240                 245                 250

CTC AAC GAT GTC TTG GGA TCA ATT GCA TAT GGA ACA ATC ACA GAG GTG       1118
Leu Asn Asp Val Leu Gly Ser Ile Ala Tyr Gly Thr Ile Thr Glu Val
    255                 260                 265

GTA AAA TGT GAG CAT GAG CGA GCC GTC CAC CTC TTT GTT GAC TCT CTG       1166
Val Lys Cys Glu His Glu Arg Ala Val His Leu Phe Val Asp Ser Leu
270             275                 280                 285

GTG AAT CAG GAC AAG CCG AGT TTT GCC TTC CAG TGC ACT GAC TCC AAT       1214
Val Asn Gln Asp Lys Pro Ser Phe Ala Phe Gln Cys Thr Asp Ser Asn
                290                 295                 300

CGC TTC AAA AAG GGG ATC TGT CTG AGC TGC CGC AAG AAC CGT TGT AAT       1262
Arg Phe Lys Lys Gly Ile Cys Leu Ser Cys Arg Lys Asn Arg Cys Asn
            305                 310                 315

AGC ATT GGC TAC AAT GCC AAG AAA ATG AGG AAC AAG AGG AAC AGC AAA       1310
Ser Ile Gly Tyr Asn Ala Lys Lys Met Arg Asn Lys Arg Asn Ser Lys
        320                 325                 330

ATG TAC CTA AAA ACC CGG GCA GGC ATG CCT TTC AGA GGT AAC CTT CAG       1358
Met Tyr Leu Lys Thr Arg Ala Gly Met Pro Phe Arg Gly Asn Leu Gln
    335                 340                 345

TCC CTG GAG TGT CAAGCCGAAT TC                                         1382
Ser Leu Glu Cys
350
```

(2) INFORMATION FOR SEQ ID NO: 4:

(i) SEQUENCE CHARACTERISTICS:
        (A) LENGTH: 353 amino acids
        (B) TYPE: amino acid
        (D) TOPOLOGY: linear (ii) MOLECULE TYPE: protein (xi) SEQUENCE DESCRIPTION: SEQ ID NO: 4:

Met Ser Asn Ser Val Pro Leu Leu Cys Phe Trp Ser Leu Cys Tyr Cys

```
           1               5                   10                  15
       Phe Ala Ala Gly Ser Pro Val Pro Phe Gly Pro Glu Gly Arg Leu Glu
                       20                  25                  30

Asp Lys Leu His Lys Pro Lys Ala Thr Gln Thr Glu Val Lys Pro Ser
                       35                  40                  45

Val Arg Phe Asn Leu Arg Thr Ser Lys Asp Pro Glu His Glu Gly Cys
                       50                  55                  60

Tyr Leu Ser Val Gly His Ser Gln Pro Leu Glu Asp Cys Ser Phe Asn
       65                  70                  75                  80

Met Thr Ala Lys Thr Phe Phe Ile Ile His Gly Trp Thr Met Ser Gly
                       85                  90                  95

Ile Phe Glu Asn Trp Leu His Lys Leu Val Ser Ala Leu His Thr Arg
                       100                 105                 110

Glu Lys Asp Ala Asn Val Val Val Asp Trp Leu Pro Leu Ala His
                       115                 120                 125

Gln Leu Tyr Thr Asp Ala Val Asn Asn Thr Arg Val Val Gly His Ser
                       130                 135                 140

Ile Ala Arg Met Leu Asp Trp Leu Gln Glu Lys Asp Asp Phe Ser Leu
       145                 150                 155                 160

Gly Asn Val His Leu Ile Gly Tyr Ser Leu Gly Ala His Val Ala Gly
                       165                 170                 175

Tyr Ala Gly Asn Phe Val Lys Gly Thr Val Gly Arg Ile Thr Gly Leu
                       180                 185                 190

Asp Pro Ala Gly Pro Met Phe Glu Gly Ala Asp Ile His Lys Arg Leu
                       195                 200                 205

Ser Pro Asp Asp Ala Asp Phe Val Asp Val Leu His Thr Tyr Thr Arg
                       210                 215                 220

Ser Phe Gly Leu Ser Ile Gly Ile Gln Met Pro Val Gly His Ile Asp
       225                 230                 235                 240

Ile Tyr Pro Asn Gly Gly Asp Phe Gln Pro Gly Cys Gly Leu Asn Asp
                       245                 250                 255

Val Leu Gly Ser Ile Ala Tyr Gly Thr Ile Thr Glu Val Val Lys Cys
                       260                 265                 270

Glu His Glu Arg Ala Val His Leu Phe Val Asp Ser Leu Val Asn Gln
                       275                 280                 285

Asp Lys Pro Ser Phe Ala Phe Gln Cys Thr Asp Ser Asn Arg Phe Lys
                       290                 295                 300

Lys Gly Ile Cys Leu Ser Cys Arg Lys Asn Arg Cys Asn Ser Ile Gly
       305                 310                 315                 320

Tyr Asn Ala Lys Lys Met Arg Asn Lys Arg Asn Ser Lys Met Tyr Leu
                       325                 330                 335

Lys Thr Arg Ala Gly Met Pro Phe Arg Gly Asn Leu Gln Ser Leu Glu
                       340                 345                 350

Cys (2) INFORMATION FOR SEQ ID NO: 5:

(i) SEQUENCE CHARACTERISTICS:
        (A) LENGTH: 1065 base pairs
        (B) TYPE: nucleic acid
        (C) STRANDEDNESS: double
        (D) TOPOLOGY: linear (ii) MOLECULE TYPE: cDNA (ix) FEATURE:
```

(A) NAME/KEY: CDS
(B) LOCATION: 1..1065

(xi) SEQUENCE DESCRIPTION: SEQ ID NO: 5:

| | | | | | | | | | | | | | | | | |
|---|---|---|---|---|---|---|---|---|---|---|---|---|---|---|---|---|
| ATG | AGC | AAC | TCC | GTT | CCT | CTG | CTC | TGT | TTC | TGG | AGC | CTC | TGC | TAT | TGC | 48 |
| Met | Ser | Asn | Ser | Val | Pro | Leu | Leu | Cys | Phe | Trp | Ser | Leu | Cys | Tyr | Cys | |
| 1 | | | | 5 | | | | | 10 | | | | | 15 | | |
| TTT | GCT | GCG | GGG | AGC | CCC | GTA | CCT | TTT | GGT | CCA | GAG | GGA | CGG | CTG | GAA | 96 |
| Phe | Ala | Ala | Gly | Ser | Pro | Val | Pro | Phe | Gly | Pro | Glu | Gly | Arg | Leu | Glu | |
| | | | 20 | | | | | 25 | | | | | 30 | | | |
| GAT | AAG | CTC | CAC | AAA | CCC | AAA | GCT | ACA | CAG | ACT | GAG | GTC | AAA | CCA | TCT | 144 |
| Asp | Lys | Leu | His | Lys | Pro | Lys | Ala | Thr | Gln | Thr | Glu | Val | Lys | Pro | Ser | |
| | | | | 35 | | | | | 40 | | | | | 45 | | |
| GTG | AGG | TTT | AAC | CTC | CGC | ACC | TCC | AAG | GAC | CCA | GAG | CAT | GAA | GGA | TGC | 192 |
| Val | Arg | Phe | Asn | Leu | Arg | Thr | Ser | Lys | Asp | Pro | Glu | His | Glu | Gly | Cys | |
| | 50 | | | | | 55 | | | | | 60 | | | | | |
| TAC | CTC | TCC | GTC | GGC | CAC | AGC | CAG | CCC | TTA | GAA | GAC | TGC | AGT | TTC | AAC | 240 |
| Tyr | Leu | Ser | Val | Gly | His | Ser | Gln | Pro | Leu | Glu | Asp | Cys | Ser | Phe | Asn | |
| 65 | | | | | 70 | | | | | 75 | | | | | 80 | |
| ATG | ACA | GCT | AAA | ACC | TTT | TTC | ATC | ATT | CAC | GGA | TGG | ACG | ATG | AGC | GGT | 288 |
| Met | Thr | Ala | Lys | Thr | Phe | Phe | Ile | Ile | His | Gly | Trp | Thr | Met | Ser | Gly | |
| | | | | 85 | | | | | 90 | | | | | 95 | | |
| ATC | TTT | GAA | AAC | TGG | CTG | CAC | AAA | CTC | GTG | TCA | GCC | CTG | CAC | ACA | AGA | 336 |
| Ile | Phe | Glu | Asn | Trp | Leu | His | Lys | Leu | Val | Ser | Ala | Leu | His | Thr | Arg | |
| | | | | | 100 | | | | | 105 | | | | | 110 | |
| GAG | AAA | GAC | GCC | AAT | GTA | GTT | GTG | GTT | GAC | TGG | CTC | CCC | CTG | GCC | CAC | 384 |
| Glu | Lys | Asp | Ala | Asn | Val | Val | Val | Val | Asp | Trp | Leu | Pro | Leu | Ala | His | |
| | | | 115 | | | | | 120 | | | | | 125 | | | |
| CAG | CTT | TAC | ACG | GAT | GCG | GTC | AAT | AAT | ACC | AGG | GTG | GTG | GGA | CAC | AGC | 432 |
| Gln | Leu | Tyr | Thr | Asp | Ala | Val | Asn | Asn | Thr | Arg | Val | Val | Gly | His | Ser | |
| | | 130 | | | | | 135 | | | | | 140 | | | | |
| ATT | GCC | AGG | ATG | CTC | GAC | TGG | CTG | CAG | GAG | AAG | GAC | GAT | TTT | TCT | CTC | 480 |
| Ile | Ala | Arg | Met | Leu | Asp | Trp | Leu | Gln | Glu | Lys | Asp | Asp | Phe | Ser | Leu | |
| 145 | | | | | 150 | | | | | 155 | | | | | 160 | |
| GGG | AAT | GTC | CAC | TTG | ATC | GGC | TAC | AGC | CTC | GGA | GCG | CAC | GTG | GCC | GGG | 528 |
| Gly | Asn | Val | His | Leu | Ile | Gly | Tyr | Ser | Leu | Gly | Ala | His | Val | Ala | Gly | |
| | | | | 165 | | | | | 170 | | | | | 175 | | |
| TAT | GCA | GGC | AAC | TTC | GTG | AAA | GGA | ACG | GTG | GGC | CGA | ATC | ACA | GGT | TTG | 576 |
| Tyr | Ala | Gly | Asn | Phe | Val | Lys | Gly | Thr | Val | Gly | Arg | Ile | Thr | Gly | Leu | |
| | | | 180 | | | | | 185 | | | | | 190 | | | |
| GAT | CCT | GCC | GGG | CCC | ATG | TTT | GAA | GGG | GCC | GAC | ATC | CAC | AAG | AGG | CTC | 624 |
| Asp | Pro | Ala | Gly | Pro | Met | Phe | Glu | Gly | Ala | Asp | Ile | His | Lys | Arg | Leu | |
| | | 195 | | | | | 200 | | | | | 205 | | | | |
| TCT | CCG | GAC | GAT | GCA | GAT | TTT | GTG | GAT | GTC | CTC | CAC | ACC | TAC | ACG | CGT | 672 |
| Ser | Pro | Asp | Asp | Ala | Asp | Phe | Val | Asp | Val | Leu | His | Thr | Tyr | Thr | Arg | |
| 210 | | | | | 215 | | | | | 220 | | | | | | |
| TCC | TTC | GGC | TTG | AGC | ATT | GGT | ATT | CAG | ATG | CCT | GTG | GGC | CAC | ATT | GAC | 720 |
| Ser | Phe | Gly | Leu | Ser | Ile | Gly | Ile | Gln | Met | Pro | Val | Gly | His | Ile | Asp | |
| 225 | | | | | 230 | | | | | 235 | | | | | 240 | |
| ATC | TAC | CCC | AAT | GGG | GGT | GAC | TTC | CAG | CCA | GGC | TGT | GGA | CTC | AAC | GAT | 768 |
| Ile | Tyr | Pro | Asn | Gly | Gly | Asp | Phe | Gln | Pro | Gly | Cys | Gly | Leu | Asn | Asp | |
| | | | | 245 | | | | | 250 | | | | | 255 | | |
| GTC | TTG | GGA | TCA | ATT | GCA | TAT | GGA | ACA | ATC | ACA | GAG | GTG | GTA | AAA | TGT | 816 |
| Val | Leu | Gly | Ser | Ile | Ala | Tyr | Gly | Thr | Ile | Thr | Glu | Val | Val | Lys | Cys | |
| | | | 260 | | | | | 265 | | | | | 270 | | | |
| GAG | CAT | GAG | CGA | GCC | GTC | CAC | CTC | TTT | GTT | GAC | TCT | CTG | GTG | AAT | CAG | 864 |
| Glu | His | Glu | Arg | Ala | Val | His | Leu | Phe | Val | Asp | Ser | Leu | Val | Asn | Gln | |
| | | 275 | | | | | 280 | | | | | 285 | | | | |
| GAC | AAG | CCG | AGT | TTT | GCC | TTC | CAG | TGC | ACT | GAC | TCC | AAT | CGC | TTC | AAA | 912 |
| Asp | Lys | Pro | Ser | Phe | Ala | Phe | Gln | Cys | Thr | Asp | Ser | Asn | Arg | Phe | Lys | |

```
              290                 295                 300
AAG GGG ATC TGT CTG AGC TGC CGC AAG AAC CGT TGT AAT AGC ATT GGC        960
Lys Gly Ile Cys Leu Ser Cys Arg Lys Asn Arg Cys Asn Ser Ile Gly
305                 310                 315                 320

TAC AAT GCC AAG AAA ATG AGG AAC AAG AGG AAC AGC AAA ATG TAC CTA       1008
Tyr Asn Ala Lys Lys Met Arg Asn Lys Arg Asn Ser Lys Met Tyr Leu
                325                 330                 335

AAA ACC CGG GCA GGC ATG CCT TTC AGA GGT AAC CTT CAG TCC CTG GAG       1056
Lys Thr Arg Ala Gly Met Pro Phe Arg Gly Asn Leu Gln Ser Leu Glu
            340                 345                 350

TGT CCC TGA                                                           1065
Cys Pro (2) INFORMATION FOR SEQ ID NO: 6:

(i) SEQUENCE CHARACTERISTICS:
        (A) LENGTH: 354 amino acids
        (B) TYPE: amino acid
        (D) TOPOLOGY: linear (ii) MOLECULE TYPE: protein (xi) SEQUENCE DESCRIPTION: SEQ ID NO: 6:
```

Met Ser Asn Ser Val Pro Leu Leu Cys Phe Trp Ser Leu Cys Tyr Cys
 1               5                  10                  15

Phe Ala Ala Gly Ser Pro Val Pro Phe Gly Pro Glu Gly Arg Leu Glu
                20                  25                  30

Asp Lys Leu His Lys Pro Lys Ala Thr Gln Thr Glu Val Lys Pro Ser
            35                  40                  45

Val Arg Phe Asn Leu Arg Thr Ser Lys Asp Pro Glu His Glu Gly Cys
        50                  55                  60

Tyr Leu Ser Val Gly His Ser Gln Pro Leu Glu Asp Cys Ser Phe Asn
65                  70                  75                  80

Met Thr Ala Lys Thr Phe Phe Ile Ile His Gly Trp Thr Met Ser Gly
                85                  90                  95

Ile Phe Glu Asn Trp Leu His Lys Leu Val Ser Ala Leu His Thr Arg
                100                 105                 110

Glu Lys Asp Ala Asn Val Val Val Asp Trp Leu Pro Leu Ala His
            115                 120                 125

Gln Leu Tyr Thr Asp Ala Val Asn Asn Thr Arg Val Val Gly His Ser
        130                 135                 140

Ile Ala Arg Met Leu Asp Trp Leu Gln Glu Lys Asp Asp Phe Ser Leu
145                 150                 155                 160

Gly Asn Val His Leu Ile Gly Tyr Ser Leu Gly Ala His Val Ala Gly
                165                 170                 175

Tyr Ala Gly Asn Phe Val Lys Gly Thr Val Gly Arg Ile Thr Gly Leu
                180                 185                 190

Asp Pro Ala Gly Pro Met Phe Glu Gly Ala Asp Ile His Lys Arg Leu
            195                 200                 205

Ser Pro Asp Asp Ala Asp Phe Val Asp Val Leu His Thr Tyr Thr Arg
        210                 215                 220

Ser Phe Gly Leu Ser Ile Gly Ile Gln Met Pro Val Gly His Ile Asp
225                 230                 235                 240

Ile Tyr Pro Asn Gly Gly Asp Phe Gln Pro Gly Cys Gly Leu Asn Asp
                245                 250                 255

Val Leu Gly Ser Ile Ala Tyr Gly Thr Ile Thr Glu Val Val Lys Cys
                260                 265                 270

```
Glu His Glu Arg Ala Val His Leu Phe Val Asp Ser Leu Val Asn Gln
        275                 280                 285

Asp Lys Pro Ser Phe Ala Phe Gln Cys Thr Asp Ser Asn Arg Phe Lys
        290                 295                 300

Lys Gly Ile Cys Leu Ser Cys Arg Lys Asn Arg Cys Asn Ser Ile Gly
305                 310                 315                 320

Tyr Asn Ala Lys Lys Met Arg Asn Lys Arg Asn Ser Lys Met Tyr Leu
                325                 330                 335

Lys Thr Arg Ala Gly Met Pro Phe Arg Gly Asn Leu Gln Ser Leu Glu
            340                 345                 350

Cys Pro (2) INFORMATION FOR SEQ ID NO: 7:

(i) SEQUENCE CHARACTERISTICS:
        (A) LENGTH: 2565 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 252..1754

(xi) SEQUENCE DESCRIPTION: SEQ ID NO: 7:

GAATTCGCGG CCGCGTCGAC GGCGGCTCAG GACGAGGGCA GATCTCGTTC TGGGGCAAGC          60

CGTTGACACT CGCTCCCTGC CACCGCCCGG GCTCCGTGCC GCCAAGTTTT CATTTTCCAC         120

CTTCTCTGCC TCCAGTCCCC CAGCCCCTGG CCGAGAGAAG GGTCTTACCG GCCGGGATTG         180

CTGGAAACAC CAAGAGGTGG TTTTTGTTTT TTAAAACTTC TGTTTCTTGG GAGGGGGTGT         240

GGCGGGGCAG G ATG AGC AAC TCC GTT CCT CTG CTC TGT TTC TGG AGC CTC          290
             Met Ser Asn Ser Val Pro Leu Leu Cys Phe Trp Ser Leu
              1               5                  10

TGC TAT TGC TTT GCT GCG GGG AGC CCC GTA CCT TTT GGT CCA GAG GGA          338
Cys Tyr Cys Phe Ala Ala Gly Ser Pro Val Pro Phe Gly Pro Glu Gly
         15                  20                  25

CGG CTG GAA GAT AAG CTC CAC AAA CCC AAA GCT ACA CAG ACT GAG GTC          386
Arg Leu Glu Asp Lys Leu His Lys Pro Lys Ala Thr Gln Thr Glu Val
30                  35                  40                  45

AAA CCA TCT GTG AGG TTT AAC CTC CGC ACC TCC AAG GAC CCA GAG CAT          434
Lys Pro Ser Val Arg Phe Asn Leu Arg Thr Ser Lys Asp Pro Glu His
                50                  55                  60

GAA GGA TGC TAC CTC TCC GTC GGC CAC AGC CAG CCC TTA GAA GAC TGC          482
Glu Gly Cys Tyr Leu Ser Val Gly His Ser Gln Pro Leu Glu Asp Cys
            65                  70                  75

AGT TTC AAC ATG ACA GCT AAA ACC TTT TTC ATC ATT CAC GGA TGG ACG          530
Ser Phe Asn Met Thr Ala Lys Thr Phe Phe Ile Ile His Gly Trp Thr
        80                  85                  90

ATG AGC GGT ATC TTT GAA AAC TGG CTG CAC AAA CTC GTG TCA GCC CTG          578
Met Ser Gly Ile Phe Glu Asn Trp Leu His Lys Leu Val Ser Ala Leu
    95                  100                 105

CAC ACA AGA GAG AAA GAC GCC AAT GTA GTT GTG GTT GAC TGG CTC CCC          626
His Thr Arg Glu Lys Asp Ala Asn Val Val Val Val Asp Trp Leu Pro
110                 115                 120                 125

CTG GCC CAC CAG CTT TAC ACG GAT GCG GTC AAT AAT ACC AGG GTG GTG          674
Leu Ala His Gln Leu Tyr Thr Asp Ala Val Asn Asn Thr Arg Val Val
                130                 135                 140
```

```
GGA CAC AGC ATT GCC AGG ATG CTC GAC TGG CTG CAG GAG AAG GAC GAT      722
Gly His Ser Ile Ala Arg Met Leu Asp Trp Leu Gln Glu Lys Asp Asp
            145                 150                 155

TTT TCT CTC GGG AAT GTC CAC TTG ATC GGC TAC AGC CTC GGA GCG CAC      770
Phe Ser Leu Gly Asn Val His Leu Ile Gly Tyr Ser Leu Gly Ala His
        160                 165                 170

GTG GCC GGG TAT GCA GGC AAC TTC GTG AAA GGA ACG GTG GGC CGA ATC      818
Val Ala Gly Tyr Ala Gly Asn Phe Val Lys Gly Thr Val Gly Arg Ile
    175                 180                 185

ACA GGT TTG GAT CCT GCC GGG CCC ATG TTT GAA GGG GCC GAC ATC CAC      866
Thr Gly Leu Asp Pro Ala Gly Pro Met Phe Glu Gly Ala Asp Ile His
190                 195                 200                 205

AAG AGG CTC TCT CCG GAC GAT GCA GAT TTT GTG GAT GTC CTC CAC ACC      914
Lys Arg Leu Ser Pro Asp Asp Ala Asp Phe Val Asp Val Leu His Thr
                210                 215                 220

TAC ACG CGT TCC TTC GGC TTG AGC ATT GGT ATT CAG ATG CCT GTG GGC      962
Tyr Thr Arg Ser Phe Gly Leu Ser Ile Gly Ile Gln Met Pro Val Gly
            225                 230                 235

CAC ATT GAC ATC TAC CCC AAT GGG GGT GAC TTC CAG CCA GGC TGT GGA     1010
His Ile Asp Ile Tyr Pro Asn Gly Gly Asp Phe Gln Pro Gly Cys Gly
        240                 245                 250

CTC AAC GAT GTC TTG GGA TCA ATT GCA TAT GGA ACA ATC ACA GAG GTG     1058
Leu Asn Asp Val Leu Gly Ser Ile Ala Tyr Gly Thr Ile Thr Glu Val
    255                 260                 265

GTA AAA TGT GAG CAT GAG CGA GCC GTC CAC CTC TTT GTT GAC TCT CTG     1106
Val Lys Cys Glu His Glu Arg Ala Val His Leu Phe Val Asp Ser Leu
270                 275                 280                 285

GTG AAT CAG GAC AAG CCG AGT TTT GCC TTC CAG TGC ACT GAC TCC AAT     1154
Val Asn Gln Asp Lys Pro Ser Phe Ala Phe Gln Cys Thr Asp Ser Asn
                290                 295                 300

CGC TTC AAA AAG GGG ATC TGT CTG AGC TGC CGC AAG AAC CGT TGT AAT     1202
Arg Phe Lys Lys Gly Ile Cys Leu Ser Cys Arg Lys Asn Arg Cys Asn
            305                 310                 315

AGC ATT GGC TAC AAT GCC AAG AAA ATG AGG AAC AAG AGG AAC AGC AAA     1250
Ser Ile Gly Tyr Asn Ala Lys Lys Met Arg Asn Lys Arg Asn Ser Lys
        320                 325                 330

ATG TAC CTA AAA ACC CGG GCA GGC ATG CCT TTC AGA GTT TAC CAT TAT     1298
Met Tyr Leu Lys Thr Arg Ala Gly Met Pro Phe Arg Val Tyr His Tyr
    335                 340                 345

CAG ATG AAA ATC CAT GTC TTC AGT TAC AAG AAC ATG GGA GAA ATT GAG     1346
Gln Met Lys Ile His Val Phe Ser Tyr Lys Asn Met Gly Glu Ile Glu
350                 355                 360                 365

CCC ACC TTT TAC GTC ACC CTT TAT GGC ACT AAT GCA GAT TCC CAG ACT     1394
Pro Thr Phe Tyr Val Thr Leu Tyr Gly Thr Asn Ala Asp Ser Gln Thr
                370                 375                 380

CTG CCA CTG GAA ATA GTG GAG CGG ATC GAG CAG AAT GCC ACC AAC ACC     1442
Leu Pro Leu Glu Ile Val Glu Arg Ile Glu Gln Asn Ala Thr Asn Thr
            385                 390                 395

TTC CTG GTC TAC ACC GAG GAG GAC TTG GGA GAC CTC TTG AAG ATC CAG     1490
Phe Leu Val Tyr Thr Glu Glu Asp Leu Gly Asp Leu Leu Lys Ile Gln
        400                 405                 410

CTC ACC TGG GAG GGG GCC TCT CAG TCT TGG TAC AAC CTG TGG AAG GAG     1538
Leu Thr Trp Glu Gly Ala Ser Gln Ser Trp Tyr Asn Leu Trp Lys Glu
    415                 420                 425

TTT CGC AGC TAC CTG TCT CAA CCC CGC AAC CCC GGA CGG GAG CTG AAT     1586
Phe Arg Ser Tyr Leu Ser Gln Pro Arg Asn Pro Gly Arg Glu Leu Asn
430                 435                 440                 445

ATC AGG CGC ATC CGG GTG AAG TCT GGG GAA ACC CAG CGG AAA CTG ACA     1634
Ile Arg Arg Ile Arg Val Lys Ser Gly Glu Thr Gln Arg Lys Leu Thr
                450                 455                 460
```

```
TTT TGT ACA GAA GAC CCT GAG AAC ACC AGC ATA TCC CCA GGC CGG GAG      1682
Phe Cys Thr Glu Asp Pro Glu Asn Thr Ser Ile Ser Pro Gly Arg Glu
            465                 470                 475

CTC TGG TTT CGC AAG TGT CGG GAT GGC TGG AGG ATG AAA AAC GAA ACC      1730
Leu Trp Phe Arg Lys Cys Arg Asp Gly Trp Arg Met Lys Asn Glu Thr
            480                 485                 490

AGT CCC ACT GTG GAG CTT CCC TGA GGGTGCCCGG GCAAGTCTTG CCAGCAAGGC     1784
Ser Pro Thr Val Glu Leu Pro
            495             500

AGCAAGACTT CCTGCTATCC AAGCCCATGG AGGAAAGTTA CTGCTGAGGA CCCACCCAAT    1844
GGAAGGATTC TTCTCAGCCT TGACCCTGGA GCACTGGGAA CAACTGGTCT CCTGTGATGG    1904
CTGGGACTCC TCGCGGGAGG GGACTGCGCT GCTATAGCTC TTGCTGCCTC TCTTGAATAG    1964
CTCTAACTCC AAACCTCTGT CCACACCTCC AGAGCACCAA GTCCAGATTT GTGTGTAAGC    2024
AGCTGGGTGC CTGGGGCCTC TCGTGCACAC TGGATTGGTT TCTCAGTTGC TGGGCGAGCC    2084
TGTACTCTGC CTGACGAGGA ACGCTGGCTC CGAAGAGGCC CTGTGTAGAA GGCTGTCAGC    2144
TGCTCAGCCT GCTTTGAGCC TCAGTGAGAA GTCCTTCCGA CAGGAGCTGA CTCATGTCAG    2204
GATGGCAGGC CTGGTATCTT GCTCGGGCCC TGGCTGTTGG GGTTCTCATG GGTTGCACTG    2264
ACCATACTGC TTACGTCTTA GCCATTCCGT CCTGCTCCCC AGCTCACTCT CTGAAGCACA    2324
CATCATTGGC TTTCCTATTT TTCTGTTCAT TTTTTAATTG AGCAAATGTC TATTGAACAC    2384
TTAAAATTAA TTAGAATGTG GTAATGGACA TATTACTGAG CCTCTCCATT TGGAACCCAG    2444
TGGAGTTGGG ATTTCTAGAC CCTCTTTCTG TTTGGATGGT GTATGTGTAT ATGCATGGGG    2504
AAAGGCACCT GGGGCCTGGG GGAGGCTATA GGATATAAGC AGTCGACGCG GCCGCGAATT    2564
C                                                                    2565
```

(2) INFORMATION FOR SEQ ID NO: 8:

(i) SEQUENCE CHARACTERISTICS:
        (A) LENGTH: 500 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Ser Asn Ser Val Pro Leu Leu Cys Phe Trp Ser Leu Cys Tyr Cys
 1               5                  10                  15

Phe Ala Ala Gly Ser Pro Val Pro Phe Gly Pro Glu Gly Arg Leu Glu
                20                  25                  30

Asp Lys Leu His Lys Pro Lys Ala Thr Gln Thr Glu Val Lys Pro Ser
            35                  40                  45

Val Arg Phe Asn Leu Arg Thr Ser Lys Asp Pro Glu His Glu Gly Cys
        50                  55                  60

Tyr Leu Ser Val Gly His Ser Gln Pro Leu Glu Asp Cys Ser Phe Asn
 65                 70                  75                  80

Met Thr Ala Lys Thr Phe Phe Ile Ile His Gly Trp Thr Met Ser Gly
                85                  90                  95

Ile Phe Glu Asn Trp Leu His Lys Leu Val Ser Ala Leu His Thr Arg
                100                 105                 110

Glu Lys Asp Ala Asn Val Val Val Asp Trp Leu Pro Leu Ala His
            115                 120                 125

Gln Leu Tyr Thr Asp Ala Val Asn Asn Thr Arg Val Val Gly His Ser
        130                 135                 140
```

```
Ile Ala Arg Met Leu Asp Trp Leu Gln Glu Lys Asp Phe Ser Leu
145                 150                 155                 160

Gly Asn Val His Leu Ile Gly Tyr Ser Leu Gly Ala His Val Ala Gly
            165                 170                 175

Tyr Ala Gly Asn Phe Val Lys Gly Thr Val Gly Arg Ile Thr Gly Leu
            180                 185                 190

Asp Pro Ala Gly Pro Met Phe Glu Gly Ala Asp Ile His Lys Arg Leu
            195                 200                 205

Ser Pro Asp Asp Ala Asp Phe Val Asp Val Leu His Thr Tyr Thr Arg
210                 215                 220

Ser Phe Gly Leu Ser Ile Gly Ile Gln Met Pro Val Gly His Ile Asp
225                 230                 235                 240

Ile Tyr Pro Asn Gly Gly Asp Phe Gln Pro Gly Cys Gly Leu Asn Asp
                245                 250                 255

Val Leu Gly Ser Ile Ala Tyr Gly Thr Ile Thr Glu Val Val Lys Cys
            260                 265                 270

Glu His Glu Arg Ala Val His Leu Phe Val Asp Ser Leu Val Asn Gln
            275                 280                 285

Asp Lys Pro Ser Phe Ala Phe Gln Cys Thr Asp Ser Asn Arg Phe Lys
290                 295                 300

Lys Gly Ile Cys Leu Ser Cys Arg Lys Asn Arg Cys Asn Ser Ile Gly
305                 310                 315                 320

Tyr Asn Ala Lys Lys Met Arg Asn Lys Arg Asn Ser Lys Met Tyr Leu
                325                 330                 335

Lys Thr Arg Ala Gly Met Pro Phe Arg Val Tyr His Tyr Gln Met Lys
            340                 345                 350

Ile His Val Phe Ser Tyr Lys Asn Met Gly Glu Ile Glu Pro Thr Phe
            355                 360                 365

Tyr Val Thr Leu Tyr Gly Thr Asn Ala Asp Ser Gln Thr Leu Pro Leu
370                 375                 380

Glu Ile Val Glu Arg Ile Glu Gln Asn Ala Thr Asn Thr Phe Leu Val
385                 390                 395                 400

Tyr Thr Glu Glu Asp Leu Gly Asp Leu Leu Lys Ile Gln Leu Thr Trp
                405                 410                 415

Glu Gly Ala Ser Gln Ser Trp Tyr Asn Leu Trp Lys Glu Phe Arg Ser
            420                 425                 430

Tyr Leu Ser Gln Pro Arg Asn Pro Gly Arg Glu Leu Asn Ile Arg Arg
            435                 440                 445

Ile Arg Val Lys Ser Gly Glu Thr Gln Arg Lys Leu Thr Phe Cys Thr
450                 455                 460

Glu Asp Pro Glu Asn Thr Ser Ile Ser Pro Gly Arg Glu Leu Trp Phe
465                 470                 475                 480

Arg Lys Cys Arg Asp Gly Trp Arg Met Lys Asn Glu Thr Ser Pro Thr
                485                 490                 495

Val Glu Leu Pro
            500

(2) INFORMATION FOR SEQ ID NO: 9:

(i) SEQUENCE CHARACTERISTICS:
        (A) LENGTH: 1035 base pairs
        (B) TYPE: nucleic acid
        (C) STRANDEDNESS: double
        (D) TOPOLOGY: linear
```

```
    (ii) MOLECULE TYPE: cDNA (ix) FEATURE:
         (A) NAME/KEY: CDS
         (B) LOCATION: 1..1035

(xi) SEQUENCE DESCRIPTION: SEQ ID NO: 9:

ATG AGC AAC TCC GTT CCT CTG CTC TGT TTC TGG AGC CTC TGC TAT TGC    48
Met Ser Asn Ser Val Pro Leu Leu Cys Phe Trp Ser Leu Cys Tyr Cys
1               5                   10                  15

TTT GCT GCG GGG AGC CCC GTA CCT TTT GGT CCA GAG GGA CGG CTG GAA    96
Phe Ala Ala Gly Ser Pro Val Pro Phe Gly Pro Glu Gly Arg Leu Glu
                20                  25                  30

GAT AAG CTC CAC AAA CCC AAA GCT ACA CAG ACT GAG GTC AAA CCA TCT   144
Asp Lys Leu His Lys Pro Lys Ala Thr Gln Thr Glu Val Lys Pro Ser
            35                  40                  45

GTG AGG TTT AAC CTC CGC ACC TCC AAG GAC CCA GAG CAT GAA GGA TGC   192
Val Arg Phe Asn Leu Arg Thr Ser Lys Asp Pro Glu His Glu Gly Cys
        50                  55                  60

TAC CTC TCC GTC GGC CAC AGC CAG CCC TTA GAA GAC TGC AGT TTC AAC   240
Tyr Leu Ser Val Gly His Ser Gln Pro Leu Glu Asp Cys Ser Phe Asn
65                  70                  75                  80

ATG ACA GCT AAA ACC TTT TTC ATC ATT CAC GGA TGG ACG ATG AGC GGT   288
Met Thr Ala Lys Thr Phe Phe Ile Ile His Gly Trp Thr Met Ser Gly
                85                  90                  95

ATC TTT GAA AAC TGG CTG CAC AAA CTC GTG TCA GCC CTG CAC ACA AGA   336
Ile Phe Glu Asn Trp Leu His Lys Leu Val Ser Ala Leu His Thr Arg
                100                 105                 110

GAG AAA GAC GCC AAT GTA GTT GTG GTT GAC TGG CTC CCC CTG GCC CAC   384
Glu Lys Asp Ala Asn Val Val Val Val Asp Trp Leu Pro Leu Ala His
            115                 120                 125

CAG CTT TAC ACG GAT GCG GTC AAT AAT ACC AGG GTG GTG GGA CAC AGC   432
Gln Leu Tyr Thr Asp Ala Val Asn Asn Thr Arg Val Val Gly His Ser
        130                 135                 140

ATT GCC AGG ATG CTC GAC TGG CTG CAG GAG AAG GAC GAT TTT TCT CTC   480
Ile Ala Arg Met Leu Asp Trp Leu Gln Glu Lys Asp Asp Phe Ser Leu
145                 150                 155                 160

GGG AAT GTC CAC TTG ATC GGC TAC AGC CTC GGA GCG CAC GTG GCC GGG   528
Gly Asn Val His Leu Ile Gly Tyr Ser Leu Gly Ala His Val Ala Gly
                165                 170                 175

TAT GCA GGC AAC TTC GTG AAA GGA ACG GTG GGC CGA ATC ACA GGT TTG   576
Tyr Ala Gly Asn Phe Val Lys Gly Thr Val Gly Arg Ile Thr Gly Leu
                180                 185                 190

GAT CCT GCC GGG CCC ATG TTT GAA GGG GCC GAC ATC CAC AAG AGG CTC   624
Asp Pro Ala Gly Pro Met Phe Glu Gly Ala Asp Ile His Lys Arg Leu
            195                 200                 205

TCT CCG GAC GAT GCA GAT TTT GTG GAT GTC CTC CAC ACC TAC ACG CGT   672
Ser Pro Asp Asp Ala Asp Phe Val Asp Val Leu His Thr Tyr Thr Arg
        210                 215                 220

TCC TTC GGC TTG AGC ATT GGT ATT CAG ATG CCT GTG GGC CAC ATT GAC   720
Ser Phe Gly Leu Ser Ile Gly Ile Gln Met Pro Val Gly His Ile Asp
225                 230                 235                 240

ATC TAC CCC AAT GGG GGT GAC TTC CAG CCA GGC TGT GGA CTC AAC GAT   768
Ile Tyr Pro Asn Gly Gly Asp Phe Gln Pro Gly Cys Gly Leu Asn Asp
                245                 250                 255

GTC TTG GGA TCA ATT GCA TAT GGA ACA ATC ACA GAG GTG GTA AAA TGT   816
Val Leu Gly Ser Ile Ala Tyr Gly Thr Ile Thr Glu Val Val Lys Cys
                260                 265                 270

GAG CAT GAG CGA GCC GTC CAC CTC TTT GTT GAC TCT CTG GTG AAT CAG   864
Glu His Glu Arg Ala Val His Leu Phe Val Asp Ser Leu Val Asn Gln
            275                 280                 285
```

-continued

```
GAC AAG CCG AGT TTT GCC TTC CAG TGC ACT GAC TCC AAT CGC TTC AAA      912
Asp Lys Pro Ser Phe Ala Phe Gln Cys Thr Asp Ser Asn Arg Phe Lys
    290                 295                 300

AAG GGG ATC TGT CTG AGC TGC CGC AAG AAC CGT TGT AAT AGC ATT GGC      960
Lys Gly Ile Cys Leu Ser Cys Arg Lys Asn Arg Cys Asn Ser Ile Gly
305                 310                 315                 320

TAC AAT GCC AAG AAA ATG AGG AAC AAG AGG AAC AGC AAA ATG TAC CTA     1008
Tyr Asn Ala Lys Lys Met Arg Asn Lys Arg Asn Ser Lys Met Tyr Leu
                325                 330                 335

AAA ACC CGG GCA GGC ATG CCT TTC AGA                                 1035
Lys Thr Arg Ala Gly Met Pro Phe Arg
            340                 345
```

(2) INFORMATION FOR SEQ ID NO: 10:

(i) SEQUENCE CHARACTERISTICS:
        (A) LENGTH: 345 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Ser Asn Ser Val Pro Leu Leu Cys Phe Trp Ser Leu Cys Tyr Cys
1               5                   10                  15

Phe Ala Ala Gly Ser Pro Val Pro Phe Gly Pro Glu Gly Arg Leu Glu
                20                  25                  30

Asp Lys Leu His Lys Pro Lys Ala Thr Gln Thr Glu Val Lys Pro Ser
            35                  40                  45

Val Arg Phe Asn Leu Arg Thr Ser Lys Asp Pro Glu His Glu Gly Cys
        50                  55                  60

Tyr Leu Ser Val Gly His Ser Gln Pro Leu Glu Asp Cys Ser Phe Asn
65                  70                  75                  80

Met Thr Ala Lys Thr Phe Phe Ile Ile His Gly Trp Thr Met Ser Gly
                85                  90                  95

Ile Phe Glu Asn Trp Leu His Lys Leu Val Ser Ala Leu His Thr Arg
                100                 105                 110

Glu Lys Asp Ala Asn Val Val Val Asp Trp Leu Pro Leu Ala His
            115                 120                 125

Gln Leu Tyr Thr Asp Ala Val Asn Asn Thr Arg Val Val Gly His Ser
        130                 135                 140

Ile Ala Arg Met Leu Asp Trp Leu Gln Glu Lys Asp Asp Phe Ser Leu
145                 150                 155                 160

Gly Asn Val His Leu Ile Gly Tyr Ser Leu Gly Ala His Val Ala Gly
                165                 170                 175

Tyr Ala Gly Asn Phe Val Lys Gly Thr Val Gly Arg Ile Thr Gly Leu
                180                 185                 190

Asp Pro Ala Gly Pro Met Phe Glu Gly Ala Asp Ile His Lys Arg Leu
            195                 200                 205

Ser Pro Asp Asp Ala Asp Phe Val Asp Val Leu His Thr Tyr Thr Arg
        210                 215                 220

Ser Phe Gly Leu Ser Ile Gly Ile Gln Met Pro Val Gly His Ile Asp
225                 230                 235                 240

Ile Tyr Pro Asn Gly Gly Asp Phe Gln Pro Gly Cys Gly Leu Asn Asp
                245                 250                 255

Val Leu Gly Ser Ile Ala Tyr Gly Thr Ile Thr Glu Val Val Lys Cys
                260                 265                 270
```

```
Glu His Glu Arg Ala Val His Leu Phe Val Asp Ser Leu Val Asn Gln
        275                 280                 285

Asp Lys Pro Ser Phe Ala Phe Gln Cys Thr Asp Ser Asn Arg Phe Lys
        290                 295                 300

Lys Gly Ile Cys Leu Ser Cys Arg Lys Asn Arg Cys Asn Ser Ile Gly
305                 310                 315                 320

Tyr Asn Ala Lys Lys Met Arg Asn Lys Arg Asn Ser Lys Met Tyr Leu
                325                 330                 335

Lys Thr Arg Ala Gly Met Pro Phe Arg
                340             345

(2) INFORMATION FOR SEQ ID NO: 11:

(i) SEQUENCE CHARACTERISTICS:
        (A) LENGTH: 225 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..225

(xi) SEQUENCE DESCRIPTION: SEQ ID NO: 11:

CTG GGA TCC ATC GCC TAT GGC ACG ATC GCG GAG GTG GTG AAG TGC GAG      48
Leu Gly Ser Ile Ala Tyr Gly Thr Ile Ala Glu Val Val Lys Cys Glu
1               5                   10                  15

CAT GAG CGG GCC GTG CAT CTC TTT GTG GAC TCC CTG GTG AAC CAG GAC      96
His Glu Arg Ala Val His Leu Phe Val Asp Ser Leu Val Asn Gln Asp
            20                  25                  30

AAG CCG AGC TTT GCC TTC CAG TGC ACA GAC TCC AAC CGC TTC AAA AAA     144
Lys Pro Ser Phe Ala Phe Gln Cys Thr Asp Ser Asn Arg Phe Lys Lys
        35                  40                  45

GGG ATC TGT CTC AGC TGC CGG AAG AAC CGC TGT AAC GGC ATC GGC TAC     192
Gly Ile Cys Leu Ser Cys Arg Lys Asn Arg Cys Asn Gly Ile Gly Tyr
    50                  55                  60

AAT GCT AAG AAG ACG AGG AAT AAG AGG AAC ACC                         225
Asn Ala Lys Lys Thr Arg Asn Lys Arg Asn Thr
65                  70                  75

(2) INFORMATION FOR SEQ ID NO: 12:

(i) SEQUENCE CHARACTERISTICS:
        (A) LENGTH: 75 amino acids
        (B) TYPE: amino acid
        (D) TOPOLOGY: linear (ii) MOLECULE TYPE: protein (xi) SEQUENCE DESCRIPTION: SEQ ID NO: 12:

Leu Gly Ser Ile Ala Tyr Gly Thr Ile Ala Glu Val Val Lys Cys Glu
1               5                   10                  15

His Glu Arg Ala Val His Leu Phe Val Asp Ser Leu Val Asn Gln Asp
            20                  25                  30

Lys Pro Ser Phe Ala Phe Gln Cys Thr Asp Ser Asn Arg Phe Lys Lys
        35                  40                  45

Gly Ile Cys Leu Ser Cys Arg Lys Asn Arg Cys Asn Gly Ile Gly Tyr
    50                  55                  60

Asn Ala Lys Lys Thr Arg Asn Lys Arg Asn Thr
65                  70                  75
```

(2) INFORMATION FOR SEQ ID NO: 13:

(i) SEQUENCE CHARACTERISTICS:
        (A) LENGTH: 475 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 13:

```
Met Glu Ser Lys Ala Leu Leu Val Leu Thr Leu Ala Val Trp Leu Gl
 1               5                  10                  15

Ser Leu Thr Ala Ser Arg Gly Gly Val Ala Ala Ala Asp Gln Arg Ar
                20                  25                  30

Asp Phe Ile Asp Ile Glu Ser Lys Phe Ala Leu Arg Thr Pro Glu As
            35                  40                  45

Thr Ala Glu Asp Thr Cys His Leu Ile Pro Gly Val Ala Glu Ser Va
        50                  55                  60

Ala Thr Cys His Phe Asn His Ser Ser Lys Thr Phe Met Val Ile Hi
65                  70                  75                  80

Gly Trp Thr Val Thr Gly Met Tyr Glu Ser Trp Val Pro Lys Leu Va
                85                  90                  95

Ala Ala Leu Tyr Lys Arg Glu Pro Asp Ser Asn Val Ile Val Val As
                100                 105                 110

Trp Leu Ser Arg Ala Gln Glu His Tyr Pro Val Ser Ala Gly Tyr Th
            115                 120                 125

Lys Leu Val Gly Gln Asp Val Ala Arg Phe Ile Asn Trp Met Glu Gl
        130                 135                 140

Glu Phe Asn Tyr Pro Leu Asp Asn Val His Leu Leu Gly Tyr Ser Le
145                 150                 155                 160

Gly Ala His Ala Ala Gly Ile Ala Gly Ser Leu Thr Asn Lys Lys Va
                165                 170                 175

Asn Arg Ile Thr Gly Leu Asp Pro Ala Gly Pro Asn Phe Glu Tyr Al
            180                 185                 190

Glu Ala Pro Ser Arg Leu Ser Pro Asp Asp Ala Asp Phe Val Asp Va
        195                 200                 205

Leu His Thr Phe Thr Arg Gly Ser Pro Gly Arg Ser Ile Gly Ile Gl
210                 215                 220

Lys Pro Val Gly His Val Asp Ile Tyr Pro Asn Gly Gly Thr Phe Gl
225                 230                 235                 240

Pro Gly Cys Asn Ile Gly Glu Ala Ile Arg Val Ile Ala Glu Arg Gl
                245                 250                 255

Leu Gly Asp Val Asp Gln Leu Val Lys Cys Ser His Glu Arg Ser Il
            260                 265                 270

His Leu Phe Ile Asp Ser Leu Leu Asn Glu Glu Asn Pro Ser Lys Al
        275                 280                 285

Tyr Arg Cys Ser Ser Lys Glu Ala Phe Glu Lys Gly Leu Cys Leu Se
        290                 295                 300

Cys Arg Lys Asn Arg Cys Asn Asn Leu Gly Tyr Glu Ile Asn Lys Va
305                 310                 315                 320

Arg Ala Lys Arg Ser Ser Lys Met Tyr Leu Lys Thr Arg Ser Gln Me
                325                 330                 335

Pro Tyr Lys Val Phe His Tyr Gln Val Lys Ile His Phe Ser Gly Th
                340                 345                 350
```

```
Glu Ser Glu Thr His Thr Asn Gln Ala Phe Glu Ile Ser Leu Tyr Gl
            355                 360                 365

Thr Val Ala Glu Ser Glu Asn Ile Pro Phe Thr Leu Pro Glu Val Se
        370                 375                 380

Thr Asn Lys Thr Tyr Ser Phe Leu Ile Tyr Thr Glu Val Asp Ile Gl
385                 390                 395                 400

Glu Leu Leu Met Leu Lys Leu Lys Trp Lys Ser Asp Ser Tyr Phe Se
                405                 410                 415

Trp Ser Asp Trp Trp Ser Ser Pro Gly Phe Ala Ile Gln Lys Ile Ar
            420                 425                 430

Val Lys Ala Gly Glu Thr Gln Lys Lys Val Ile Phe Cys Ser Arg Gl
            435                 440                 445

Lys Val Ser His Leu Gln Lys Gly Lys Ala Pro Ala Val Phe Val Ly
            450                 455                 460

Cys His Asp Lys Ser Leu Asn Lys Lys Ser Gly
465                 470                 475

(2) INFORMATION FOR SEQ ID NO: 14:

(i) SEQUENCE CHARACTERISTICS:
          (A) LENGTH: 499 amino acids
          (B) TYPE: amino acid
          (C) STRANDEDNESS:
          (D) TOPOLOGY: linear (ii) MOLECULE TYPE: protein (xi) SEQUENCE DESCRIPTION: SEQ ID NO: 14:

Met Asp Thr Ser Pro Leu Cys Phe Ser Ile Leu Leu Val Leu Cys Il
1               5                   10                  15

Phe Ile Gln Ser Ser Ala Leu Gly Gln Ser Leu Lys Pro Glu Pro Ph
                20                  25                  30

Gly Arg Arg Ala Gln Ala Val Glu Thr Asn Lys Thr Leu His Glu Me
            35                  40                  45

Lys Thr Arg Phe Leu Leu Phe Gly Glu Thr Asn Gln Gly Cys Gln Il
    50                  55                  60

Arg Ile Asn His Pro Asp Thr Leu Gln Glu Cys Gly Phe Asn Ser Se
65                  70                  75                  80

Leu Pro Leu Val Met Ile Ile His Gly Trp Ser Val Asp Gly Val Le
                85                  90                  95

Glu Asn Trp Ile Trp Gln Met Val Ala Ala Leu Lys Ser Gln Pro Al
                100                 105                 110

Gln Pro Val Asn Val Gly Leu Val Asp Trp Ile Thr Leu Ala His As
            115                 120                 125

His Tyr Thr Ile Ala Val Arg Asn Thr Arg Leu Val Gly Lys Glu Va
            130                 135                 140

Ala Ala Leu Leu Arg Trp Leu Glu Glu Ser Val Gln Leu Ser Arg Se
145                 150                 155                 160

His Val His Leu Ile Gly Tyr Ser Leu Gly Ala His Val Ser Gly Ph
                165                 170                 175

Ala Gly Ser Ser Ile Gly Gly Thr His Lys Ile Gly Arg Ile Thr Gl
            180                 185                 190

Leu Asp Ala Ala Gly Pro Leu Phe Glu Gly Ser Ala Pro Ser Asn Ar
            195                 200                 205

Leu Ser Pro Asp Asp Ala Asn Phe Val Asp Ala Ile His Thr Phe Th
            210                 215                 220
```

```
Arg Glu His Met Gly Leu Ser Val Gly Ile Lys Gln Pro Ile Gly Hi
225                 230                 235                 240

Tyr Asp Phe Tyr Pro Asn Gly Gly Ser Phe Gln Pro Gly Cys His Ph
                245                 250                 255

Leu Glu Leu Tyr Arg His Ile Ala Gln His Gly Phe Asn Ala Ile Th
                260                 265                 270

Gln Thr Ile Lys Cys Ser His Glu Arg Ser Val His Leu Phe Ile As
            275                 280                 285

Ser Leu Leu His Ala Gly Thr Gln Ser Met Ala Tyr Pro Cys Gly As
290                 295                 300

Met Asn Ser Phe Ser Gln Gly Leu Cys Leu Ser Cys Lys Lys Gly Ar
305                 310                 315                 320

Cys Asn Thr Leu Gly Tyr His Val Arg Gln Glu Pro Arg Ser Lys Se
                325                 330                 335

Lys Arg Leu Phe Leu Val Thr Arg Ala Gln Ser Pro Phe Lys Val Ty
                340                 345                 350

His Tyr Gln Leu Lys Ile Gln Phe Ile Asn Gln Thr Glu Thr Pro Il
                355                 360                 365

Gln Thr Thr Phe Thr Met Ser Leu Leu Gly Thr Lys Glu Lys Met Gl
370                 375                 380

Lys Ile Pro Ile Thr Leu Gly Lys Gly Ile Ala Ser Asn Lys Thr Ty
385                 390                 395                 400

Ser Phe Leu Ile Thr Leu Asp Val Asp Ile Gly Glu Leu Ile Met Il
                405                 410                 415

Lys Phe Lys Trp Glu Asn Ser Ala Val Trp Ala Asn Val Trp Asp Th
                420                 425                 430

Val Gln Thr Ile Ile Pro Trp Ser Thr Gly Pro Arg His Ser Gly Le
                435                 440                 445

Val Leu Lys Thr Ile Arg Val Lys Ala Gly Glu Thr Gln Gln Arg Me
450                 455                 460

Thr Phe Cys Ser Glu Asn Thr Asp Asp Leu Leu Leu Arg Pro Thr Gl
465                 470                 475                 480

Glu Lys Ile Phe Val Lys Cys Glu Ile Lys Ser Lys Thr Ser Lys Ar
                485                 490                 495

Lys Ile Arg (2) INFORMATION FOR SEQ ID NO: 15:

(i) SEQUENCE CHARACTERISTICS:
        (A) LENGTH: 465 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 15:

Met Leu Pro Leu Trp Thr Leu Ser Leu Leu Gly Ala Val Ala Gl
1               5                   10                  15

Lys Glu Val Cys Tyr Glu Arg Leu Gly Cys Phe Ser Asp Asp Ser Pr
                20                  25                  30

Trp Ser Gly Ile Thr Glu Arg Pro Leu His Ile Leu Pro Trp Ser Pr
                35                  40                  45

Lys Asp Val Asn Thr Arg Phe Leu Leu Tyr Thr Asn Glu Asn Pro As
50                  55                  60
```

```
Asn Phe Gln Glu Val Ala Ala Asp Ser Ser Ile Ser Gly Ser As
 65                  70                  75                  80

Phe Lys Thr Asn Arg Lys Thr Arg Phe Ile Ile His Gly Phe Ile As
                 85                  90                  95

Lys Gly Glu Glu Asn Trp Leu Ala Asn Val Cys Lys Asn Leu Phe Ly
            100                 105                 110

Val Glu Ser Val Asn Cys Ile Cys Val Asp Trp Lys Gly Gly Ser Ar
        115                 120                 125

Thr Gly Tyr Thr Gln Ala Ser Gln Asn Ile Arg Ile Val Gly Ala Gl
    130                 135                 140

Val Ala Tyr Phe Val Glu Phe Leu Gln Ser Ala Phe Gly Tyr Ser Pr
145                 150                 155                 160

Ser Asn Val His Val Ile Gly His Ser Leu Gly Ala His Ala Ala Gl
                165                 170                 175

Glu Ala Gly Arg Arg Thr Asn Gly Thr Ile Gly Arg Ile Thr Gly Le
            180                 185                 190

Asp Pro Ala Glu Pro Cys Phe Gln Gly Thr Pro Glu Leu Val Arg Le
        195                 200                 205

Asp Pro Ser Asp Ala Lys Phe Val Asp Val Ile His Thr Asp Gly Al
    210                 215                 220

Pro Ile Val Pro Asn Leu Gly Phe Gly Met Ser Gln Val Val Gly Hi
225                 230                 235                 240

Leu Asp Phe Phe Pro Asn Gly Gly Val Glu Met Pro Gly Cys Lys Ly
                245                 250                 255

Asn Ile Leu Ser Gln Ile Val Asp Ile Asp Gly Ile Trp Glu Gly Th
            260                 265                 270

Arg Asp Phe Ala Ala Cys Asn His Leu Arg Ser Tyr Lys Tyr Tyr Th
        275                 280                 285

Asp Ser Ile Val Asn Pro Asp Gly Phe Ala Gly Phe Pro Cys Ala Se
    290                 295                 300

Tyr Asn Val Phe Thr Ala Asn Lys Cys Phe Pro Cys Pro Ser Gly Gl
305                 310                 315                 320

Cys Pro Gln Met Gly His Tyr Ala Asp Arg Tyr Pro Gly Lys Thr As
                325                 330                 335

Asp Val Gly Gln Lys Phe Tyr Leu Asp Thr Gly Asp Ala Ser Asn Ph
            340                 345                 350

Ala Arg Trp Arg Tyr Lys Val Ser Val Thr Leu Ser Gly Lys Lys Va
        355                 360                 365

Thr Gly His Ile Leu Val Ser Leu Phe Gly Asn Lys Gly Asn Ser Ly
    370                 375                 380

Gln Tyr Glu Ile Phe Lys Gly Thr Leu Lys Pro Asp Ser Thr His Se
385                 390                 395                 400

Asn Glu Phe Asp Ser Asp Val Asp Val Gly Asp Leu Gln Met Val Ly
                405                 410                 415

Phe Ile Trp Tyr Asn Asn Val Ile Asn Pro Thr Leu Pro Arg Val Gl
            420                 425                 430

Ala Ser Lys Ile Ile Val Glu Thr Asn Val Gly Lys Gln Phe Asn Ph
        435                 440                 445

Cys Ser Pro Glu Thr Val Arg Glu Glu Val Leu Leu Thr Leu Thr Pr
    450                 455                 460

Cys
465
```

(2) INFORMATION FOR SEQ ID NO: 16:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 16:

Gly Pro Glu Gly Arg Leu Glu Asp Lys Leu His Lys Pro Lys Ala Th
1               5                   10                  15
Cys (2) INFORMATION FOR SEQ ID NO: 17:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 17:

TTTTTTTTTT TGA                                                13

(2) INFORMATION FOR SEQ ID NO: 18:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 18:

GATCAATCGC                                                    10

(2) INFORMATION FOR SEQ ID NO: 19:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 19:

TAGGACATGC ACAGTGTAAT CTG                                     23

(2) INFORMATION FOR SEQ ID NO: 20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

```
        (xi) SEQUENCE DESCRIPTION: SEQ ID NO: 20:

GATTGTGCTG GCCACTTCTC                                                        20

(2) INFORMATION FOR SEQ ID NO: 21:

(i) SEQUENCE CHARACTERISTICS:
             (A) LENGTH: 19 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "Oligonucleotide"

(xi) SEQUENCE DESCRIPTION: SEQ ID NO: 21:

GACACTCCAG GGACTGAAG                                                         19

(2) INFORMATION FOR SEQ ID NO: 22:

(i) SEQUENCE CHARACTERISTICS:
             (A) LENGTH: 48 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "Oligonucleotide"

(ix) FEATURE:
             (A) NAME/KEY: modified_base
             (B) LOCATION: 36
             (D) OTHER INFORMATION: /mod_base= i (ix) FEATURE:
             (A) NAME/KEY: modified_base
             (B) LOCATION: 37
             (D) OTHER INFORMATION: /mod_base= i (ix) FEATURE:
             (A) NAME/KEY: modified_base
             (B) LOCATION: 41
             (D) OTHER INFORMATION: /mod_base= i (ix) FEATURE:
             (A) NAME/KEY: modified_base
             (B) LOCATION: 42
             (D) OTHER INFORMATION: /mod_base= i (ix) FEATURE:
             (A) NAME/KEY: modified_base
             (B) LOCATION: 46
             (D) OTHER INFORMATION: /mod_base= i (ix) FEATURE:
             (A) NAME/KEY: modified_base
             (B) LOCATION: 47
             (D) OTHER INFORMATION: /mod_base= i (xi) SEQUENCE DESCRIPTION: SEQ ID NO: 22:

CUACUACUAC UAGGCCACGC GTCGACTAGT ACGGGNNGGG NNGGGNNG                         48

(2) INFORMATION FOR SEQ ID NO: 23:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "Oligonucleotide"

(xi) SEQUENCE DESCRIPTION: SEQ ID NO: 23:
```

```
CACACACAGG CCACGCGTCG ACTAGTAC                                        28
```

(2) INFORMATION FOR SEQ ID NO: 24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 24:

```
ACCACCATGG AGAGCAAAGC CCTG                                            24
```

(2) INFORMATION FOR SEQ ID NO: 25:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 25:

```
CCAGTTTCAG CCTGACTTCT TATTC                                           25
```

(2) INFORMATION FOR SEQ ID NO: 26:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 26:

```
GGCTGTGGAC TCAACGATGT C                                               21
```

(2) INFORMATION FOR SEQ ID NO: 27:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 27:

```
CCGGGTGGGT AGGTACATTT TG                                              22
```

(2) INFORMATION FOR SEQ ID NO: 28:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

-continued (xi) SEQUENCE DESCRIPTION: SEQ ID NO: 28:

GGGGGTGACT TCCAGCCAGG CTGTG                                              25

(2) INFORMATION FOR SEQ ID NO: 29:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 29:

AACTCTGAAA GGCATGCCTG CCCGG                                              25

(2) INFORMATION FOR SEQ ID NO: 30:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 30:

TGAAGGTCGG AGTCAACGGA TTTGGT                                             26

(2) INFORMATION FOR SEQ ID NO: 31:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 31:

CATGTGGGCC ATGAGGTCCA CCAC                                               24

ANTIBODIES AGAINST LLG POLYPEPTIDES OF THE TRIACYLGLYCEROL LIPASE FAMILY

This application is a division of U.S. application Ser. No. 10/128,449 (now U.S. Pat. No. 7,056,720), filed Apr. 23, 2002, which in turn, in a division of U.S. application Ser. No. 08/985,492 (now U.S. Pat. No. 6,395,530), filed Dec. 5, 1997, which claims the benefit of the filing date of U.S. provisional Application Nos. 60/032,254 and 60/032,783, each of which was filed on Dec. 6, 1996, the disclosures of each of the aforementioned applications being incorporated herein by reference in their entirety.

FIELD OF THE INVENTION

This invention relates to polypeptides of the triacylglycerol lipase family, to nucleic acids encoding said polypeptides, to antisense sequences derived from said nucleic acids, and to antibodies against said polypeptides. This invention also relates to the preparation of said polypeptides using recombinant technology, and to the use of said polypeptides to screen for agonists and or antagonists of said polypeptides. This invention also relates to methods for the therapeutic use of such polypeptides, and of the nucleic acid sequences encoding the same in pharmaceutical, including gene therapeutic, compositions for the treatment of disorders of lipid and lipoprotein metabolism.

BACKGROUND OF THE INVENTION

A) Lipids

Lipids are water-insoluble organic biomolecules, which are essential components of diverse biological functions, including the storage, transport, and metabolism of energy, and membrane structure and fluidity. Lipids are derived from two sources in man and other animals: some lipids are ingested as dietary fats and oils and other lipids are biosynthesized by the human or animal. In mammals at least 10% of the body weight is lipid, the bulk of which is in the form of triacylglycerols.

Triacylglycerols, also known as triglycerides and triacylglycerides, are made up of three fatty acids esterified to glycerol. Dietary triacylglycerols are stored in adipose tissues as a source of energy, or hydrolyzed in the digestive tract by triacylglycerol lipases, the most important of which is pancreatic lipase. Triacylglycerols are transported between tissues in the form of lipoproteins.

Lipoproteins are micelle-like assemblies found in plasma which contain varying proportions of different types of lipids and proteins (called apoproteins). There are five main classes of plasma lipoproteins, the major function of which is lipid transport. These classes are, in order of increasing density, chylomicrons, very low density lipoproteins (VLDL), intermediate-density lipoproteins (IDL), low density lipoproteins (LDL), and high density lipoproteins (HDL). Although many types of lipid are found associated with each lipoprotein class, each class transports predominantly one type of lipid: triacylglycerols described above are transported in chylomicrons, VLDL, and IDL; while phospholipids and cholesterol esters are transported in HDL and LDL respectively.

Phospholipids are di-fatty acid esters of glycerol phosphate, also containing a polar group coupled to the phosphate. Phospholipids are important structural components of cellular membranes. Phospholipids are hydrolyzed by enzymes called phospholipases. Phosphatidylcholine, an exemplary phospholipid, is a major component of most eukaryotic cell membranes.

Cholesterol is the metabolic precursor of steroid hormones and bile acids as well as an essential constituent of cell membranes. In man and other animals, cholesterol is ingested in the diet and also synthesized by the liver and other tissues. Cholesterol is transported between tissues in the form of cholesteryl esters in LDLs and other lipoproteins.

Membranes surround every living cell, and serve as a barrier between the intracellular and extracellular compartments. Membranes also enclose the eukaryotic nucleus, make up the endoplasmic reticulum, and serve specialized functions such as in the myelin sheath that surrounds axons. A typical membrane contains about 40% lipid and 60% protein, but there is considerable variation. The major lipid components are phospholipids, specifically phosphatidylcholine and phosphatidylethanolamine, and cholesterol. The physicochemical properties of membranes, such as fluidity, can be changed by modification of either the fatty acid profiles of the phospholipids or the cholesterol content. Modulating the composition and organization of membrane Lipids also modulates membrane-dependent cellular functions, such as receptor activity, endocytosis, and cholesterol flux.

B) Enzymes

The triacylglycerol lipases are a family of enzymes which play several pivotal roles in the metabolism of lipids in the body. Three members of the human triacylglycerol lipase family have been described: pancreatic lipase, lipoprotein lipase, and hepatic lipase (Goldberg, I. J., Le, N.-A., Ginsberg, H. N., Krauss, R. M., and Lindgren, F. T. (1988) J. Clin. Invest. 81, 561-568; Goldberg, I. J., Le, N., Paterniti J. R., Ginsberg, H. N., Lindgren, F. T., and Brown, W. V. (1982) J. Clin. Invest. 70, 1184-1192; Hide, W. A., Chan, L., and Li, W.-H. (1992) J. Lipid. Res. 33, 167-178). Pancreatic lipase is primarily responsible for the hydrolysis of dietary lipids. Variants of pancreatic lipase have been described, but their physiological role has not been determined (Giller, T., Buchwald, P., Blum-Kaelin, D., and Hunziker, W. (1992) J. Biol. Chem. 267, 16509-16516). Lipoprotein lipase is the major enzyme responsible for the distribution and utilization of triglycerides in the body. Lipoprotein lipase hydrolyzes triglycerides in both chylomicrons and VLDL. Hepatic lipase hydrolyzes triglycerides in IDL and HDL, and is responsible for lipoprotein remodeling. Hepatic lipase also functions as a phospholipase, and hydrolyzes phospholipids in HDL.

Phospholipases play important roles in the catabolism and remodeling of the phospholipid component of lipoproteins and the phospholipids of membranes. Phospholipases also play a role in the release of arachidonic acid and the subsequent formation of prostaglandins, leukotrienes, and other lipids which are involved in a variety of inflammatory processes.

The lipase polypeptides encoded by these lipase genes are approximately 450 amino acids in length with leader signal peptides to facilitate secretion. The lipase proteins are comprised of two principal domains (Winkler, K., D'Arcy, A., and Hunziker, W. (1990) Nature 343, 771-774). The amino terminal domain contains the catalytic site while the carboxyl domain is believed to be responsible for substrate binding, cofactor association, and interaction with cell receptors (Wong, H., Davis, R. C., Nikazy, J., Seebart, K. E., and Schotz, M. C. (1991) Proc. Natl. Acad. Sci. USA 88, 11290-11294; van Tilbeurgh, H., Roussel, A., Lalouel, J.-M., and Cambillau, C. (1994) J. Biol. Chem. 269, 4626-4633; Wong, H., Davis, R. C., Thuren, T., Goers, J. W., Nikazy, J., Waite, M. and Schotz, M. C. (1994) J. Biol. Chem. 269, 10319-10323; Chappell, D. A., Inoue, I., Fry, G. L., Pladet, M. W., Bowen, S. L., Iverius, P.-H., Lalouel, J.-M., and Strickland, D. K. (1994) J. Biol. Chem. 269, 18001-18006). The overall level of amino acid homology between members of the family is 22-65%, with local regions of high homology corresponding to structural homologies which are linked to enzymatic function.

The naturally occurring lipoprotein lipase protein is glycosylated, and glycosylation is necessary for LPL enzymatic activity (Semenkovich, C. F., Luo, C.-C., Nakanishi, M. K., Chen, S.-H., Smith, L C., and Chan L. (1990) J. Biol. Chem. 265, 5429-5433). There are two sites for N-linked glycosylation in hepatic and lipoprotein lipase and one in pancreatic lipase. Additionally, four sets of cysteines form disulfide bridges which are essential in maintaining structural integrity for enzymatic activity (Lo, J.-Y., Smith, L. C., and Chan, L. (1995) Biochem. Biophys. Res. Commun. 206, 266-271; Brady, L., Brzozowski, A. M., Derewenda, Z. S., Dodson, E., Dodson G., Tolley, S., Turkenburg, J. P., Christiansen, L., Huge-Jensen B., Norskov, L., Thim, L., and Menge, U. (1990) Nature 343, 767-770).

Members of the triacylglycerol lipase family share a number of conserved structural features. One such feature is the "GXSXG" motif, in which the central serine residue is one of the three residues comprising the "catalytic triad" (Winkler, K., D'Arcy, A., and Hunziker, W. (1990) Nature 343, 771-774; Faustinella, F., Smith, L. C., and Chan, L. (1992) Biochemistry 31, 7219-7223). Conserved aspartate and histidine residues make up the balance of the catalytic triad. A short span of 19-23 amino acids (the "lid region") forms an amphipathic helix structure and covers the catalytic pocket of the enzyme (Winkler, K., D'Arcy, A., and Hunziker, W. (1990) Nature 343, 771-774). This region diverges between members of the family, and it has recently been determined that the span confers substrate specificity to the enzymes (Dugi, K. A., Dichek H. L., and Santamarina-Fojo, S. (1995) J. Biol. Chem. 270, 25396-25401). Comparisons between hepatic and lipoprotein lipase have demonstrated that differences in triacylglycerol lipase and phospholipase activities of the enzymes are in part mediated by this lid region (Dugi, K. A., Dichek H. L., and Santamarina-Fojo, S. (1995) J. Biol. Chem. 270, 25396-25401).

The triacylglycerol lipases possess varying degrees of heparin binding activity. Lipoprotein lipase has the highest affinity for heparin, and this binding activity has been mapped to stretches of positively charged residues in the amino terminal domain (Ma, Y., Henderson, H. E., Liu, M.-S., Zhang, H., Forsythe, I. J., Clarke-Lewis, I., Hayden, M. R., and Brunzell, J. D. J. Lipid Res. 35, 2049-2059). The localization of lipoprotein lipase to the endothelial surface (Cheng, C. F., Oosta, G. M., Bensadoun, A., and Rosenberg, R. D. (1981) J. Biol. Chem. 256, 12893-12896) is primarily mediated through binding to surface proteoglycans (Shimada K., Gill, P. J., Silbert, J. E., Douglas, W. H. J., and Fanburg, B. L. (1981) J. Clin. Invest. 68, 995-1002; Saxena, U., Klein, M. G., and Goldberg, I. J. (1991) J. Biol. Chem. 266, 17516-17521; Eisenberg, S., Sehayek, E., Olivecrona, T., and Vlodavsky, I. (1992) J. Clin Invest. 90, 2013-2021). It is this binding activity which allows the enzyme to accelerate LDL uptake by acting as a bridge between LDL and the cell surface (Mulder, M., Lombardi, P., Jansen, H., vanBerkel T. J., Frants R. R., and Havekes, L. M. (1992) Biochem. Biophys. Res. Comm. 185, 582-587; Rutledge, J. C., and Goldberg, I. J., (1994) J. Lipid Res. 35. 1152-1160; Tsuchiya, S., Yamabe, M., Yamaguchi, T., Kobayashi, Y., Konno, T., and Tada, K (1980) Int. J. Cancer 26, 171-176).

Lipoprotein lipase and hepatic lipase are both known to function in conjunction with co-activator proteins: apolipoprotein CII for lipoprotein lipase and colipase for pancreatic lipase.

The genetic sequences encoding human pancreatic lipase, hepatic lipase and lipoprotein lipase have been reported (Genbank accession #M93285, #J03540, and #M15856 respectively). The messenger RNAs of human hepatic lipase and pancreatic lipase are approximately 1.7 and 1.8 kilobases in length respectively. Two mRNA transcripts of 3.6 and 3.2 kilobases are produced from the human lipoprotein lipase gene. These two transcripts utilize alternate polyadenylation signals, and differ in their translational efficiency (Ranganathan, G., Ong, J. M., Yukht, A., Saghizadeh, M., Simsolo, R. B., Pauer, A., and Kern, P. A. (1995) J. Biol. Chem. 270, 7149-7155).

C) Physiological Processes

The metabolism of lipids involves the interaction of lipids, apoproteins, lipoproteins, and enzymes.

Hepatic lipase and lipoprotein lipase are multifunctional proteins which mediate the binding, uptake, catabolism, and remodeling of lipoproteins and phospholipids. Lipoprotein lipase and hepatic lipase function while bound to the luminal surface of endothelial cells in peripheral tissues and the liver respectively. Both enzymes participate in reverse cholesterol transport, which is the movement of cholesterol from peripheral tissues to the liver either for excretion from the body or for recycling. Genetic defects in both hepatic lipase and lipoprotein lipase are known to be the cause of familial disorders of lipoprotein metabolism. Defects in the metabolism of lipoproteins result in serious metabolic disorders, including hypercholesterolemia, hyperlipidemia, and atherosclerosis.

Atherosclerosis is a complex, polygenic disease which is defined in histological terms by deposits (lipid or fibrolipid plaques) of lipids and of other blood derivatives in blood vessel walls, especially the large arteries (aorta, coronary arteries, carotid). These plaques, which are more or less calcified according to the degree of progression of the atherosclerotic process, may be coupled with lesions and are associated with the accumulation in the vessels of fatty deposits consisting essentially of cholesterol esters. These plaques are accompanied by a thickening of the vessel wall, hypertrophy of the smooth muscle, appearance of foam cells (lipid-laden cells resulting from uncontrolled uptake of cholesterol by recruited macrophages) and accumulation of fibrous tissue. The atheromatous plaque protrudes markedly from the wall, endowing it with a stenosing character responsible for vascular occlusions by atheroma, thrombosis or embolism, which occur in those patients who are most affected. These lesions can lead to serious cardiovascular pathologies such as infarction, sudden death, cardiac insufficiency, and stroke.

The role of triacylglycerol lipases in vascular pathologies such as atherosclerosis has been an area of intense study (reviewed in Olivecrona, G., and Olivecrona, T. (1995) Curr. Opin. Lipid. 6, 291-305). Generally, the action of the triacylglycerol lipases is believed to be antiatherogenic because these enzymes lower serum triacylglycerol levels and promote HDL formation. Transgenic animals expressing human lipoprotein lipase or hepatic lipase have decreased levels of plasma triglycerides and an increased level of high density lipoprotein (HDL) (Shimada, M., Shimano, H., Gotoda, T., Yamamoto, K., Kawamura, M., Inaba, T., Yazaki, t., and Yamada, N. (1993) J. Biol. Chem. 268, 17924-17929; Liu, M.-S., Jirik, F. R., LeBoeuf, R. C., Henderson, H., Castellani, L. W., Lusis, A. J., ma, Y., Forsythe, I. J., Zhang, H., Kirk, E., Brunzell, J. D., and Hayden, M. R. (1994) J. Biol. Chem. 269, 11417-11424). Humans with genetic defects resulting in decreased levels of lipoprotein lipase activity have been found to have hypertriglyceridemia but no increased risk of coronary heart disease. This is reported to be due to the lack of production of intermediate-sized, atherogenic lipoproteins which could accumulate within the subendothelial space (Zilversmit, D. B. (1973) Circ. Res. 33, 633-638).

In the localized area of an atherosclerotic lesion, however, the increased level of lipase activity is hypothesized to accelerate the atherogenic process (Zilversmit, D. B. (1995) Clin. Chem. 41, 153-158; Zambon, A., Torres, A., Bijvoet, S., Gagne, C., Moojani, S., Lupien, P. J., Hayden M. R., and Brunzell, J. D. (1993) Lancet 341, 1119-1121). This may be due to an increase in the binding and uptake of lipoproteins by vascular tissue mediated by lipases (Eisenberg, S., Sehayek, E., Olivecrona, T. Vlodavsky, I. (1992) J. Clin. Invest. 90, 2013-2021; Tabas, I., Li, I., Brocia R. W., Xu, S. W., Swenson T. L. Williams, K. J. (1993) J. Biol. Chem. 268, 20419-20432; Nordestgaard, B. G., and Nielsen, A. G. (1994) Curr. Opin. Lipid. 5, 252-257; Williams, K. J., and Tabas, I. (1995) Art. Thromb. and Vasc. Biol. 15, 551-561). Additionally, a high local level of lipase activity may result in cytotoxic levels of fatty acids and lysophosphatidylcholine being produced in precursors of atherosclerotic lesions.

Despite the understanding that has evolved regarding the role of lipase activity in lipid homeostasis, there nevertheless is a need in the art to identify additional genes coding for proteins that regulate lipid metabolism.

SUMMARY OF THE INVENTION

The present invention relates to the discovery of a lipase like gene (LLG), its expressed polypeptide products, and compositions and methods for their use. The LLG polypeptide binds heparin, has homology to human lipoprotein lipase and hepatic lipase, and comprises a 39 kD catalytic domain of the triacylglycerol lipase family. In a further embodiment, the polypeptide has phospholipase A activity.

This invention provides an isolated polypeptide comprising the sequence SEQ ID NO: 10.

This invention further provides an isolated polypeptide comprising the sequence SEQ ID NO: 8 and having an apparent molecular weight of about 55 kD or 68 kD on a 10% SDS-PAGE gel.

This invention also provides an isolated polypeptide comprising the sequence SEQ ID NO: 6 and having an apparent molecular weight of about 40 kD on a 10% SDS-PAGE gel.

The invention further provides an antigenic fragment of the LLG polypeptide.

Another aspect of this invention is an isolated nucleic acid encoding a polypeptide having the aforesaid sequence.

Another aspect of this invention is a vector comprising the aforesaid nucleic acid encoding said polypeptide operably linked to a regulatory region, such as a promoter.

Another aspect of this invention is a recombinant cell comprising the above-described vector.

Another aspect of this invention is a method of preparing a polypeptide which comprises culturing recombinant cells containing said polypeptide encoding nucleic acid under conditions permitting the expression of said polypeptide.

Another aspect of this invention is an antibody which is capable of specifically binding to and/or neutralizing the biological activity of the polypeptides according to the invention. Indeed, a further characteristic of a polypeptide of the invention is that it specifically binds an antibody of the invention, i.e., an antibody specific for an LLG polypeptide.

Another aspect of this invention is a composition comprising a polypeptide, nucleic acid, vector, antisense nucleic acid, or antibody according to the invention and a pharmaceutically acceptable carrier.

Another aspect of this invention is a method of screening for agonists or antagonists of enzymatic activity exhibited by the polypeptides of the present invention comprising contacting potential agonists or antagonists with said polypeptides and a substrate thereof and measuring the ability of the potential agonists or antagonists to enhance or inhibit activity.

Another aspect of this invention is a method for the enzymatic hydrolysis of a phosphatidylcholine ester comprising contacting said phosphatidylcholine ester with a polypeptide according to the invention.

Another aspect of this invention is a method of treatment for improving the serum lipid profile of a human or other animal having an undesirable lipid profile comprising administration thereto of an effective amount of a composition according to the invention.

Another aspect of this invention is a method of treating or preventing atherosclerosis in a human or other animal comprising administration thereto of an effective amount of a composition according to the invention.

Other aspects and advantages of the present invention are described further in the drawings and in the following detailed description of the preferred embodiments thereof.

BRIEF DESCRIPTION OF THE DRAWINGS

FIG. 1 shows the sequences (SEQ ID Nos: 17-31) of the primers used in the exemplified PCR amplifications.

FIG. 2 shows the nucleic acid sequence (SEQ ID NO: 1) and the deduced amino acid sequence (SEQ ID NO: 2) of the differential display RT-PCR product containing the lipase like gene cDNA. The sequences corresponding to the two primers used in the amplification are underlined. The termination codon and polyadenylation signal are boxed. The GAATTC motifs and flanking sequence are from the pCRII vector into which the product was cloned.

FIG. 3 shows the nucleic acid sequence (SEQ ID NO: 3) and the deduced amino acid sequence (SEQ ID NO: 4) of the 5' RACE extension of the LLG cDNA. The sequences corresponding to the two primers used in the amplification are underlined. The GAATTC motifs and flanking sequence are from the pCRII vector into which the product was cloned.

FIG. 4 shows the sequence (SEQ ID NO: 7) of the cDNA containing the complete open reading frame of the lipase like gene, LLGXL. The start codon (ATG) and termination codon (TGA) are boxed. The DraI site (TTTAAA) and SrfI site (GCCCGGGC) used in the construction of the expression vectors are underlined.

FIG. 5 shows the deduced amino acid sequence (SEQ ID NO: 8) of the LLGXL protein. The predicted signal sequence is underlined.

FIG. 8 shows a northern analysis of mRNAs from multiple human tissues probed with LLG, lipoprotein lipase (LPL) and human beta actin cDNAs. The position of a 4.4 kilobase RNA standard is indicated to the left of the LLG and LPL panels.

FIG. 9 shows a northern analysis of LLG and LPL expression in cultured human endothelial cells and THP-1 cells. The cells were either unstimulated (not exposed to PMA) or stimulated with PMA.

FIG. 10 shows the sequence of the immunizing peptide (SEQ ID NO: 16) and its relation to the LLGXL protein sequence. The peptide is shown in the shaded box. The terminal cysteine was introduced to aid coupling of the peptide to the carrier protein.

Figure 13:
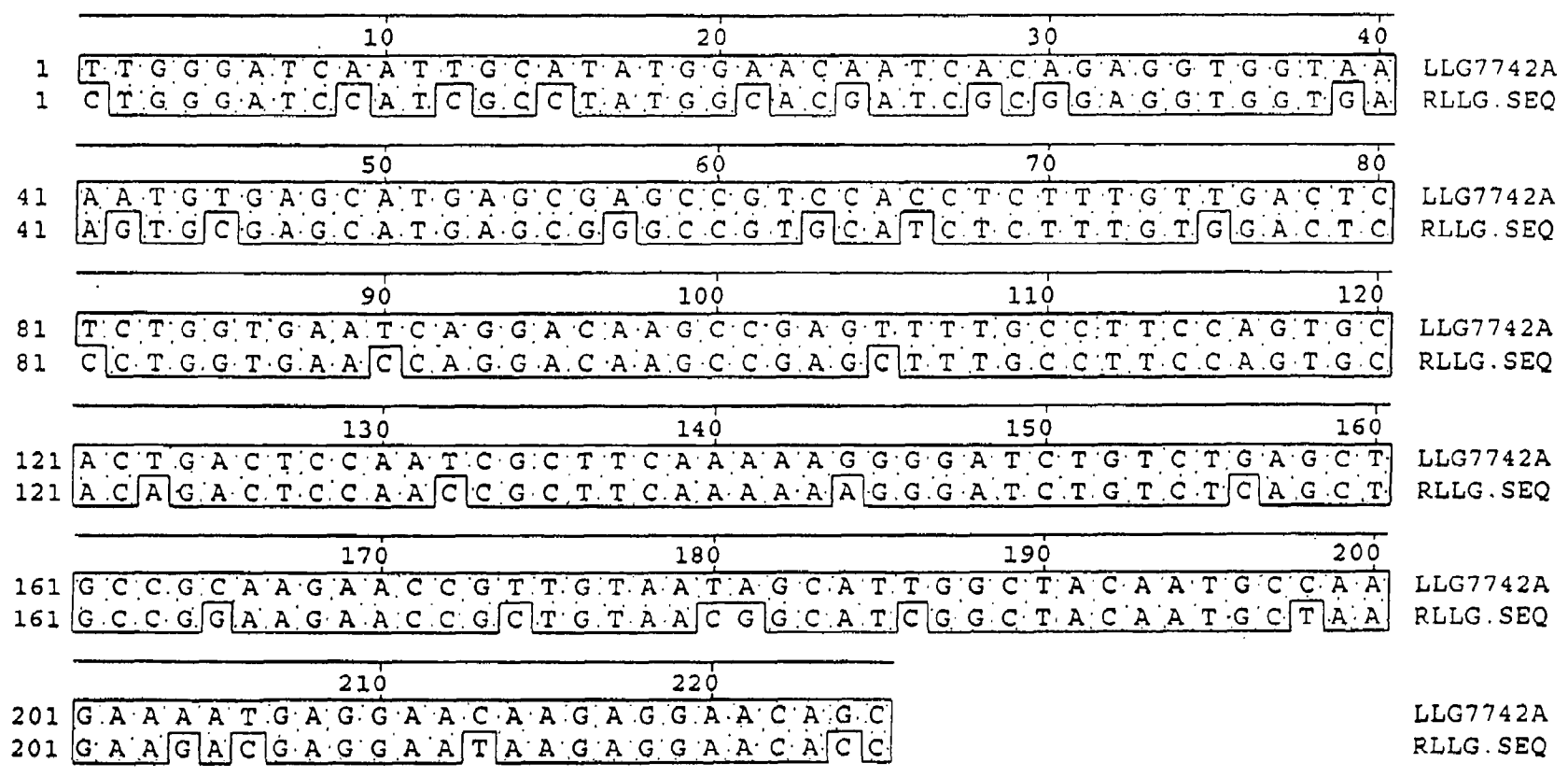

FIG. 13 shows the sequence of the rabbit LLG PCR product (RLLG.SEQ, SEQ ID NO: 12) and the sequence alignment between the rabbit LLG PCR product and the corresponding sequence in the human cDNA (LLG7742A). Identical nucleotides are shaded.

FIG. 16 shows the hybridization of LLG and LPL probes to genomic DNAs from different species.

DETAILED DESCRIPTION OF THE INVENTION

Figure 6:
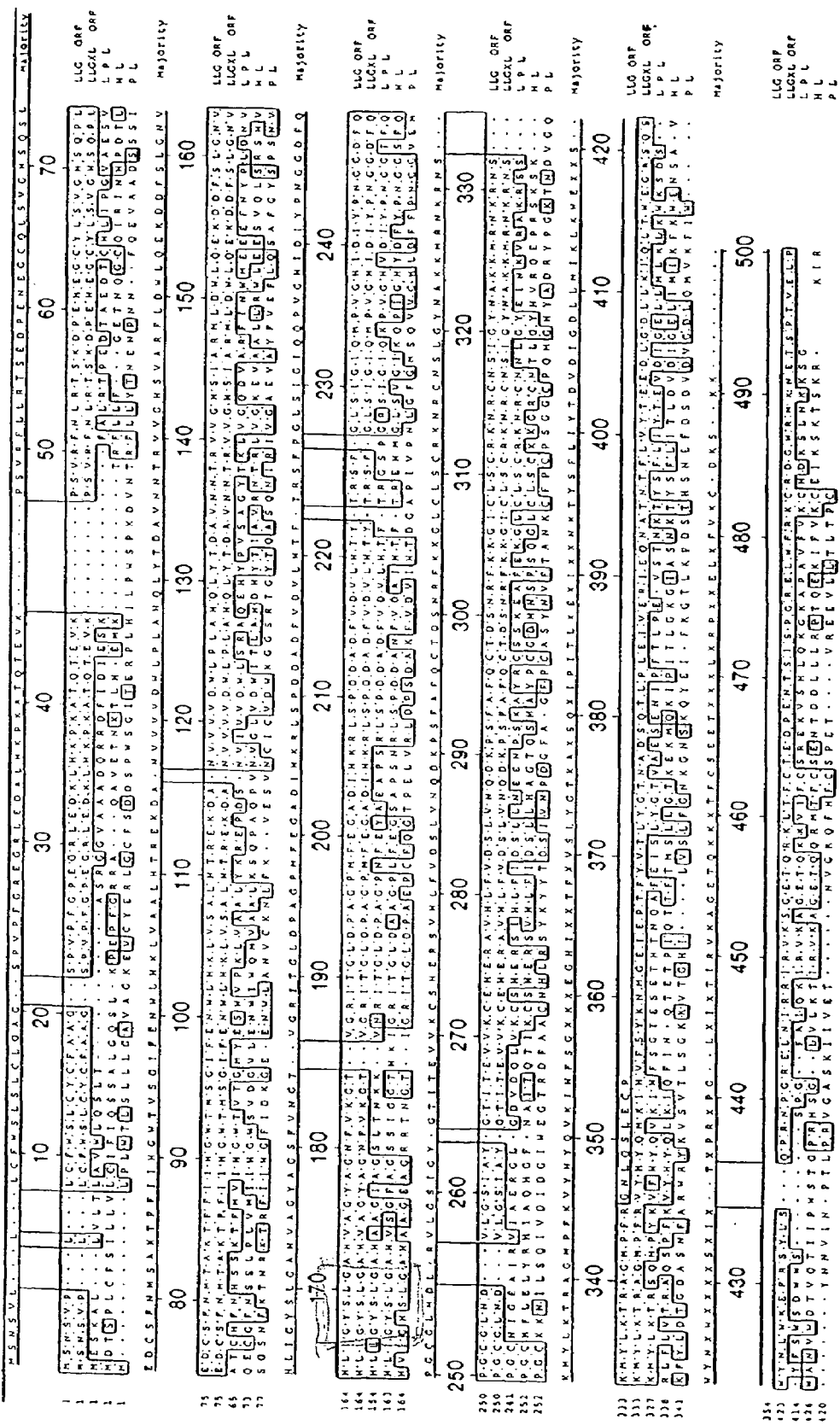
FIG. 6 shows a protein sequence alignment of the members of the triacylglycerol lipase gene family (SEQ ID Nos: 13-15). Shaded residues are identical to the LLGXL protein (SEQ ID NO: 8). Gaps were introduced into the sequences to maximize the alignment values using the CLUSTAL program.

The present invention relates to the discovery of a lipase like gene (LLG) and its expressed polypeptide products. The polypeptide products, members of the triacylglycerol lipase family, comprise an approximately 39 kD catalytic domain of the triacylglycerol lipase family, e.g., having the sequence SEQ ID NO: 10. One embodiment of the present invention is the LLGN polypeptide, which has 354 amino acids. A second embodiment of the present invention is the LLGXL polypeptide, which has 500 amino acids and exhibits 43% similarity to human lipoprotein lipase and 37% similarity to human hepatic lipase. The LLGXL polypeptide has phospholipase A activity.

The inventors isolated a partial cDNA from mRNA of THP-1 cells which had been exposed to phorbol ester and oxidized LDLs. Following a 5' RACE extension of this partial cDNA, the smaller alternately spliced cDNA was isolated. A second, larger cDNA was isolated from a human placental cDNA library.

Northern analysis demonstrated that the LLG gene is expressed in endothelial cells. Antisera raised against a peptide predicted from the open reading frame of the cDNA detected proteins of the predicted sizes for LLGN and LLGXL in conditioned medium from cultured endothelial cells. Treatment of endothelial cells with phorbol esters resulted in increased production of LLG at both the mRNA and protein levels. This is the first member of the triacylglycerol lipase family found to be expressed by endothelial cells.

A) Definitions

The following defined terms are used throughout the present specification and should be helpful in understanding the scope and practice of the present invention.

A "polypeptide" is a polymeric compound comprised of covalently linked amino acid residues. Amino acids have the following general structure:

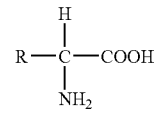

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

A "protein" is a polypeptide which plays a structural or functional role in a living cell.

The polypeptides and proteins of the invention may be glycosylated or unglycosylated.

"Homology" means similarity of sequence reflecting a common evolutionary origin. Polypeptides or proteins are said to have homology, or similarity, if a substantial number of their amino acids are either (1) identical, or (2) have a chemically similar R side chain. Nucleic acids are said to have homology if a substantial number of their nucleotides are identical.

"Isolated polypeptide" or "isolated protein" is a polypeptide or protein which is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

"LLGN polypeptide" and "LLGN protein" mean a polypeptide including the sequence SEQ ID NO: 6, said polypeptide being glycosylated or non-glycosylated.

"LLGXL polypeptide" and "LLGXL protein" mean a polypeptide including the sequence SEQ ID NO: 8, said polypeptide being glycosylated or non-glycosylated.

"LLG polypeptide" generically describes both the LLGN polypeptide and the LLGXL polypeptide.

The LLG polypeptide or protein of the invention includes any analogue, fragment, derivative, or mutant which is derived from an LLG polypeptide and which retains at least one biological property of the LLG polypeptide. Different variants of the LLG polypeptide exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the LLG polypeptide, (c) variants in which one or more of the amino acids includes a substituent group, and (d) variants in which the LLG polypeptide is fused with another polypeptide such as serum albumin. Other LLG polypeptides of the invention include variants in which amino acid residues from one species are substituted for the corresponding residue in another species, either at conserved or non-conserved positions. In another embodiment, amino acid residues at non-conserved positions are substituted with conservative or non-conservative residues. The techniques for obtaining these variants, including genetic (suppressions, deletions, mutations, etc.), chemical, and enzymatic techniques, are known to persons having ordinary skill in the art.

If such allelic variations, analogues, fragments, derivatives, mutants, and modifications, including alternative mRNA splicing forms and alternative post-translational modification forms result in derivatives of the LLG polypeptide which retain any of the biological properties of the LLG polypeptide, they are included within the scope of this invention.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA. The sequence of nucleotides that encodes a protein is called the sense sequence.

An "antisense nucleic acid" is a sequence of nucleotides that is complementary to the sense sequence. Antisense nucleic acids can be used to down regulate or block the expression of the polypeptide encoded by the sense strand.

"Isolated nucleic acid" means a nucleic acid which is substantially free of those compounds that are normally associated therewith in its natural state. "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

The phrase "a nucleic acid which hybridizes at high stringency" means that the hybridized nucleic acids are able to withstand a washing under high stringency conditions. An example of high stringency washing conditions for DNA-DNA hybrids is 0.1×SSC, 0.5% SDS at 68° C. Other conditions of high stringency washing are known to persons having ordinary skill in the art.

"Regulatory region" means a nucleic acid sequence which regulates the expression of a nucleic acid. A regulatory region may include sequences which are naturally responsible for expressing a particular nucleic acid (a homologous region) or may include sequences of a different origin (responsible for expressing different proteins or even synthetic proteins). In particular, the sequences can be sequences of eukaryotic or viral genes or derived sequences which stimulate or repress transcription of a gene in a specific or non-specific manner and in an inducible or non-inducible manner. Regulatory regions include origins of replication, RNA splice sites, enhancers, transcriptional termination sequences, signal sequences which direct the polypeptide into the secretory pathways of the target cell, and promoters.

A regulatory region from a "heterologous source" is a regulatory region which is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

A "vector" is any means for the transfer of a nucleic acid according to the invention into a host cell. The term "vector" includes both viral and nonviral means for introducing the nucleic acid into a prokaryotic or eukaryotic cell in vitro, ex vivo or in vivo. Non-viral vectors include plasmids, liposomes, electrically charged lipids (cytofectins), DNA-protein complexes, and biopolymers. Viral vectors include retrovirus, adeno-associated virus, pox, baculovirus, vaccinia, herpes simplex, Epstein-Barr and adenovirus vectors. In addition to nucleic acid according to the invention, a vector may also contain one or more regulatory regions; and/or selectable markers useful in selecting, measuring, and monitoring nucleic acid transfer results (transfer to which tissues, duration of expression, etc.).

A "recombinant cell" is a cell which contains a nucleic acid which is not naturally present in the cell. "Recombinant cell" includes higher eukaryotic cells such as mammalian cells, lower eukaryotic cells such as yeast cells, prokaryotic cells, and archaebacterial cells.

"Pharmaceutically acceptable carrier" includes diluents and fillers which are pharmaceutically acceptable for method of administration, are sterile, and may be aqueous or oleaginous suspensions formulated using suitable dispersing or wetting agents and suspending agents. The particular pharmaceutically acceptable carrier and the ratio of active compound to carrier are determined by the solubility and chemical properties of the composition, the particular mode of administration, and standard pharmaceutical practice.

A "lipase" is a protein which can enzymatically cleave a lipid substrate.

A "phospholipase" is a protein which can enzymatically cleave a phospholipid substrate.

A "triacylglycerol lipase" is a protein which can enzymatically cleave a triacylglyceride substrate.

"Phosphatidylcholine" is a glycerol phospholipid having the following structure:

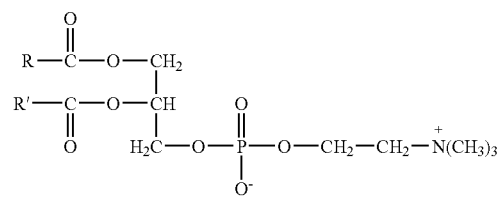

R and R' are the hydrocarbon side chains of fatty acids. Phosphatidylcholine is also known as lecithin.

"Lipid profile" means the set of concentrations of cholesterol, triglyceride, lipoprotein cholesterol and other lipids in the body of a human or other animal.

An "undesirable lipid profile" is the condition in which the concentrations of cholesterol, triglyceride, or lipoprotein cholesterol are outside of the age- and gender-adjusted reference ranges. Generally, a concentration of total cholesterol >200 mg/dl, of plasma triglycerides >200 mg/dl, of LDL cholesterol >130 mg/dl, of HDL cholesterol <39 mg/dl, or a ratio of total cholesterol to HDL cholesterol >4.0 is considered to be an undesirable lipid profile. An undesirable lipid profile is associated with a variety of pathological conditions, including hyperlipidaemias, diabetes hypercholesterolaemia, atherosclerosis, and other forms of coronary artery disease.

B) Polypeptides

The present invention provides polypeptides which are members of the triacylglycerol lipase family, and which comprise a 39 kD catalytic domain of the triacylglycerol lipase family, e.g., having the sequence SEQ ID NO: 10. One embodiment of the present invention is an isolated LLG polypeptide comprising the sequence SEQ ID NO: 6 and having an apparent molecular weight of about 40 kD on a 10% SDS-PAGE gel Another embodiment of the present invention is an isolated LLG polypeptide comprising the sequence SEQ ID NO: 8 and having an apparent molecular weight of about 55 kD or 68 kD on a 10% SDS-PAGE gel.

The polypeptides and proteins of the present invention may be recombinant polypeptides, natural polypeptides, or synthetic polypeptides, and may be of human, rabbit, or other animal origin. The polypeptides are characterized by a reproducible single molecular weight and/or multiple set of molecular weights, chromatographic response and elution profiles, amino acid composition and sequence, and biological activity.

The polypeptides of the present invention may be isolated from natural sources, such as placental extracts, human plasma, or conditioned media from cultured cells such as macrophages or endothelial cells, by using the purification procedures known to one of skill in the art.

Alternatively, the polypeptides of the present invention may be prepared utilizing recombinant DNA technology, which comprises combining a nucleic acid encoding the polypeptide thereof in a suitable vector, inserting the resulting vector into a suitable host cell, recovering the polypeptide produced by the resulting host cell, and purifying the polypeptide recovered.

C) Nucleic Acids

The present invention provides isolated nucleic acids which encode LLG polypeptides.

The present invention also provides antisense nucleic acids which can be used to down regulate or block the expression of LLG polypeptides in vitro, ex vivo or in vivo.

The techniques of recombinant DNA technology are known to those of ordinary skill in the art General methods for the cloning and expression of recombinant molecules are described in Maniatis (*Molecular Cloning*, Cold Spring Harbor Laboratories, 1982), and in Ausubel (*Current Protocols in Molecular Biology*, Wiley and Sons, 1987), which are incorporated by reference.

The nucleic acids of the present invention may be linked to one or more regulatory regions. Selection of the appropriate regulatory region or regions is a routine matter, within the level of ordinary skill in the art. Regulatory regions include promoters, and may include enhancers, suppressors, etc.:

Promoters that may be used in the present invention include both constitutive promoters and regulated (inducible) promoters. The promoters may be prokaryotic or eukaryotic depending on the host. Among the prokaryotic (including bacteriophage) promoters useful for practice of this invention are lacI, lacZ, T3, T7, lambda $P_r$, $P_l$, and trp promoters. Among the eukaryotic (including viral) promoters useful for practice of this invention are ubiquitous promoters (e.g. HPRT, vimentin, actin, tubulin), intermediate filament promoters (e.g. desmin, neurofilaments, keratin, GFAP), therapeutic gene promoters (e.g. MDR type, CFTR, factor VIII), tissue-specific promoters (e.g. actin promoter in smooth muscle cells, or Flt and Flk promoters active in endothelial cells), promoters which are preferentially activated in dividing cells, promoters which respond to a stimulus (e.g. steroid hormone receptor, retinoic acid receptor), tetracycline-regulated transcriptional modulators, cytomegalovirus immediate-early, retroviral LTR, metallothionein, SV-40, E1a, and MLP promoters. Tetracycline-regulated transcriptional modulators and CMV promoters are described in WO 96/01313, U.S. Pat. Nos. 5,168,062 and 5,385,839, the contents of which are incorporated herein by reference.

Preferably, the viral vectors used in gene therapy are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), be rendered non-functional by any technique known to a person skilled in the art These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents.

Preferably, the replication defective virus retains the sequences of its genome which are necessary for encapsidating the viral particles.

The retroviruses are integrating viruses which infect dividing cells. The retrovirus genome includes two LTRs, an encapsidation sequence and three coding regions (gag, pol and env). The construction of recombinant retroviral vectors has been described: see, in particular, EP 453242, EP178220, Bernstein et al. Genet. Eng. 7 (1985) 235; McCormick, Bio-Technology 3(1985) 689, etc. In recombinant retroviral vectors, the gag, pol and env genes are generally deleted, in whole or in part, and replaced with a heterologous nucleic acid sequence of interest. These vectors can be constructed from different types of retrovirus, such as, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus.

In general, in order to construct recombinant retroviruses containing a sequence encoding LLG according to the invention, a plasmid is constructed which contains the LTRs, the encapsidation sequence and the coding sequence. This construct is used to transfect a packaging cell line, which cell line is able to supply in trans the retroviral functions which are deficient in the plasmid. In general, the packaging cell lines are thus able to express the gag, pol and env genes. Such packaging cell lines have been described in the prior art, in particular the cell line PA317 (U.S. Pat. No. 4,861,719); the PsiCRIP cell line (WO90/02806) and the GP+envAm-12 cell line (WO89/07150). In addition, the recombinant retroviral vectors can contain modifications within the LTRs for suppressing transcriptional activity as well as extensive encapsidation sequences which may include a part of the gag gene (Bender et al., J. Virol. 61 (1987)1639). Recombinant retroviral vectors are purified by standard techniques known to those having ordinary skill in the art.

The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions which carry the encapsidation functions: the left-hand part of the genome, which contains the rep gene involved in viral replication and expression of the viral genes; and the right-hand part of the genome, which contains the cap gene encoding the capsid proteins of the virus.

The use of vectors derived from the AAVs for transferring genes in vitro and in vivo has been described (see WO 91/18088; WO 93/09239; U.S. Pat. Nos. 4,797,368, 5,139,941, EP 488 528). These publications describe various AAV-derived constructs in which the rep and/or cap genes are deleted and replaced by a gene of interest, and the use of these constructs for transferring the said gene of interest in vitro (into cultured cells) or in vivo, (directly into an organism). The replication defective recombinant AAVs according to the invention can be prepared by cotransfecting a plasmid containing the nucleic acid sequence of interest flanked by two AAV inverted terminal repeat (ITR) regions, and a plasmid carrying the AAV encapsidation genes (rep and cap genes), into a cell line which is infected with a human helper virus (for example an adenovirus). The AAV recombinants which are produced are then purified by standard techniques. The invention also relates, therefore, to an AAV-derived recombinant virus whose genome encompasses a sequence encoding an LLG polypeptide flanked by the AAV ITRs. The invention also relates to a plasmid encompassing a sequence encoding an LLG polypeptide flanked by two ITRs from an AAV. Such a plasmid can be used as it is for transferring the LLG sequence, with the plasmid, where appropriate, being incorporated into a liposomal vector (pseudo-virus).

In a preferred embodiment, the vector is an adenovirus vector.

Adenoviruses are eukaryotic DNA viruses that can be modified to efficiently deliver a nucleic acid of the invention to a variety of cell types.

Various serotypes of adenovirus exist. Of these serotypes, preference is given, within the scope of the present invention, to using type 2 or type 5 human adenoviruses (Ad 2 or Ad 5) or adenoviruses of animal origin (see WO94/26914). Those adenoviruses of animal origin which can be used within the scope of the present invention include adenoviruses of canine, bovine, murine (example: Mav1, Beard et al., Virology 75 (1990)81), ovine, porcine, avian, and simian (example: SAV) origin. Preferably, the adenovirus of animal origin is a canine adenovirus, more preferably a CAV2 adenovirus (e.g. Manhattan or A26/61 strain (ATCC VR-800), for example).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus. Other regions may also be modified, in particular the E3 region (WO95/02697), the E2 region (WO94/28938), the E4 region (WO94/28152, WO94/12649 and WO95/02697), or in any of the late genes L1-L5. Defective retroviral vectors are disclosed in WO95/02697.

In a preferred embodiment, the adenoviral vector has a deletion in the E1 and E4 regions. In another preferred embodiment, the adenoviral vector has a deletion in the E1 region into which the E4 region and the sequence encoding LLG are inserted (see FR94 13355).

The replication defective recombinant adenoviruses according to the invention can be prepared by any technique known to the person skilled in the art (Levrero et al., Gene 101 (1991) 195, EP 185 573; Graham, EMBO J. 3 (1984) 2917). In particular, they can be prepared by homologous recombination between an adenovirus and a plasmid which carries, inter alia, the DNA sequence of interest. The homologous recombination is effected following cotransfection of the said adenovirus and plasmid into an appropriate cell line. The cell line which is employed should preferably (i) be transformable by the said elements, and (ii) contain the sequences which are able to complement the part of the genome of the replication defective adenovirus, preferably in integrated form in order to avoid the risks of recombination. Examples of cell lines which may be used are the human embryonic kidney cell line 293 (Graham et al., J. Gen. Virol. 36 (1977) 59) which contains the left-hand portion of the genome of an Ad5 adenovirus (12%) integrated into its genome, and cell lines which are able to complement the E1 and E4 functions, as described in applications WO94/26914 and WO95/02697. Recombinant adenoviruses are recovered and purified using standard molecular biological techniques, which are well known to one of ordinary skill in the art.

The down regulation of gene expression using antisense nucleic acids can be achieved at the translational or transcriptional level. Antisense nucleic acids of the invention are preferably nucleic acid fragments capable of specifically hybridizing with all or part of a nucleic acid encoding LLG or the corresponding messenger RNA. These antisense nucleic acids can be synthetic oligonucleotides, optionally modified to improve their stability and selectivity. They can also be DNA sequences whose expression in the cell produces RNA complementary to all or part of the LLG mRNA. Antisense nucleic acids can be prepared by expression of all or part of a sequence selected from the group consisting of SEQ ID No. 2, SEQ ID No. 3, SEQ ID No. 7, or SEQ ID No. 11, in the opposite orientation, as described in EP 140308. Any length of antisense sequence is suitable for practice of the invention so long as it is capable of down-regulating or blocking expression of LLG. Preferably, the antisense sequence is at least 20 nucleotides in length. The preparation and use of antisense nucleic acids, DNA encoding antisense RNAs and the use of oligo and genetic antisense is disclosed in WO92/15680, the contents of which are incorporated herein by reference.

D) Antibodies

The present invention provides antibodies against the LLG polypeptide. These antibodies may be monoclonal antibodies or polyclonal antibodies. The present invention includes chimeric, single chain, and humanized antibodies, as well as Fab fragments and the products of an Fab expression library.

Polyclonal antibodies may be prepared against an antigenic fragment of an LLG polypeptide, as described in Example 4A. Antibodies may also be generated against the intact LLG protein or polypeptide, or against a fragment, derivative, or epitope of the protein or polypeptide. Antibodies may be obtained following the administration of the protein, polypeptide, fragment, derivative, or epitope to an animal, using the techniques and procedures known in the art.

Monoclonal antibodies may be prepared using the method of Mishell, B. B., et al., Selected Methods In Cellular Immunology, (W.H. Freeman, ed.) San Francisco (1980). Briefly, a polypeptide of the present invention is used to immunize spleen cells of Balb/C mice. The immunized spleen cells are fused with myeloma cells. Fused cells containing spleen and myeloma cell characteristics are isolated by growth in HAT medium, a medium which kills both parental cells, but allows the fused products to survive and grow.

The monoclonal antibodies of the present invention may be "humanized" to prevent the host from mounting an immune response to the antibodies. A "humanized antibody" is one in which the complementarity determining regions (CDRs) and/or other portions of the light and/or heavy variable domain framework are derived from a non-human immunoglobulin, but the remaining portions of the molecule are derived from one or more human immunoglobulins. Humanized antibodies also include antibodies characterized by a humanized heavy chain associated with a donor or acceptor unmodified light chain or a chimeric light chain, or vice versa. The humanization of antibodies may be accomplished by methods known in the art (see, e.g. G. E. Mark and E. A. Padlan, "Chapter 4. Humanization of Monoclonal Antibodies", The Handbook of Experimental Pharmacology Vol. 113, Springer-Verlag, New York, 1994). Transgenic animals may be used to express humanized antibodies.

Techniques known in the art for the production of single chain antibodies can be adapted to produce single chain antibodies to the immunogenic polypeptides and proteins of the present invention.

The anti-LLG antibodies are useful in assays for detecting or quantitating levels of LLG. In one embodiment, these assays provide a clinical diagnosis and assessment of LLG in various disease states and a method for monitoring treatment efficacy.

E) Methods of Screening for Agonists or Antagonists

The present invention provides methods of screening small molecule libraries or natural product sources for agonists (enhancers or co-activators including proteinaceous co-activators) or antagonists (inhibitors) of LLGXL activity. A potential agonist or antagonist is contacted with LLGXL protein and a substrate of LLGXL, and the ability of the potential agonist or antagonist to enhance or inhibit LLGXL activity is measured.

The LLGXL protein used in the method can be produced recombinantly in a variety of host cells, including mammalian cells (as shown in Example 7), baculovirus-infected insect cells, yeast, and bacteria. LLG expression in stably transfected CHO cells can be optimized by methotrexate amplification of the cells. LLGXL protein can also be purified from natural sources such as human plasma, placental extracts, or conditioned media from cultured endothelial cells, THP-1 cells, or macrophages.

The optimization of assay parameters including pH, ion concentrations, temperature, concentration of substrate, and emulsification conditions are determined empirically by one having ordinary skill in the art.

The fatty acid substituents of the substrates may vary in chain length as well as in degree and position of unsaturation. The substrates may be radiolabelled in any of several positions. Phospholipid substrates such as phosphatidylcholine can be radiolabelled, for example, in the Sn-1 or Sn-2 fatty acid position, or in the glycerol, phosphate, or polar head group (choline in the case of phosphatidylcholine).

As an alternative to radiolabeled substrates, other classes of labeled substrates, such as fluorescent substrates or thio-containing substrates, can also be used in the screening methods.

Fluorescent substrates are particularly useful in screening assays because enzymatic catalysis can be measured continuously by measuring fluorescence intensity, without the physical separation (extraction) of the products from the substrates. An example of a fluorescent phosphatidylcholine substrate is $C_6$NBD-PC{1-acyl-2-[6-(nitro-2,1,3-benzoxadiazol-4-yl)amino]caproylphosphatidylcholine.

The thio-containing substrates include 1,2-bis(hexanoylthio)-1,2-dideoxy-sn-glycero-3-phosphorylcholine (L. J. Reynolds, W. N. Washburn, R. A. Deems, and E. A. Dennis, 1991. Methods in Enzymology 197: 3-23; L. Yu and E. A. Dennis, 1991. Methods in Enzymology 197: 65-75; L. A. Wittenauer, K. Shirai, R. L. Jackson, and J. D. Johnson, 1984. Biochem. Biophys. Res. Commun. 118: 894-901).

F) Hydrolysis of Phosphatidylcholine Esters

The present invention provides a method for the enzymatic hydrolysis of phosphatidylcholine esters, e.g., for industrial or food processing, or in laundry detergents. The polypeptides of the present invention can be used to hydrolyze phosphatidylcholine esters in solution, or the enzymes may be bound to a solid support which is then contacted with the substrate. This method can be used to produce lysophospholipids and free fatty acids.

G) Compositions

The present invention provides compositions in a biologically compatible (biocompatible) solution, comprising the polypeptides, nucleic acids, vectors, and antibodies of the invention. A biologically compatible solution is a solution in which the polypeptide, nucleic acid, vector, or antibody of the invention is maintained in an active form, e.g., in a form able to effect a biological activity. For example, a polypeptide of the invention would have phospholipase activity; a nucleic acid would be able to replicate, translate a message, or hybridize to a complementary nucleic acid; a vector would be able to transfect a target cell; an antibody would bind a polypeptide of the invention. Generally, such a biologically compatible solution will be an aqueous buffer, e.g., Tris, phosphate, or HEPES buffer, containing salt ions. Usually the concentration of salt ions will be similar to physiological levels. In a specific embodiment, the biocompatible solution is a pharmaceutically acceptable composition. Biologically compatible solutions may include stabilizing agents and preservatives.

Such compositions can be formulated for administration by topical, oral, parenteral, intranasal, subcutaneous, and intraocular, routes. Parenteral administration is meant to include intravenous injection, intramuscular injection, intraarterial injection or infusion techniques. The composition may be administered parenterally in dosage unit formulations containing standard, well known nontoxic physiologically acceptable carriers, adjuvants and vehicles as desired.

The preferred sterile injectable preparations can be a solution or suspension in a nontoxic parenterally acceptable solvent or diluent. Examples of pharmaceutically acceptable carriers are saline, buffered saline, isotonic saline (e.g. monosodium or disodium phosphate, sodium, potassium, calcium or magnesium chloride, or mixtures of such salts), Ringer's solution, dextrose, water, sterile water, glycerol, ethanol, and combinations thereof. 1,3-butanediol and sterile fixed oils are conveniently employed as solvents or suspending media. Any bland fixed oil can be employed including synthetic mono- or di-glycerides. Fatty acids such as oleic acid also find use in the preparation of injectables.

The composition medium can also be a hydrogel which is prepared from any biocompatible or non-cytotoxic (homo or hetero) polymer, such as a hydrophilic polyacrylic acid polymer that can act as a drug absorbing sponge. Such polymers have been described, for example, in application WO93/08845, the entire contents of which are hereby incorporated by reference. Certain of them, such as, in particular, those obtained from ethylene and/or propylene oxide are commercially available. A hydrogel can be deposited directly onto the surface of the tissue to be treated, for example during surgical intervention.

Another preferred embodiment of the present invention relates to a pharmaceutical composition comprising a replication defective recombinant virus and poloxamer. More specifically, the invention relates to a composition comprising a replication defective recombinant virus comprising a nucleic acid encoding an LLG polypeptide and poloxamer. A preferred poloxamer is Poloxamer 407, which is commercially available (BASF, Parsippany, N.J.) and is a non-toxic, biocompatible polyol, and is most preferred. A poloxamer impregnated with recombinant viruses may be deposited directly on the surface of the tissue to be treated, for example during a surgical intervention. Poloxamer possesses essentially the same advantages as hydrogel while having a lower viscosity.

H) Methods of Treatment

The present invention provides methods of treatment which comprise the administration to a human or other animal of an effective amount of a composition of the invention.

Effective amounts may vary, depending on the age, type and severity of the condition to be treated, body weight, desired duration of treatment, method of administration, and other parameters. Effective amounts are determined by a physician or other qualified medical professional.

Polypeptides according to the invention are generally administered in doses of about 0.01 mg/kg to about 100 mg/kg, preferably about 0.1 mg/kg to about 50 mg/kg, and most preferably about 1 mg/kg to about 10 mg/kg of body weight per day.

Recombinant viruses according to the invention are generally formulated and administered in the form of doses of between about $10^4$ and about $10^{14}$ pfu. In the case of AAVs and adenoviruses, doses of from about $10^6$ to about $10^{11}$ pfu are preferably used. The term pfu ("plaque-forming unit") corresponds to the infective power of a suspension of virions and is determined by infecting an appropriate cell culture and measuring the number of plaques formed. The techniques for determining the pfu titre of a viral solution are well documented in the prior art.

The present invention provides methods of treating atherosclerosis wherein said atherosclerosis is the result of excess, abnormal or inadequate expression of LLG polypeptide activity.

The present invention further provides methods of treating a human or other animal having an undesirable lipid profile, wherein said undesirable lipid profile is the result of abnormally high or inadequate expression of LLG polypeptide activity.

The present invention further provides methods of treating diabetes, hyperlipidemia, intrahepatic cholestasis or other metabolic disorders wherein said diabetes, hyperlipidemia, intrahepatic cholestasis or other metabolic disorder is the result of abnormally high or inadequate expression of LLG polypeptide activity.

1) Treatment of Undesirable Lipid Profiles Associated with Increased Expression of LLG Polypeptide The methods for decreasing the expression of LLG polypeptide to correct those conditions in which LLG polypeptide activity contributes to a disease or disorder associated with an undesirable lipid profile include but are not limited to administration of a composition comprising an antisense nucleic acid, administration of a composition comprising an intracellular binding protein such as an antibody, administration of a composition comprising the LLGN polypeptide or another fragment of LLG and administration of a composition comprising a nucleic acid which encodes the LLGN polypeptide or another fragment of LLG.

In one embodiment, a composition comprising an antisense nucleic acid is used to down-regulate or block the expression of LLG. In one preferred embodiment, the nucleic acid encodes antisense RNA molecules. In this embodiment, the nucleic acid is operably linked to signals enabling expression of the nucleic acid sequence and is introduced into a cell utilizing, preferably, recombinant vector constructs, which will express the antisense nucleic acid once the vector is introduced into the cell. Examples of suitable vectors includes plasmids, adenoviruses, adeno-associated viruses, retroviruses, and herpes viruses. Preferably, the vector is an adenovirus. Most preferably, the vector is a replication defective adenovirus comprising a deletion in the E1 and/or E3 regions of the virus.

In another embodiment, the expression of LLG is down-regulated or blocked by the expression of a nucleic acid sequence encoding an intracellular binding protein which is capable of selectively interacting with LLG. WO 94/29446 and WO 94/02610, the contents of which are incorporated herein by reference, disclose cellular transfection with genes encoding an intracellular binding protein. An intracellular binding protein includes any protein capable of selectively interacting, or binding, with LLG in the cell in which it is expressed and of neutralizing the function of bound LLG. Preferably, the intracellular binding protein is an antibody or a fragment of an antibody. More preferably, the intracellular binding protein is a single chain antibody.

WO 94/02610 discloses preparation of antibodies and identification of the nucleic acid encoding a particular antibody. Using LLG or a fragment thereof, a specific monoclonal antibody is prepared by techniques known to those skilled in the art. A vector comprising the nucleic acid encoding an intracellular binding protein, or a portion thereof, and capable of expression in a host cell is subsequently prepared for use in the method of this invention.

Alternatively, LLG activity can be blocked by administration of a neutralizing antibody into the circulation. Such a neutralizing antibody can be administered directly as a protein, or it can be expressed from a vector (with a secretory signal).

In another embodiment, LLGXL activity is inhibited by the administration of a composition comprising the LLGN polypeptide or another fragment of LLG. This composition may be administered in a convenient manner, such as by the oral, topical, intravenous, intraperitoneal, intramuscular, subcutaneous, intranasal, or intradermal routes. The composition may be administered directly or it may be encapsulated (e.g. in a lipid system, in amino acid microspheres, or in globular dendrimers). The polypeptide may, in some cases, be attached to another polymer such as serum albumin or polyvinyl pyrrolidone.

In another embodiment, LLGXL activity is inhibited through the use of small molecular weight compounds, which interfere with its enzymatic properties or prevent its appropriate recognition by cellular binding sites.

In another embodiment, LLGXL activity is inhibited through the use of gene therapy, that is, through the administration of a composition comprising a nucleic acid which encodes and directs the expression of the LLGN polypeptide or another fragment of LLG.

In a specific embodiment, the LLG gene of the present invention also has an affinity for heparin. LLG polypeptide binding to extracellular heparin in the lumen of blood vessels would permit LLG to bind to and accelerate LDL uptake by acting as a bridge between LDL and the extracellular heparin. In the localized area of an atherosclerotic lesion, an increased level of lipase activity is hypothesized to accelerate the atherogenic process (Zilversmit, D. B. (1995) Clin. Chem. 41, 153-158; Zambon, A., Torres, A., Bijvoet, S., Gagne, C., Moojani, S., Lupien, P. J., Hayden M. R., and Brunzell, J. D. (1993) Lancet 341, 1119-1121). This may be due to an increase in the binding and uptake of lipoproteins by vascular tissue mediated by lipases (Eisenberg, S., Sehayek, E., Olivecrona, T. Vlodavsky, I. (1992) J. Clin. Invest. 90, 2013-2021; Tabas, I., Li, I., Brocia R. W., Xu, S. W., Swenson T. L. Williams, K-J. (1993) J. Biol. Chem. 268, 20419-20432; Nordestgaard, B. G., and Nielsen, A. G. (1994) Curr. Opin. Lipid. 5, 252-257; Williams, K. J., and Tabas, I. (1995) Art. Thromb. and Vasc. Biol. 15, 551-561). Additionally, a high local level of lipase activity may result in cytotoxic levels of fatty acids and lysophosphatidylcholine being produced in precursors of atherosclerotic lesions. This particular activity of LLG may contribute to the development or progression of atherosclerosis, particularly in the context of excessive lipid levels in a subject due to dietary or genetic factors. Thus, the present invention permits inhibition of lipoprotein accumulation by inhibiting LLG polypeptide expression or binding to lipoprotein (e.g., LDL).

2) Treatment of Undesirable Lipid Profiles Associated with Insufficient LLG Polypeptide Activity The methods for increasing the expression of LLG polypeptide to correct those conditions in which LLG polypeptide activity contributes to a disease or disorder associated with an undesirable lipid profile include but are not limited to administration of a composition comprising the LLGXL polypeptide and administration of a composition comprising a nucleic acid which encodes the LLGXL polypeptide.

In one embodiment, the level of LLGXL activity is increased through the administration of a composition comprising the LLGXL polypeptide. This composition may be administered in a convenient manner, such as by the oral, topical, intravenous, intraperitoneal, intramuscular, subcutaneous, intranasal, or intradermal routes. The composition may be administered directly or it may be encapsulated (e.g. in a lipid system, in amino acid microspheres, or in globular dendrimers). The polypeptide may, in some cases, be attached to another polymer such as serum albumin or polyvinyl pyrrolidone.

In another embodiment, the level of LLGXL is increased through the use of small molecular weight compounds, which can upregulate LLGXL expression at the level of transcription, translation, or post-translation.

In another embodiment, the level of LLGXL is increased through the use of gene therapy, that is, through the administration of composition comprising a nucleic acid which encodes and directs the expression of the LLGXL polypeptide.

Intrahepatic cholestasis can be characterized by increased serum cholesterol and phospholipid levels. A recently described, phalloidin drug-induced intrahepatic cholestasis model in rats demonstrated significant increases in the serum levels of cholesterol and phospholipid (Ishizaki, K., Kinbara, S., Miyazawa, N., Takeuchi, Y., Hirabayashi, N., Kasai, H., and Araki, T. (1997) Toxicol. Letters 90, 29-34). The products of this invention may be used to treat intrahepatic cholestasis in patients that have increased serum cholesterol and/or phospholipid. In addition, this rat model also exhibited a severe decrease in biliary cholesterol excretion rates. The LLG polypeptide and nucleic acid products of this invention may be used to treat patients with an impaired biliary excretion system.

Intrahepatic cholestasis is also characterized by impaired bile flow from the liver. Recently, the loci for progressive familial intrahepatic cholestasis (PFIC or Byler disease) and benign recurrent intrahepatic cholestasis (BRIC) were mapped to 18q21-q22 (Carlton, V. E. H., Knisely, A. S., and Freimer, N. B. (1995) Hum. Mol. Genet. 4, 1049-1053 and Houwen, R. H., Baharloo, S., Blankenship, K., Raeymaekers, P., Juyn, J., Sandkuijl, L. A., and Freimer, N. B. (1994) Nature Genet. 8, 380-386, respectively). As LLG gene maps within this chromosomal region at 18q21, the LLG gene or products of this invention may be used to treat patients with intrahepatic cholestasis that is caused by a mutation or defective expression of the PFIC/BRIC disease gene(s).

In another embodiment, the LLG gene or polypeptide products of this invention may be used to treat patients with intrahepatic cholestasis that is not due to a defect in the PFIC/BRIC disease gene(s) at 18q21-q22. A recent study suggested that another locus, located outside of the 18q21-q22 region may also produce the PFIC phenotype (Strautnieks, S. S., Kagalwalla, A. F., Tanner, M. S., Gardiner, R. M., and Thompson, R. J. (1996) J. Med. Genet. 33, 833-836). Nevertheless, administration of LLG polypeptide, either directly or via gene therapy, may alleviate this form of the condition.

In gene therapy one or more nucleic acids encoding a polypeptide, as well as regulatory regions controlling their expression, are transferred into the target cells of a human or other animal. This transfer is carried out either ex vivo in a procedure in which the nucleic acid is transferred to cells in the laboratory and the modified cells are then administered to the human or other animal, or in vivo in a procedure in which the nucleic acid is transferred directly to cells within the human or other animal. The transfer of nucleic acids can be achieved using either the viral or non-viral vectors described above.

Non-viral vectors may be transferred into cells using any of the methods known in the art, including calcium phosphate coprecipitation, lipofection (synthetic anionic and cationic liposomes), receptor-mediated gene delivery, naked DNA injection, electroporation and bioballistic or particle acceleration.

EXAMPLES

The following examples illustrate the invention. These examples are illustrative only, and do not limit the scope of the invention.

Example 1

Identification of a Differentially Expressed cDNA

A) RNA Preparation

Human monocytic THP-1 cells (Smith, P. K, Krohn, R. I., Hermanson, G. T., Mallia, A. K., Gartner, F. H. Provenzano, M. D., Fujimoto, E. K., Goeke, N. M., Olson, B. J., and Klenk, D. C. (1985) Anal. Biochem. 150, 76-85) were cultured in RPMI-1640 medium (GIBCO) with 25 mM HEPES, 10% fetal bovine serum, 100 units/ml penicillin G sodium and 100 units/ml streptomycin sulfate. Cells were plated onto 15 cm tissue culture dishes at $1.5 \times 10^7$ cells/plate, and treated with 40 ng/ml phorbol 12-myristate 13-acetate (Sigma) for 48 hours to induce differentiation of the cells. Human low density lipoproteins (LDL) were purchased from Calbiochem, and were dialyzed exhaustively versus PBS at 4° C. The LDL was then diluted to 500 µg/ml and dialyzed versus 5 µM $CuSO_4$ in PBS at 37° C. for 16 hours. To stop oxidation, the LDL was dialyzed exhaustively versus 150 mM NaCl, 0.3 mM EDTA, then filter sterilized. Protein concentration was determined by the BCA method (Schuh, J. Fairclough, G. F., and Haschemeyer, R. H. (1978) Proc. Natl. Acad. Sci. USA 75, 3173-3177) (Pierce). The degree of oxidation was determined by TBARS (Chomczynski, P. (1993) Biotechniques 15, 532-537), and was between 25-30 nmol MDA equivalents/mg protein. The differentiated THP-1 cells were exposed for 24 hours to either 50 µg/ml oxidized LDL or NaCl-EDTA buffer in RPMI medium with 10% lipoprotein-deficient fetal bovine serum (Sigma). To harvest the RNA, the plates were rinsed with 10 ml of PBS, then 14 ml of TRIZOL (Liang, P. and Pardee, A. B. (1992) Science 257, 967-971) (GIBCO) were added to each plate. The solution was pipetted several times to mix, then like samples were pooled into centrifuge tubes and 3 ml chloroform per plate were added and mixed. The tubes were centrifuged for 15 minutes at 12000×g. After centrifugation the upper layer was transferred to a new tube and 7.5 ml isopropanol per plate was added and mixed. The tubes were centrifuged at 12000×g for 20 minutes. The pellet was rinsed with ice-cold 70% ethanol and dried at room temperature. The pellets were suspended in 500 µl TE (Tris-EDTA) and treated with 200 units RNase-free DNAse 1 and 200 units RNASIN placental RNase inhibitor (Promega) for 30 minutes at 37° C. The RNA was purified by sequential extractions with phenol, phenol/chloroform/isoamyl alcohol (25:24:1), and chloroform/isoamyl alcohol (24:1) followed by ethanol precipitation.

B) cDNA Synthesis cDNA synthesis and PCR amplification were accomplished using protocols from the Differential Display Kit, version 1.0 (Display Systems Biotechnology, Inc.) This system is based on the technique originally described by Liang and Pardee (Mead, D. A., Pey, N. K., Hermstadt, C., Marcil, R. A., and Smith, L. M., (1991) Bio/Technology 9, 657-663). The primer pairs which yielded the cDNA fragment containing the first information of the lipase like gene were downstream primer 7 and upstream primer 15. The cDNA for the amplification was synthesized as follows, using RNA derived from PMA treated THP-1 cells exposed to either buffer or oxidized LDL: 3 µl of 25 µM downstream primer 7 and 7.5 µl of diethylpyrocarbonate (DEPC)-treated water were added to 300 ng (3.0 µl) RNA from either sample of THP-1 RNA. This was heated to 70° C. for 10 minutes then chilled on ice. To this tube were added 3 µl of 5×PCR buffer (250 mM Tris-HCl pH 8.3, 375 mM KCl)(GIBCO), 3 µl 25 mM $MgCl_2$, 3 µl 0.1 M DTT, 1.2 µl 500 µM dNTPs, 0.7 µl RNASIN, and 5.6 µl DEPC-treated water. The tubes were incubated for 2 minutes at room temperature, after which 1.5 it (300 units) SUPERSCRIPT II RNase H-reverse transcriptase (GIBCO) were added. The tubes were incubated sequentially at room temperature for 2 minutes, 60 minutes at 37° C., and 5 minutes at 95° C., followed by chilling on ice. PCR amplification was performed using a master mix containing 117 µl 10×PCR buffer (500 mM KCl, 100 mM Tris-HCl pH 8.3, 15 mM $MgCl_2$, and 0.01% (w/v) gelatin), 70.2 µl 25 mM $MgCl_2$, 5.9 µl alpha-$^{33}$P dATP (10 m Ci/ml, DuPont NEN), 4.7 µl 500 µM dNTP mix, 11 µl AMPLITAQ DNA polymerase (5 units/µl, Perkin-Elmer), and 493.3 µl DEPC-treated water. For each reaction, 12 µl of the master mix was added to 2 µl downstream primer #7, 1 µl of cDNA, and 5 µl of upstream primer #15. The reaction mixes were heated to 94° C. for 1 minute, then thermocycled 40 times with a denaturing step of 94° C. for 15 seconds, annealing step of 40° C. for 1 minute, and an extension step of 72° C. for 30 seconds. Following the 40 cycles, the reactions were incubated at 72° C. for 5 minutes and stored at 10° C. The PCR reactions were performed in a Perkin-Elmer GENEAMP System 9600 thermocycler.

Four microliters of the amplification reaction were mixed with an equal volume of loading buffer (0.2% bromphenol blue, 0.2% Xylene cyanol, 10 mM EDTA pH 8.0, and 20% glycerol). Four microliters of this mix was run on a 6% nondenaturing acrylamide sequencing format gel for 3 hours at 1200 volts (constant voltage). The gel was dried at 80° C. for 1.5 hours and exposed to Kodak XAR film. An amplification product found only in the reaction containing cDNA from THP-1 cells exposed to oxidized LDL was identified and excised from the gel. 100 µl of DEPC-treated water was added to a microcentrifuge tube containing the excised gel fragment and was incubated for 30 minutes at room temperature followed by 15 minutes at 95° C.

To reamplify the PCR product, 26.5 microliters of the eluted DNA were used in a amplification reaction that also included 5 µl 10× PCR buffer, 3 µl 25 mM $MgCl_2$, 5 µl 500 µM dNTPs, 5 µl 2 µM downstream primer 7, 7.5 µl upstream primer 15, and 0.5 µl Amplitaq polymerase. The PCR cycling parameters and instrument were as described above. Following amplification, 20 µl of the reamplification was analyzed on an agarose gel and 4 µl was used to subclone the PCR products into the vector pCRII using the TA cloning system (Frohman, M. A., Dush, M. K., and Martin, G. R. (1988) Proc. Natl. Acad. Sci. USA 85, 8998-9002) (Invitrogen). Following an overnight ligation at 14° C., the ligation products were used to transform E. coli. Resulting transformants were picked and 3 ml overnight cultures were used in plasmid minipreparations. Insert sizes were determined using EcoRI digestions of the plasmids and clones containing inserts of the approximate size of the original PCR product were sequenced using fluorecent dye-terminator reagents (Prism, Applied Biosystems) and an Applied Biosystems 373 DNA sequencer. The sequence of the PCR product is shown in FIG. 2. The sequence of the amplification primers is underlined.

C) 5' RACE Reaction

Extension of the cDNA identified through RT-PCR was accomplished using the 5' RACE system (Loh, E. Y., Eliot, J. F., Cwirla, S., Lanier, L. L., and Davis, M. M. (1989) Science 243, 217-219; Simms, D., Guan, N., and Sitaraman, K., (1991) Focus 13,99) (GIBCO). One microgram of the THP-1 RNA (oxidized LDL treated) used initially in the differential display reactions was utilized in the 5' RACE procedure:

1 µl (1 µg) of RNA was combined with 3 µl (3 pmol) primer 2a and 11 µl DEPC-treated water and heated to 70° C. for 10 minutes followed by 1 minute on ice. 2.5 µl 10× reaction buffer (200 mM Tris-HCl pH 8.4, 500 mM KCl), 3 µl 25 mM $MgCl_2$, 1 µl 10 mM dNTP mix, and 2.5 gel 0.1 M DTT were added. The mix was incubated at 42° C. for 2 minutes, then 1 µl SUPERSCRIPT II reverse transcriptase was added. The reaction was incubated for an additional 30 minutes at 42° C., 15 minutes at 70° C., and on ice for 1 minute. One microliter of RNase H (2 units) was added and the mixture was incubated at 55° C. for 10 minutes. The cDNA was purified using the GLASSMAX columns (Sambrook, J. Fritsch, E. F., and Maniatis, T. (1989) Molecular Cloning: A Laboratory Manual, second edition, Cold Spring Harbor Laboratory Press, Plainview, N.Y.) included in the kit. The cDNA was eluted from the column in 50 µl $dH_2O$, lyophilized, and resuspended in 21 µl dH₂O. Tailing of the cDNA was accomplished in the following reaction: 7.5 µl dH₂O, 2.5 µl reaction buffer (200 mM Tris-HCl pH 8.4, 500 mM KCl), 1.5 µl 25 mM MgCl₂, 2.5 µl 2 mM dCTP, and 10 µl of the cDNA were incubated at 94° C. for 3 minutes, then 1 minute on ice. 1 µl (10 units) of terminal deoxynucleotidyl transferase was added and the mixture was incubated for 10 minutes at 37° C. The enzyme was heat inactivated by incubation at 70° C. for 10 minutes and the mixture was placed on ice. PCR amplification of the cDNA was performed in the following steps: 5 µl of the tailed cDNA was included in a reaction which also contained 5 µl 10× PCR buffer (500 mM KCl, 100 mM Tris-HCl pH 8.3, 15 mM MgCl₂, and 0.01% (w/v) gelatin), 1) µl 10 mM dNTP mix, 2 gel (10 pmol) anchor primer, 1 µl (20 pmol) primer 3a, and 35 µl dH₂O. The reaction was heated to 95° C. for 1 minute, then 0.9 µl (4.5 units) AMPLITAQ polymerase was added. The reaction was cycled 40 times under the following conditions: 94° C. for 5 seconds, 50° C. for 20 seconds, and 72° C. for 30 seconds. One microliter of this reaction was used in a nested reamplification to increase levels of specific product for subsequent isolation. The reamplification included: 1 µl primary amplification, 5 µl 10× PCR buffer, 1 µl 10 mM dNTP mix, 2 µl (20 pmol) universal amplification primer, 2 µl (20 pmol) primer 4a, and 38 µl dH₂O. The reaction was heated to 95° C. for 1 minute, then 0.7 µl (3.5 units) AMPLITAQ polymerase was added. The reaction was cycled 40 times under these conditions: 94° C. for 5 seconds, 50° C. for 20 seconds, and 72° C. for 30 seconds. The amplification products were analyzed via 0.8% agarose gel electrophoresis. A predominant product of approximately 1.2 kilobase pairs was detected. Two microliters of the reaction products were cloned into the pCRII vector from the TA cloning kit (Invitrogen) and incubated at 14° C. overnight. The ligation products were used to transform *E. coli*. The insert sizes of the resulting transformants were determined following EcoRI digestion. Clones containing inserts of the approximate size of the PCR product were sequenced using fluorescent dye-terminator reagents (PRISM, Applied Biosystems) and an Applied Biosystems 373 DNA sequencer. The sequence of the RACE product including the EcoRI sites from the TA vector are shown in FIG. 3. The sequences of the amplimers (universal amplification primer and the complement to 5'RACE primer 4a) are underlined.

Example 2

Cloning and Chromosomal Localization of the LLGXL Gene

A) cDNA Library Screening

A human placental cDNA library (Oligo dT and random primed, Cat #5014b, Lot #52033) was obtained from Clontech (Palo Alto, Calif.). A radiolabeled probe was created by excising the insert of a plasmid containing the 5'RACE reaction PCR product described above. The probe was radiolabeled using the random priming technique: the DNA fragment (50-100 ng) was incubated with 1 µg of random hexamers (Gibco) at 95° C. for 10 minutes followed by 1 minute on ice. At room temperature the following were added: 3 µl 10× Klenow buffer (100 mM Tris-HCl pH 7.5, 50 mM MgCl₂, 57 mM dithiothreitol; New England Biolabs), 3 µl 0.5 mM dATP, dGTP, dTTP), 100 µCi α-³²PdCTP (3000 Ci/mmol, New England Nuclear), and 1 µl Klenow fragment of DNA polymerase I (5 units, Gibco). The reaction was incubated for 2-3 hours at room temperature and the reaction was then stopped by increasing the volume to 100 µl with TE pH 8.0 and adding EDTA to a final concentration of 1 mM. The unincorporated nucleotides were removed by raising the reaction volume to 100 µl and passing over a G-50 spin column (Boehringer Mannheim). The resulting probes had a specific activity greater than 5×10⁸ cpm/µg DNA.

The library was probed using established methods (Walter, P., Gilmore, R., and Blobel, G. (1984) Cell 38, 5-8). Briefly, the filters were hybridized for 24 hours at 65° C. in 4.8× SSPE (20× SSPE=3.6 M NaCl, 0.2 M NaH₂PO₄, 0.02 M EDTA, pH 7.7), 20 mM Tris-HCl pH 7.6, 1× Denhardt's solution (100×=2% Ficoll 400, 2% polyvinylpyrrolidone, 2% BSA), 10% dextran sulfate, 0.1% SDS, 100 µg/ml salmon sperm DNA, and 1×10⁶ cpm/ml radiolabelled probe. Filters were then washed three times for 15 minutes at room temperature in 2× SSC (1×SSC=150 mM NaCl, 15 mM sodium citrate pH 7.0), 0.1% sodium dodecyl sulfate (SDS) followed by three washes for 15 minutes each at 65° C. in 0.5× SSC, 0.1% SDS. Phage which hybridized to the probe were isolated and amplified. DNA was purified from the amplified phage using LAMBDASORB reagent (Promega) according to the manufacturer's instructions. The inserts were excised from the phage DNA by digestion with EcoRI. The inserts were subcloned into the EcoRI site of a plasmid vector (BLUESCRIPT II SK, STRATAGENE). The sequence of the open reading frame contained within the 2.6 kb EcoRI fragment of the cDNA was determined by automated sequencing as described above. The sequence is shown in FIG. 4. The amino acid sequence of the predicted protein encoded by the open reading frame is shown in FIG. 5 and has been termed LLGXL. The first methionine is predicted to be encoded by nucleotide pairs 252-254. The predicted protein is 500 amino acids in length. The first 18 amino acids form a sequence characteristic of a secretory signal peptide (Higgins, D. G., and Sharp, P. M. (1988) Gene 73, 237-244). The propeptide is predicted to have a molecular weight of 56,800 Daltons. Assuming cleavage of the signal peptide at position 18, the unmodified mature protein has a molecular weight of 54,724 Daltons.

The overall similarities between this protein and the other known members of the triacylglycerol lipase family is illustrated in FIG. 6 and Table 1. In the alignment shown in FIG. 6, LLG is the polypeptide (SEQ ID NO: 6) encoded by the cDNA (SEQ ID NO: 5) described in Example 1, and hereafter referred to as LLGN. This protein is identical with the LLGXL protein in the amino terminal 345 residues. Nine unique residues are followed by a termination codon, producing a propolypeptide of 39.3 kD and a mature protein of 37.3 kD. The sequences which are common to LLGN and LLGXL are nucleic acid sequence SEQ ID NO: 9 and amino acid sequence SEQ ID NO: 10.

Interestingly, the position at which the LLGN and LLGXL proteins diverge is at a region known from the structure of the other lipase to be between the amino and carboxy domains of the proteins. Therefore, the LLGN protein appears to consist of only one of the two domains of triaclyglycerol lipases. This sequence contains the characteristic "GXSXG" lipase motif at positions 167-171 as well as conservation of the catalytic triad residues at Ser 169, Asp 193, and His 274. Conservation of cysteine residues (positions 64, 77, 252, 272, 297, 308, 311, 316, 463, and 483) which have been implicated in disulfide linkage in the other lipases suggests that the LLGXL protein has structural similarities to the other enzymes. There are five predicted sites for N-linked glycosylation; at amino acid positions 80, 136, 393, 469, and 491. The protein sequences used in the comparisons are human lipoprotein lipase (LPL; Genbank accession #M15856, SEQ ID NO: 13), Human hepatic-lipase (HL; Genbank accession #J03540, SEQ ID NO: 14), human pancreatic lipase (PL; Genbank accession # M93285, SEQ ID NO: 15), human pancreatic lipase related protein-1 (PLRP-1; Genbank accession # M93283), and human pancreatic lipase related protein-2 (PLRP-2; Genbank accession # M93284).

TABLE 1

Similarity of triacylglycerol lipase gene family

| | LLGXL | LPL | HL | PL | PLRP1 | PLRP2 |
|---|---|---|---|---|---|---|
| LLGXL | — | 42.7 | 36.5 | 24.5 | 22.5 | 22.6 |
| LPL | 42.7 | — | 40.0 | 22.8 | 22.7 | 20.9 |
| HL | 36.5 | 40.0 | — | 22.8 | 24.0 | 22.0 |
| PL | 24.5 | 22.8 | 22.8 | — | 65.2 | 62.2 |
| PLRP1 | 22.5 | 22.7 | 24.0 | 65.2 | — | 61.7 |
| PRLP2 | 22.6 | 20.9 | 22.0 | 62.2 | 61.7 | — |

Percent similarity was based on pairwise alignment using the Clustal algorithm (Camps, L., Reina, M., Llobera, M., Vilaro, S., and Olivecrona, T. (1990) Am. J. Physiol. 258, C673-C681) in the Megalign program of the Lasergene Biocomputing Software Suite (Dnastar).

B) Chromosomal Localization

DNA from a P1 clone (Sternberg, N., Ruether, J. and DeRiel, K. The New Biologist 2:151-62, 1990) containing genomic LLG DNA was labelled with digoxigenin UTP by nick translation. Labelled probe was combined with sheared human DNA and hybridized to PHA stimulated peripheral blood lymphocytes from a male donor in a solution containing 50% formamide, 10% dextran sulfate, and 2× SSC. Specific hybridization signals were detected by incubating the hybridized cells in fluoresceinated antidigoxigenin antibodies followed by counterstaining with DAPI. This initial experiment resulted in specific labeling of a group E chromosome, which was believed to be chromosome 18 on the basis of DAPI staining.

A second experiment was conducted in which a biotin labelled probe specific for the centromere of chromosome 18 was cohybridized with the LLG probe. This experiment resulted in the specific labeling of the chromosome 18 centromere in red and the long arm of chromosome 18 in green. Measurements of II specifically labelled hybridized chromosomes 18 demonstrated that LLG has a FIter of 0.67 (Franke measurement of 0.38), which corresponds to band 18q21. Several genetic diseases, including intrahepatic cholestasis, cone rod dystrophy, and familial expansile osteolysis, are believed to involve defects in this chromosomal region.

Example 3

LLG RNA Analysis

A) Expression of LLG RNA in THP-1 Cells

Analysis of the mRNA from which the cDNA was derived was performed by northern analysis of THP-1 RNA. RNA from these cells was prepared as described above. The mRNA was purified from the total RNA through the use of a poly-dT-magnetic bead system (Polyattract system, Promega). Three micrograms of poly (A)-containing mRNA was electrophoresed on a 1% agarose-formaldehyde gel. The gel was washed for 30 minutes in $dH_2O$. RNAs were vacuum transferred to a nylon membrane using alkaline transfer buffer (3M NaCl, 8 mM NaOH, 2 mM sarkosyl). After transfer, the blot was neutralized by incubation for 5 minutes in 200 mM phosphate buffer pH 6.8. The RNA was crosslinked to the membrane using an ultraviolet crosslinker apparatus (Stratagene).

A probe was made by excising the insert of a plasmid containing the 5' RACE reaction PCR product described above. The probe was radiolabeled using the random priming technique described in Example 2.

Figure 7:
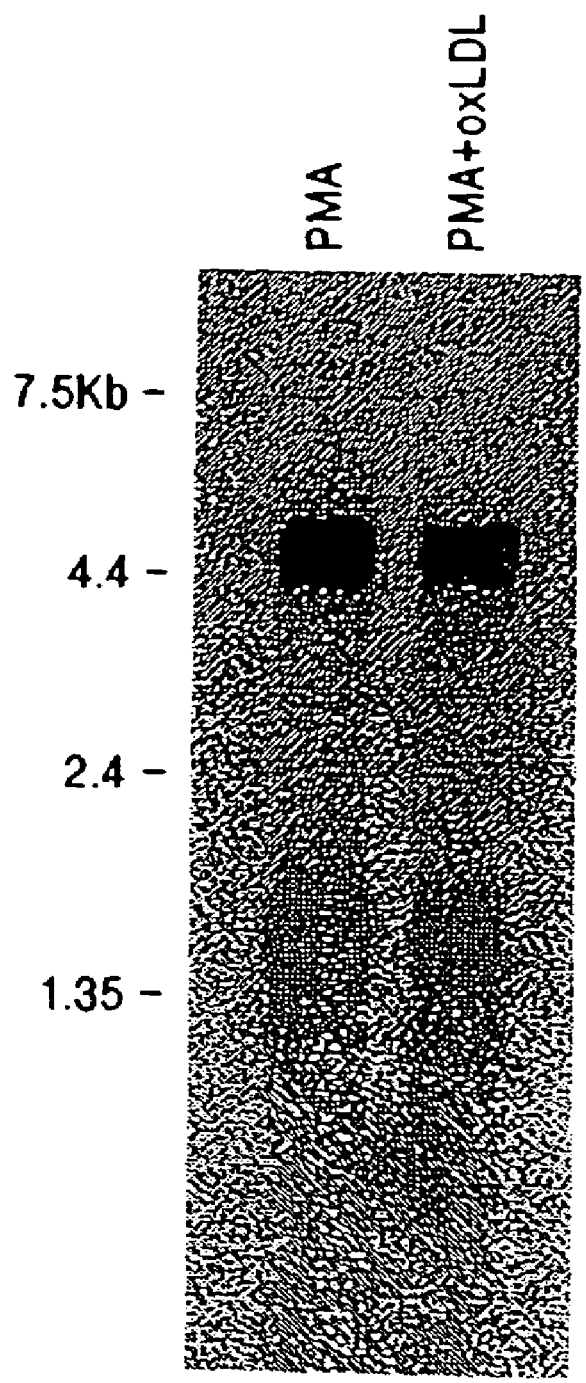
FIG. 7 shows a northern analysis of LLG mRNA in THP-1 cells. Cells were stimulated with either PMA or PMA and oxidized LDL (PMA+oxLDL). Numbers at the left indicate the positions of RNA standards (in kilobases).

The filters were prehybridized in QUICKHYB rapid hybridization solution (Stratagene) for 30 minutes at 65° C. The radiolabeled probe ($1-2\times10^6$ cpm/ml) and sonicated salmon sperm DNA (final concentration 100 μg/ml) were denatured by heating to 95° C. for 10 minutes and quick-chilled on ice before adding to the filter in QUICKHYB. Hybridization was for 3 hours at 65° C. The unhybridized probe was removed by washing the filters two times for 15 minutes with 2× SSC, 0.1% sodium dodecyl sulfate at room temperature followed by two times for 15 minutes in 0.1× SSC, 0.1% SDS at 62° C. Following the washes, the filters were allowed to dry briefly and then exposed to Kodak XAR-2 film with intensifying screens at −80° C. The results are shown in FIG. 7, which shows a major mRNA species of approximately 4.5 kilobases. Minor species of 4.3 and 1.6 kilobases are also present. The expected size of the LLGN cDNA is 1.6 kb. The LLGXL sequence is likely to be encoded by the major species of mRNA detected.

B) Expression of LLG RNA in Various Human Tissues.

A commercially prepared filter containing 3 μg each of mRNAs from human tissues (heart, brain, placenta, lung, liver, skeletal muscle, kidney, and pancreas) was obtained from Clontech (Catalog #7760-1). This filter was probed and processed as described above. After probing with the radiolabeled LLG fragment and autoradiography, the probe was stripped by washing in boiling 0.1× SSC, 0.1% SDS for 2×15 min. in a 65° C. incubator. The membranes were then probed with a 1.4 kilobase pair DNA fragment encoding human Lipoprotein lipase. This fragment was obtained by RT-PCR of the THP-1 RNA (PMA and oxLDL treated) using the 5'LPL and 3'LPL primers described in FIG. 1. and the RT-PCR conditions described above. After autoradiography, the membranes were stripped again and reprobed with a radiolabeled fragment of the human beta actin cDNA to normalize for RNA content. The results of these analyses are shown in FIG. 8. The highest levels of LLG message were detected in placental RNA, with lower levels found in RNAs derived from lung, liver, and kidney tissue. In agreement with previous studies by others (Verhoeven, A. J. M., Jansen, H. (1994) Biochem. Biophys. Acta 1211, 121-124), lipoprotein lipase message was found in many tissues, with highest levels found in heart and skeletal muscle tissue. Results of this analysis indicates that the tissue distribution of LLG expression is very different from that of LPL. The pattern of LLG expression is also different from that of either hepatic lipase or pancreatic lipase, as reported by others (Wang, C.-S., and Hartsuck, J. A. (1993) Biochem. Biophys. Acta 1166, 1-19; Semenkovich, C. F., Chen, S.-W., Wims, M., Luo C.-C., Li, W.-H., and Chan, L. (1989) J. Lipid Res. 30, 423-431; Adams, M. D., Kerlavage, A. R., Fields, C., and Venter, C. (1993) Nature Genet. 4, 256-265).

To determine the expression pattern in additional human tissues, another commercially prepared membrane was probed with LLGXL cDNA. This dot blot (Human RNA Master Blot, Clontech Cat. #7770-1) contains 100-500 ng mRNA from 50 different tissues and is normalized for equivalent housekeeping gene expression (Chen, L., and Morin, R. (1971) Biochim. Biophys. Acta 231, 194-197). A 1.6 kb DraI-SrfI fragment of the LLGXL cDNA was labeled with $^{32}PdCTP$ using a random oligonucleotide priming system (Prime It II, Stratagene) according to the manufacturer's instructions. After 30 minutes prehybridization at 65° C., the probe was added to QuikHyb hybridization solution at 1.3× $10^6$ cpm/ml. Hybridization was for 2 hours at 65° C. The unhybridized probe was removed by washing the filters two times for 15 minutes with 2× SSC, 0.1% sodium dodecyl sulfate at room temperature followed by two times for 15 minutes in 0.1× SSC, 0.1% SDS at 62° C. Following the washes, the filters were allowed to dry briefly and then exposed to Kodak XAR-2 film with intensifying screens at −80° C. for varying amounts of time. The resulting images were quantitated by densitometry. The results are shown in Table 2. The relative expression levels of tissues represented in both the multiple tissue northern and the multiple tissue dot blot are similar, with highest levels in placenta, and lower levels in lung, liver and kidney. Fetal liver, kidney, and lung also express roughly the same levels as the adult tissues. Surprisingly, thyroid tissue expression levels were the highest of all tissues represented, with expression of 122% of that in placental tissue. While there is precedence for lipase expression by the placenta (Rothwell, J. E., Elphick, M. C. (1982) J. Dev. Physiol. 4, 153-159; Verhoeven, A. J. M., Carling D., and Jansen H. (1994) J. Lipid Res. 35, 966-975; Burton, B. K., Mueller, H. W. (1980) Biochim. Biophys. Acta 618, 449-460), the thyroid was not previously known to express any lipase. These results suggest that LLG expression may be involved in maintenance of the placenta, where LLG may serve to liberate free fatty acids from substrates such as phospholipids as a source of energy. The LLG expressed in the thyroid may provide precursors for the synthesis of bioactive molecules by that gland.

partially purify and concentrate the LLG proteins because of the conservation of residues in the LLGXL sequence which have been identified as critical for the heparin-binding activity of LPL (Ma, Y., Henderson, H. E., Liu, M.-S., Zhang, H., Forsythe, I. J. Clarke-Lewis, I., Hayden, M. R., and Brunzell, J. D. J. Lipid Res. 35, 2049-2059; and FIG. 6.). After rotation at 4° C. for 1 hour, the samples were centrifuged for 5 minutes at 150×g. The medium was aspirated and the SEPHAROSE was washed with 14 ml PBS. After centrifugation and aspiration, the pelleted heparin-SEPHAROSE was suspended in 200 µl 2× SDS loading buffer (4% SDS, 20% glycerol. 2% β-mercaptoethanol, 0.002% bromphenol blue, and 120 mM Tris pH 6.8). The samples were heated to 95° C. for 5 minutes and 40 µl was loaded onto a 10% Tris-Glycine SDS gel. After electrophoresis at 140 V for approximately 90 minutes, the proteins were transferred to nitrocellulose membranes via a NOVEX electroblotting apparatus (210 V, 1 hour). The membranes were blocked for 30 minutes in blocking buffer (5% nonfat dried milk, 0.1% Tween 20, 150 mM sodium chloride, 25 mM Tris pH 7.2). Antipeptide antisera and normal rabbit serum was diluted 1:5000 in blocking buffer and was incubated with the membranes overnight at 4° C. with gentle agitation. The membranes were then washed 4×15 minutes with TBST (0.1% Tween 20, 150 mM sodium chloride, 25 mM Tris pH 7.2). Goat anti-rabbit peroxidase conjugated antisera (Boehringer Mannheim) was diluted 1:5000 in blocking buffer and incubated with the membrane for 1 hour

TABLE 2

Expression of LLG mRNA in various human tissues

| | | | | | | | | | |
|---|---|---|---|---|---|---|---|---|---|
| whole brain | N.D. | substantial migra | N.D. | uterus | N.D. | mammary gland | N.D. | lung | 29 |
| amygdata | N.D. | temporal lobe | N.D. | prostate | 5 | kidney | 44 | trachea | 12 |
| caudate nucleus | N.D. | thalamus | N.D. | stomach | N.D. | liver | 61 | placenta | 100 |
| cerebellum | 4 | sub-thalamic nucleus | N.D. | testes | 9 | small intestine | 6 | fetal brain | 5 |
| cerebral cortex | N.D. | spinal cord | N.D. | ovary | N.D. | spleen | N.D. | fetal heart | N.D. |
| frontal lobe | N.D. | heart | N.D. | pancreas | N.D. | thymus | N.D. | fetal kidney | 56 |
| hippocampus | N.D. | sorta | N.D. | pituitary gland | N.D. | peripheral leukocyte | N.D. | fetal liver | 14 |
| medulla oblongata | N.D. | skeletal muscle | N.D. | adrenal gland | N.D. | lymph node | N.D. | fetal spleen | N.D. |
| occipital lobe | N.D. | colon | 8 | thyroid gland | 122 | bone marrow | N.D. | fetal thymus | N.D. |
| putamen | N.D. | bladder | N.D. | salivary gland | N.D. | appendix | 7 | fetal lung | 8 |

Values given are percentage of expresssion with levels in placental tissue arbitrarily set at 100%. Values are average of densitometric measurements from two autoradiographic exposures.
N.D. = not detectable.

Values given are percentage of expression with levels in placental tissue arbitrarily set at 100%. Values are average of densitometric measurements from two autoradiographic exposures. N.D.=not detectable.

C) Expression of LLG RNA in Cultured Endothelial Cells.

Figure 11:
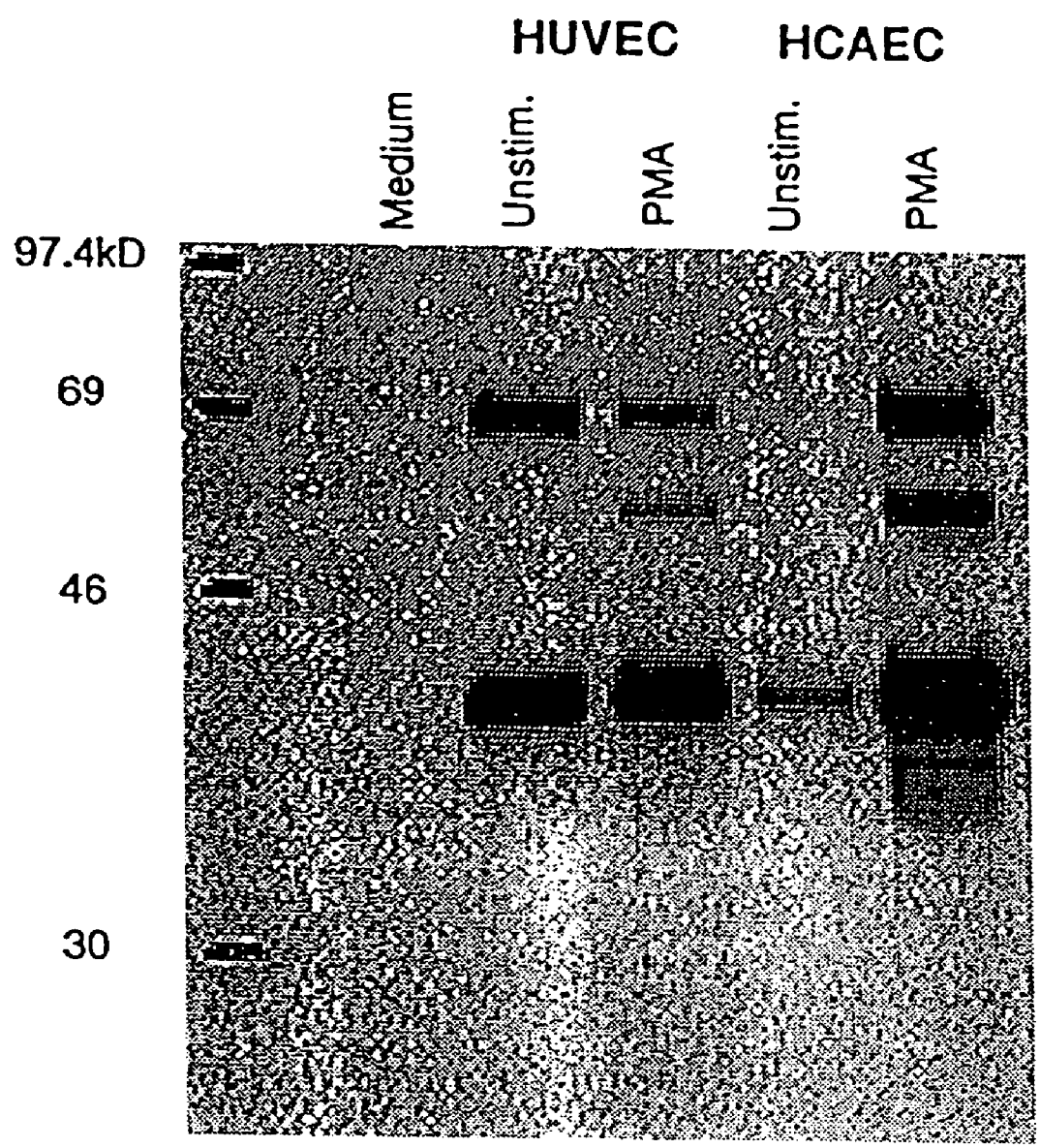
FIG. 11 shows a western analysis of heparin-Sepharose concentrated proteins from conditioned media from cultured endothelial cells. The blot was probed with anti-LLG antiserum. The numbers to the left indicate the positions of protein standards in kilodaltons.

HUVEC and HCEAC cells were cultured and stimulated with PMA as described in Example 3 C, except that the cells were stimulated with PMA for 48 hours. Samples of conditioned medium (9 ml) were incubated with 500 µl of a 50% slurry of heparin-SEPHAROSE CL-6B in phosphate buffered saline (PBS, 150 mM sodium chloride, 100 mM sodium phosphate, pH 7.2). Heparin-SEPHAROSE was chosen to with agitation. The membranes were washed as above, reacted with RENAISSANCE chemiluminescent reagent (DuPont NEN), and exposed to Kodak XAR-2 film. The results are shown in FIG. 11. Two species of immunoreactive proteins are present in the samples from unstimulated HUVEC and HCAEC cells. Levels of immunoreactive protein in the unstimulated HCAEC samples are much lower than the corresponding HUVEC sample. Upon stimulation with PMA, three immunoreactive proteins are secreted by the endothelial cell cultures. PMA exposure greatly increased the level of LLG proteins produced by the HCAEC cultures. PMA induction of LLG proteins was not as dramatic in the HUVEC cultures.

Example 5

Recombinant LLG Protein Production

A) LLG Expression Constructs

The cDNAs encoding the LLGN and LLGXL proteins were cloned into the mammalian expression vector pCDNA3 (Invitrogen). This vector allows expression of foreign genes in many mammalian cells through the use of the cytomegalovirus major late promoter. The LLGN 5' RACE product was cloned into the EcoRI site of pCDNA3. The LLGXL cDNA was digested with DraI and SrfI to yield a 1.55 kb cDNA (see FIG. 4.). The vector was digested with the restriction enzyme EcoRV and the vector and insert were ligated using T4 DNA ligase and reagents from the Rapid Ligation Kit (Boehringer Mannheim) according to the manufacturers instructions. The ligation products were used to transform competent E. coli. Resultant colonies were screened by restriction analysis and sequencing for the presence and orientation of the insert in the expression vector.

B) Transient Transfection of LLG in COS-7 Cells.

Figure 12:
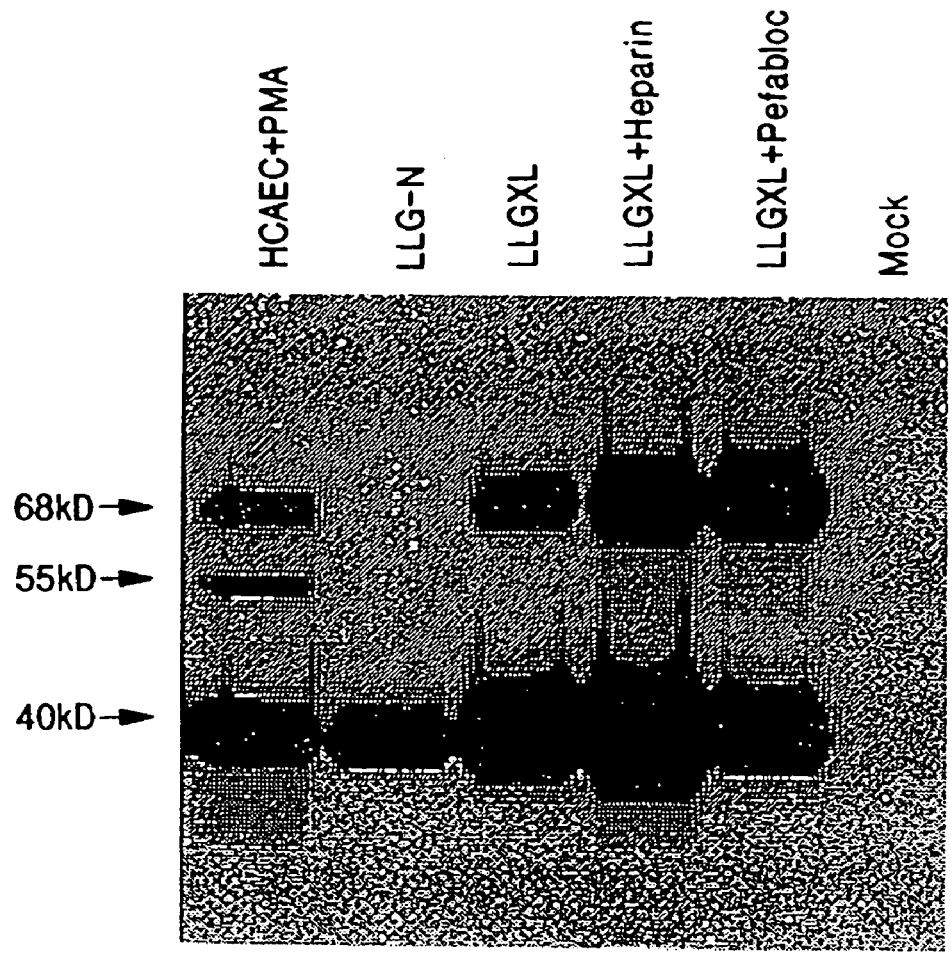
FIG. 12 shows a western analysis of heparin-Sepharose bound proteins in conditioned medium from COS-7 cells transiently transfected with an expression vector containing a cDNA for LLGN or LLGXL or no DNA (Mock). Proteins from PMA-stimulated endothelial cells (HCAEC+PMA) were included for size reference. Numbers to the left indicate the apparent molecular weight of the major immunoreactive proteins as determined by a comparison to protein standards.

The LLG expression vectors were introduced into COS-7 cells through the use of LIPOFECTAMINE cationic lipid reagent (GIBCO). Twenty-four hours before the transfection, COS-7 cells were plated onto 60 mm tissue culture dishes at a density of $2 \times 10^5$ cells/plate. The cells were propagated in Dulbecco's modified Eagle's medium (DMEM; GIBCO) supplemented with 10% fetal calf serum, 100 U/ml penicillin, 100 µg/ml streptomycin. One microgram of plasmid DNA was added to 300 µl of OPTIMEM I serum-free medium (GIBCO). Ten microliters of LIPOFECTAMINE reagent were diluted into 300 µl of Optimem I medium and this was combined with the DNA solution and allowed to sit at room temperature for 30 minutes. The medium was removed from the plates and the cells were rinsed with 2 ml of OPTIMEN medium. The DNA-LIPOFECTAMINE solution was added to the plates along with 2.7 ml OPTIMEN medium and the plates were incubated for 5 hours at 37° C. After the incubation, the serum free medium was removed and replaced with DMEM supplemented with 2% FBS and antibiotics. Twelve hours post-transfection, some of the cultures were treated with either 0.25 mM PEFABLOC SC (Boehringer Mannheim), a protease inhibitor, or 10 U/ml heparin. Thirty minutes before harvest, the heparin treated samples were treated with an additional 40 U/ml heparin. The medium was removed from the cells 60 hours after transfection. Heparin-SEPHAROSE CL-4B (200 µl of a 50% slurry in PBS pH 7.2) was added to 1 ml of medium and was mixed at 4° C. for 1 hour. The SEPHAROSE was pelleted by low speed centrifugation and was washed three times with 1 ml cold PBS. The SEPHAROSE was pelleted and suspended in 100 µl 2× loading buffer. The samples were heated to 95° C. for 5 minutes. 40 µl of each sample was loaded onto a 10% SDS-PAGE gel. Electrophoresis and western analysis was performed using the anti-LLG antiserum as described above. The results are shown in FIG. 12. Proteins from HCAEC conditioned medium were included for size references. LLGN migrates at approximately 40 kD, corresponding to the lowest band in HCAEC. The medium from COS cells transfected with LLGXL cDNA contains both 68 kD and 40 kD species. When these cells were treated with heparin, the amount of both 68 kD and 40 kD proteins recovered from the medium increased dramatically, indicating either the release of proteoglycan-bound protein from the cell surface or stabilization of the proteins by heparin. When the cells were treated with the protease inhibitor PEFABLOC, the amount of 68 kD protein increased relative to that of the 40 kD species. This suggests that the lower molecular weight protein produced by these cells is a proteolysis product of the larger 68 kD form. The role of the mRNA identified through differential display which encodes a shorter, 40 kD species is not known. There has, however, been a report of an alternately-spliced form of hepatic lipase which apparently is expressed in a tissue-specific manner and would create a truncated protein.

Example 6

LLG in Animal Species

A) Cloning the Rabbit Homolog of LLG

Figure 14:
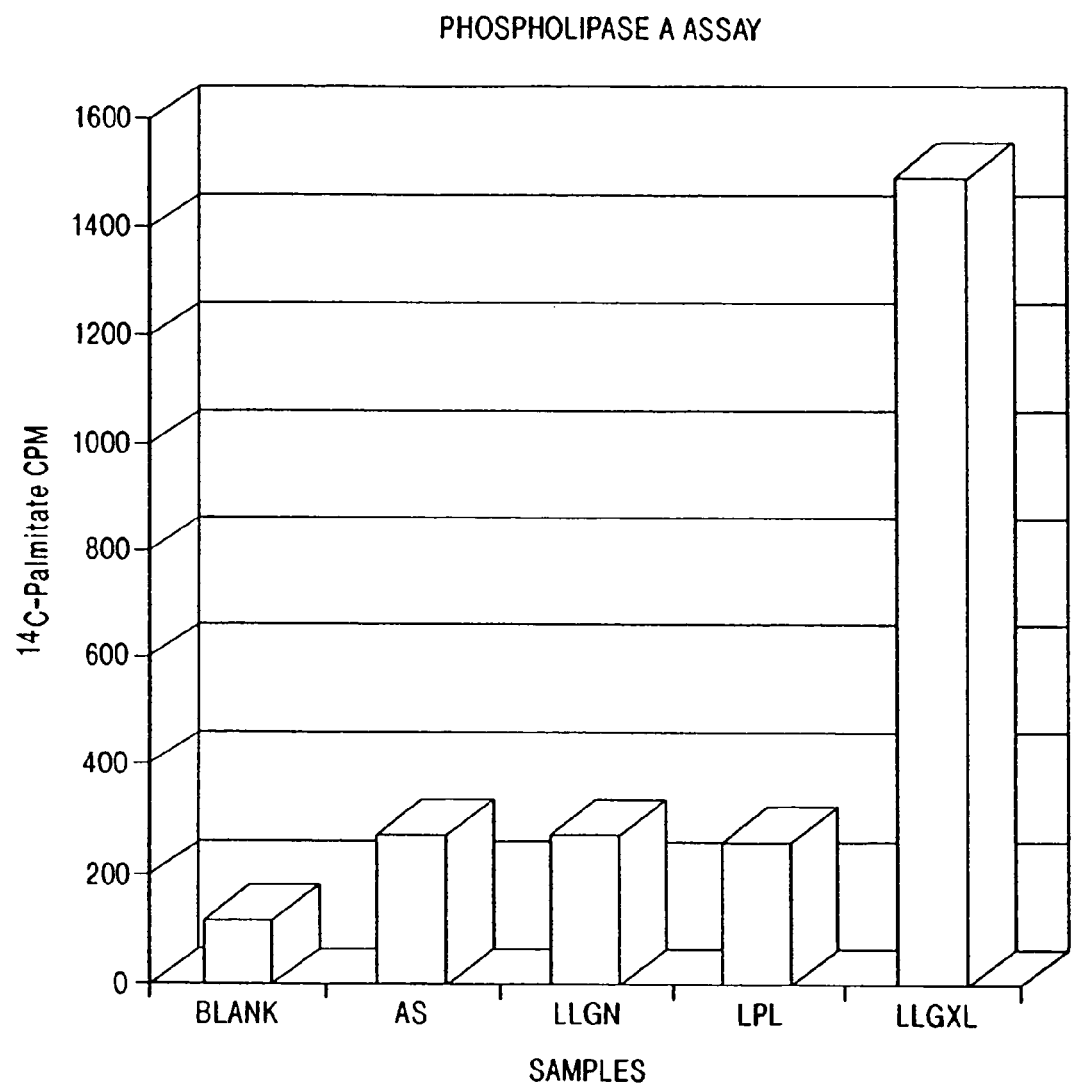
FIG. 14 shows the phospholipase A activity of human LPL, LLGN, and LLGXL, using a phosphatidylcholine substrate.

A commercially available lambda cDNA library derived from rabbit lung tissue (Clontech, Cat. #TL1010b) was used to isolate a fragment of the rabbit homolog of the LLG gene. Five microliters of the stock library were added to 45 µl water and heated to 95° C. for 10 minutes. The following were added in a final volume of 100 µl: 200 µM dNTPs, 20 mM Tris-HCl pH 8.4, 50 mM KCl, 1.5 mM $MgCl_2$, 100 µM each primer DLIP774 and LLGgen2a, and 2.5 U Taq polymerase (GIBCO). The reaction was thermocycled 35 times with the parameters of: 15 seconds at 94° C., 20 seconds at 50° C. and 30 seconds at 72° C. Ten microliters of the reaction was analyzed via agarose gel electrophoresis. A product of approximately 300 basepairs was detected. A portion (4 µl) of the reaction mix was used to clone the product via the TA cloning system. The insert of a resulting clone was sequenced (SEQ ID NO: 11). An alignment between the deduced rabbit amino acid sequence (SEQ ID NO: 12) and the corresponding sequence of the human cDNA is also shown in FIG. 14. Of the nucleotides not part of either amplification primer, there is an 85.8% identity between the rabbit and human LLG sequences. The predicted protein encoded by this rabbit cDNA shares 94.6% identity with that of the human protein, with most of the nucleotide substitutions in the third or "wobble" positions of the codons. Notably, this region spans the "lid" sequence of the predicted LLG proteins and is a variable domain in the lipase gene family. This is evidence that there is a high degree of conservation of this gene between species.

B) LLG in Other Species

To demonstrate the presence of LLG genes in other species, genomic DNAs from various species were restriction digested with EcoRI, separated by electrophoresis in agarose gels, and blotted onto nitrocellulose membranes.

The membranes were hybridized overnight at 65° C. with $2.5 \times 10^6$ cpm/ml of random primed $^{32}$P-LLG or $^{32}$P-LPL (lipoprotein lipase) probe in a hybridization solution of 6× SSC, 10% dextran sulfate, 5× Dendardt's solution, 1% SDS, and 5 µg/ml salmon sperm DNA. The membranes were washed with 0.1× SSC, 0.5% SDS for ten minutes at room temperature, then sequentially for ten minutes at 40° C., 50° C., and 55° C. Autoradiograms of the blots are shown in FIG. 16.

FIG. 16 shows the presence of LLG and LPL genes in all species examined, with the exception that no hybridization was observed with the LLG probe against rat DNA. The exceptional data from rat may represent an artifact caused by generation of abnormally sized restriction fragments containing LLG sequences. Such fragments may be outside of the fractionation range of the agarose gel or may blot inefficiently. The different bands detected by the two probes indicate that LPL and LLG are separate, evolutionarily conserved genes.

Example 7

Enzymatic Activity of LLGXL

A) Phospholipase Activity

Conditioned media from COS-7 cells transiently expressing human lipoprotein lipase (LPL), LLGN, or LLGXL were assayed for phospholipase activity. MEM containing 10% FBS (MEM) was used as the blank, and conditioned media from COS-7 cells transfected with an antisense LLGXL plasmid (AS) was used as a negative control.

A phosphatidylcholine (PC) emulsion was made up using 10 µl phosphatidylcholine (10 mM), 40 µl $^{14}$C-phosphatidylcholine, dipalmitoyl (2 µCi), labelled at the sn 1 and 2 positions, and 100 µl Tris-TCNB [100 mM Tris, 1% Triton, 5 mM $CaCl_2$, 200 mM NaCl, 0.1% BSA). The emulsion was evaporated for 10 minutes, then brought to a final volume of 1 ml in Tris-TCNB.

Reactions were performed in duplicate and contained 50 µl PC emulsion and 950 µl medium. Samples were incubated in a shaking water bath for 2-4 hours at 37° C. The reactions were terminated by adding 1 ml 1N HCl, then extracted with 4 ml of 2-propanol:hexane (1:1). The upper 1.8 ml hexane layer was passed through a silica gel column, and the liberated $^{14}$C-free fatty acids contained in the flow-thru fraction were quantitated in a scintillation counter. The results of these assays are shown in FIG. 14.

B) Triacylglycerol Lipase Activity

Conditioned media from COS-7 cells transiently expressing human lipoprotein lipase (LPL), LLGN, or LLGXL were assayed for triglycerol lipase activity. MEM containing 10% FBS was used as the blank, and conditioned media from COS-7 cells transfected with an antisense LLGXL plasmid (AS) was used as a negative control.

A concentrated substrate was prepared as an anhydrous emulsion of labeled triolein, [9,10-$^3$H(N)] and unlabeled triolein (final total triolein=150 mg with 6.25×10$^8$ cpm), which was stabilized by adding 9 mg of lecithin in 100% glycerol. 0.56 ml of $^3$H-triolein, (0.28 mCi) was mixed with 0.17 ml of unlabeled triolein and 90 µl of lecithin (9 mg). The mixture was evaporated under a stream of nitrogen. The dried lipid mixture was emulsified in 2.5 ml 100% glycerol by sonication (30 second pulse level 2 followed by 2 second chill cycles over 5 minutes].

The assay substrate was prepared by dilution of 1 volume of concentrated substrate with 4 volumes of 0.2M Tris-HCl buffer (pH 8.0) containing 3% w/v fatty acid free bovine serum albumin. The diluted substrate was vortexed vigorously for 5 seconds.

Figure 15:
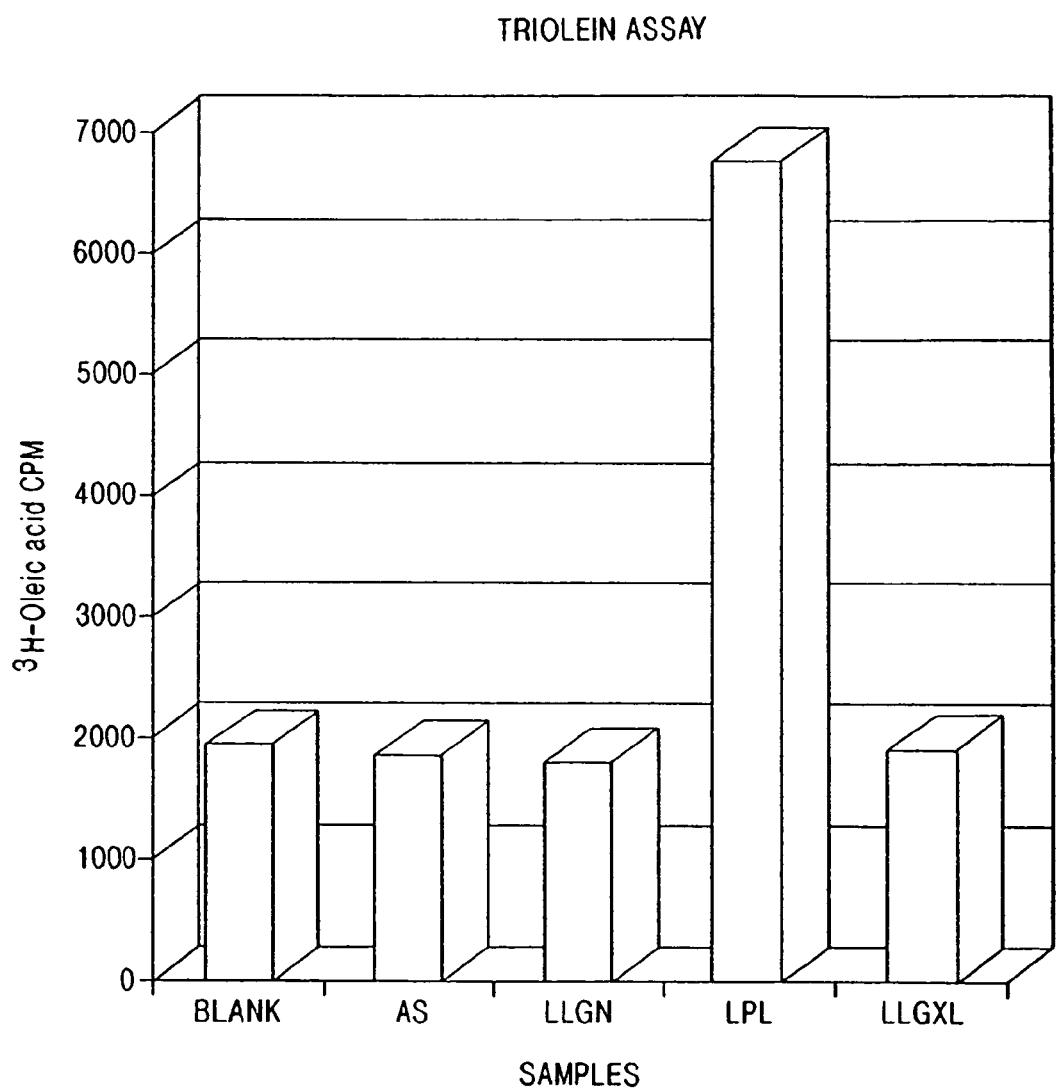
FIG. 15 shows the triacylglyceride lipase activity of human LPL, LLGN, and LLGXL, using a triolein substrate.

Reactions were performed in duplicate in a total volume of 0.2 ml containing 0.1 ml of assay substrate and 0.1 ml of the indicated conditioned media. The reactions were incubated for 90 minutes at 37° C. The reactions were terminated by adding 3.25 ml of methanol-chloroform-heptane 1.41:1.25:1 (v/v/v) followed by 1.05 ml of 0.1M potassium carbonate-borate buffer (pH 10.5). After vigorous mixing for 15 seconds, the samples were centrifuged for 5 minutes at 1000 rpm. A 1.0 ml aliquot of the upper aqueous phase was counted in a scintillation counter. The results of these assays are shown in FIG. 15.

Example 8

Use of LLG Polypeptide to Screen for Agonists or Antagonists

Recombinant LLG is produced in baculovirus-infected insect cells. Recombinant LLG is purified from the serum-containing or serum-free conditioned medium by chromatography on heparin-Sepharose, followed by chromatography on a cation exchange resin. A third chromatographic step, such as molecular sieving, is used in the purification of LLG if needed. During purification, anti-peptide antibodies are used to monitor LLG protein and the phospholipase assay is used to follow LLG activity.

In the fluorescent assay, the final assay conditions are approximately 10 mM Tris-HCl (pH 7.4), 100 mM KCl, 2 mM $CaCl_2$, 5 µM $C_6$NBD-PC{1-acyl-2-[6-(nitro-2,1,3-benzoxadiazol-4-yl)amino]caproylphosphatidylcholine, and LLG protein (approx 1-100 ng). The reaction is subjected to fluorescence excitation at 470 nm, and enzyme activity, as measured by the fluorescence emission at 540 nm is continuously monitored. Compounds and/or substances to be tested for stimulation and/or inhibition of LLG activity are added as 10-200 mM solutions in dimethylsulfoxide. Compounds which stimulate or inhibit LLG activity are identified as causing an increased or decreased fluorescence emission at 540 nm.

In the thio assay, the final assay conditions are approximately 25 mM Tris-HCl (pH 8.5), 100 mM KCl, 10 mM $CaCl_2$, 4.24 mM Triton X-100, 0.5 mM 1,2-bis(hexanoylthio)-1,2-dideoxy-sn-glycero-3-phosphorylcholine, 5 mM 4,4'-dithiobispyridine (from a 50 mM stock solution in ethanol), and 1-100 ng recombinant LLG. Phospholipase activity is determined by measuring the increase in absorption at 342 nm. Compounds and/or substances to be tested for stimulation and/or inhibition of LLG activity are added as 10-200 mM solutions in dimethylsulfoxide. Compounds which stimulate or inhibit LLG activity are identified as causing an increased or decreased absorption at 342 nm.

Example 9

Transgenic Mice Expressing Human LLG

To further study the physiological role of LLG, transgenic mice expressing human LLG are generated.

The 1.53 kb DraI/SrfI restriction fragment encoding LLGXL (see FIG. 4) was cloned into a plasmid vector (pHMG) downstream of the promoter for the ubiquitously expressed 3-hydroxy-3-methylglutaryl coenzyme A (HMG CoA) reductase gene. Transgenic mice expressing different levels of human LLGXL are generated using standard methods (see, e.g., G. L. Tromp et al. Gene 1565:199-205, 1995). The transgenic mice are used to determine the impact of LLGXL overexpression on lipid profile, vascular pathology, rate of development and severity of atherosclerosis, and other physiological parameters.

Example 10

Expression of LLG in Atherosclerotic Tissues

LLGXL expression in atherosclerosis was examined by performing a reverse transcription-polymerase chain reaction (RT-PCR) using mRNA isolated from vascular biopsies from four patients with atherosclerosis. The tissue samples were from the aortic wall (one sample), the iliac artery (two samples), and the carotid artery (one sample).

Atherosclerosis biopsies were received from Gloucestershire Royal Hospital, England, and polyA+ mRNA was prepared and resuspended in diethylpyrocarbonate (DEPC) treated water at a concentration of 0.5 µg/µl mRNA. Reverse transcriptase reactions were performed according to the GibcoBRL protocol for Superscript Preamplification System for First Strand cDNA Synthesis. Briefly, the cDNA was synthesized as follows: 2 µl of each mRNA was added to 1 µl oligo (dT)$_{12-18}$ primer and 9 µl of DEPC water. The tubes were incubated at 70° C. for 10 minutes and put on ice for 1 minute. To each tube, the following components were added: 2 µl 10× PCR buffer, 2 µl 25 mM MgCl$_2$, 1 µl 10 mM dNTP mix and 2 µl 0.1M DTT. After 5 minutes at 42° C., 1 µl (200 units) of Super Script II reverse transcriptase was added. The reactions were mixed gently, then incubated at 42° C. for 50 minutes. The reactions were terminated by incubation at 70° C. for 15 minutes then put on ice. The remaining mRNA was destroyed by the addition of 1 µl of RNase H to each tube and incubated for 20 minutes at 37° C.

PCR amplifications were performed using 2 µl of the cDNA reactions. To each tube the following were added: 5 µl 10× PCR buffer, 5 µl 2 mM dNTPs, 1 µl hllg-gsp1 primer (20 pmol/ml, see FIG. 1), 1 µl hllg-gsp2a primer (20 pmol/ml, see FIG. 1), 1.5 µl 50 mM MgCl$_2$, 0.5 µl Taq polymerase (5 U/ml) and 34 µl water. After holding the reactions at 95° C. for 2 minutes, thirty cycles of PCR were performed as follows: 15 seconds at 94° C., 20 seconds at 52° C., and 30 seconds at 72° C. The finished reactions were held for 10 minutes at 72° C. before analysis by agarose gel electrophoresis. The hllg-gsp primers are specific for LLG and yield an expected product of 300 bp. In a parallel PCR to show that the cDNA synthesis reactions had been successful, primers specific for the housekeeping gene, G3PDH (human glyceraldehyde 3-phosphate dehydrogenase) were used (1 µl each at 20 pmol/ml).

The G3PDH primers (see FIG. 1) yielded the expected product of 983 bp in all four vascular biopsy samples. LLG expression was detected in three of the four samples, with no expression being detected in the carotid artery sample.

All the references discussed herein are incorporated by reference.

One skilled in the art will readily appreciate the present invention is well adapted to carry out the objects and obtain the ends and advantages mentioned, as well as those inherent therein. The peptides, polynucleotides, methods, procedures and techniques described herein are presented as representative of the preferred embodiments, and intended to be exemplary and not intended as limitations on the scope of the present invention. Changes therein and other uses will occur to those of skill in the art which are encompassed within the spirit of the invention or defined by the scope of the appended claims.

We claim:

1. An isolated antibody capable of specifically binding to an isolated polypeptide encoded by a lipase like gene, wherein the polypeptide: (A) binds heparin, (B) has homology with human lipoprotein lipase and hepatic lipase, and (C) comprises a 39 kD catalytic domain of the triacylglycerol lipase family; and wherein the polypeptide comprises an amino acid sequence selected from the group consisting of SEQ ID NO: 6, SEQ ID NO: 8, and SEQ ID NO: 10.

2. The antibody of claim 1 which is able to neutralize the phospholipase activity of the polypeptide.

3. The antibody of claim 1 which is a monoclonal antibody.

4. The antibody of claim 1 which is a polyclonal antibody.

5. A hybridoma cell which produces the antibody of claim 3.

6. A composition comprising the antibody of claim 1 and a biologically compatible solution.

7. A pharmaceutical composition comprising the antibody of claim 1 and a pharmaceutically acceptable carrier.

* * * * *